(12) United States Patent
Norman et al.

(10) Patent No.: US 6,780,874 B2
(45) Date of Patent: Aug. 24, 2004

(54) ENAMINE DERIVATIVES

(75) Inventors: Timothy John Norman, Great Missenden (GB); John Robert Porter, Chinnor (GB); Brian Woodside Hutchinson, Burnham (GB); Andrew James Ratcliffe, Brentford (GB); John Clifford Head, Maidenhead (GB); Rikki Peter Alexander, High Wycombe (GB); Barry John Langham, Reading (GB); Graham John Warrellow, Northwood (GB); Sarah Catherine Archibald, Maidenhead (GB); Janeen Marsha Linsley, High Wycombe (GB)

(73) Assignee: Celltech R & D Limited, Slough (GB)

( * ) Notice: Subject to any disclaimer, the term of this patent is extended or adjusted under 35 U.S.C. 154(b) by 127 days.

(21) Appl. No.: 10/458,234

(22) Filed: Jun. 10, 2003

(65) Prior Publication Data

US 2003/0229116 A1 Dec. 11, 2003

Related U.S. Application Data

(63) Continuation of application No. 09/835,656, filed on Apr. 16, 2001, now Pat. No. 6,610,700.

(30) Foreign Application Priority Data

Apr. 17, 2000 (GB) .............................................. 0009493
Jul. 26, 2000 (GB) .............................................. 0018353
Aug. 2, 2000 (GB) .............................................. 0018966

(51) Int. Cl.[7] .................... A61K 31/435; A61K 31/195; C07C 229/28; C07D 471/04
(52) U.S. Cl. ....................... 514/300; 514/274; 514/300; 514/310; 514/313; 514/335; 514/349; 514/389; 514/530; 514/541; 514/567; 544/317; 546/122; 546/143; 546/159; 546/261; 546/297; 546/323; 560/43; 562/433
(58) Field of Search ................................ 546/122, 143, 546/159, 261, 297, 323; 514/300, 274, 310, 313, 335, 349, 530, 541, 567; 544/317; 560/43; 562/433

(56) References Cited

U.S. PATENT DOCUMENTS

| | | | |
|---|---|---|---|
| 3,938,367 A | 2/1976 | Fletcher et al. | ................ 73/28 |
| 4,470,973 A | 9/1984 | Natarajan et al. | ........... 424/177 |
| 4,554,273 A | 11/1985 | Bayssat et al. | ............. 514/221 |
| 4,987,132 A | 1/1991 | Mase et al. | ................. 514/252 |
| 5,164,372 A | * 11/1992 | Matsuo et al. | ................ 514/90 |
| 5,227,490 A | 7/1993 | Hartman et al. | |
| 5,260,277 A | 11/1993 | McKenzie | .................... 544/18 |
| 5,296,486 A | 3/1994 | Lazer et al. | ................ 514/333 |
| 5,399,585 A | 3/1995 | Alig et al. | .................. 514/438 |
| 5,510,346 A | 4/1996 | Martin et al. | ............... 514/221 |
| 5,698,691 A | 12/1997 | Yukimasa et al. | .......... 540/490 |
| 5,773,646 A | 6/1998 | Chandrakumar et al. | |
| 6,093,696 A | 7/2000 | Head et al. | .................... 514/19 |

FOREIGN PATENT DOCUMENTS

| | | |
|---|---|---|
| DE | 23 16 881 A | 10/1973 |
| DE | 28 37 264 A1 | 3/1979 |
| DE | 196 54 483 A | 1/1998 |
| EP | 0 031 104 A1 | 7/1981 |
| EP | 0 048 763 A1 | 4/1982 |
| EP | 0 144 230 A2 | 6/1985 |

(List continued on next page.)

OTHER PUBLICATIONS

Abraham, W.M. et al., "$\alpha_4$–Integrins Mediate Antigen–Induced Late Bronchial Responses and Prolonged Airway Hyperresponsiveness in Sheep," *J. Clin. Invest.*, 1994, 93, 776–787.

(List continued on next page.)

*Primary Examiner*—Alan L. Rotman
*Assistant Examiner*—Janet L. Coppins
(74) *Attorney, Agent, or Firm*—Woodcock Washburn LLP

(57) ABSTRACT

Enamine derivatives of formula (1) are described:

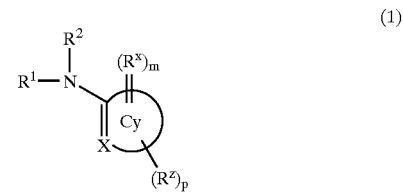

(1)

wherein $R^1$ is a group $Ar^1L^2Ar^2Alk-$ in, which $Ar^1$ is an aromatic or heteroaromatic group, $L^2$ is a covalent bond or a linker atom or group, $Ar^2$ is an arylene or heteroarylene group and Alk is a chain $-CH_2-CH(R)-$, $-CH=C(R)-$ or

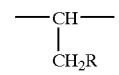

in which R is a carboxylic acid or a derivative or biostere thereof;

$R^2$ is a hydrogen atom or a $C_{1-6}$alkyl group;

Cy is a cycloaliphatic or heterocycloaliphatic ring in which X is a N atom or a $C(R^w)$ group;

$R^x$ is a oxo, thioxo, or imino group;

$R^w$ and $R^z$ is each a hydrogen atom or optional substituent; provided that Cy is not a cyclobutenedione group; and the salts, solvates, hydrates and N-oxides thereof.

The compounds are able to inhibit the binding of integrins to their ligands and are of use in the prophylaxis and treatment of immune or inflammatory disorders, or disorders involving the inappropriate growth or migration of cells.

20 Claims, No Drawings

US 6,780,874 B2
Page 2

FOREIGN PATENT DOCUMENTS

| | | |
|---|---|---|
| EP | 0 288 176 A1 | 10/1988 |
| EP | 0 322 068 A1 | 6/1989 |
| EP | 0 394 989 A2 | 10/1990 |
| EP | 0 498 268 A2 | 8/1992 |
| EP | 0 596 406 A1 | 5/1994 |
| EP | 0 710 657 A1 | 5/1996 |
| EP | 0 710 659 A1 | 5/1996 |
| EP | 0 842 943 A2 | 5/1998 |
| EP | 0 842 945 A2 | 5/1998 |
| JP | 56 090045 | 7/1981 |
| JP | 03 135962 | 6/1991 |
| WO | WO 86/02353 | 4/1986 |
| WO | WO 93/00095 | 1/1993 |
| WO | WO 93/08174 | 4/1993 |
| WO | WO 93/09795 | 5/1993 |
| WO | WO 97/12866 | 4/1997 |
| WO | WO 97/23480 | 7/1997 |
| WO | WO 97/24124 | 7/1997 |
| WO | WO 97/31907 | 9/1997 |
| WO | WO 97/36858 | 10/1997 |
| WO | WO 97/36859 | 10/1997 |
| WO | WO 97/36861 | 10/1997 |
| WO | WO 97/36862 | 10/1997 |
| WO | WO 97/44333 | 11/1997 |
| WO | WO 97/47618 | 12/1997 |
| WO | WO 98/00395 | 1/1998 |
| WO | WO 98/04247 | 2/1998 |
| WO | WO 98/04913 | 2/1998 |
| WO | WO 98/18460 | 5/1998 |
| WO | WO 98/25892 | 6/1998 |
| WO | WO 98/31359 | 7/1998 |
| WO | WO 98/42662 | 10/1998 |
| WO | WO 98/53814 | 12/1998 |
| WO | WO 98/53817 | 12/1998 |
| WO | WO 98/53818 | 12/1998 |
| WO | WO 98/54207 | 12/1998 |
| WO | WO 98/58902 | 12/1998 |
| WO | WO 99/06390 | 2/1999 |
| WO | WO 99/06431 | 2/1999 |
| WO | WO 99/06432 | 2/1999 |
| WO | WO 99/06433 | 2/1999 |
| WO | WO 99/06434 | 2/1999 |
| WO | WO 99/06435 | 2/1999 |
| WO | WO 99/06436 | 2/1999 |
| WO | WO 99/06437 | 2/1999 |
| WO | WO 99/10312 | 3/1999 |
| WO | WO 99/10313 | 3/1999 |
| WO | WO 99/20272 | 4/1999 |
| WO | WO 99/26921 | 6/1999 |
| WO | WO 99/26922 | 6/1999 |
| WO | WO 99/26945 | 6/1999 |
| WO | WO 99/30709 | 6/1999 |
| WO | WO 99/31061 | 6/1999 |
| WO | WO 99/31099 | 6/1999 |
| WO | WO 99/32457 | 7/1999 |
| WO | WO 99/35163 | 7/1999 |
| WO | WO 99/36393 | 7/1999 |
| WO | WO 99/37618 | 7/1999 |
| WO | WO 99/43642 | 9/1999 |
| WO | WO 99/44994 | 9/1999 |
| WO | WO 99/48879 | 9/1999 |
| WO | WO 99/52879 | 10/1999 |
| WO | WO 99/52896 | 10/1999 |
| WO | WO 99/52898 | 10/1999 |
| WO | WO 99/60015 | 11/1999 |
| WO | WO 99/61465 | 12/1999 |
| WO | WO 99/64395 | 12/1999 |
| WO | WO 99/67230 | 12/1999 |
| WO | WO 00/00486 | 1/2000 |
| WO | WO 00/01383 | 1/2000 |
| WO | WO 00/06169 | 2/2000 |
| WO | WO 00/07544 | 2/2000 |
| WO | WO 00/17197 | 3/2000 |
| WO | WO 00/18759 | 4/2000 |
| WO | WO 00/23419 | 4/2000 |
| WO | WO 00/31607 | 6/2000 |
| WO | WO 00/32575 | 6/2000 |
| WO | WO 00/35855 | 6/2000 |
| WO | WO 00/732260 | 12/2000 |

OTHER PUBLICATIONS

Alhaique, F., et al., "Cyclisation of dinitriles by sodium alkoxides a new synthesis of naphthyridines," *Tetrahedron Letters*, 1975, 3, 173–174.

Ames, D.E., et al., "Condensation of β–dicarbonyl compounds with halogenopyridinecarb–oxylic acids. A convenient synthesis of some naphthyridine derivatives," *J.C.S. Perkin I*, 1972, 705–710.

Azzouny, A.E., et al., "Zur Synthese Acyclischer und Cyclischer Anthranilsäure–Phenylalanin–Peptide," *Pharmazie*, 1977, 32(6), 318–323 (German language only).

Bach et al., "Anomalous optical rotation and circular dichroism of N–thioacylated alpha amino acids and deriva," *Acta Chem. Scand.*, 1966, 20(10), 2781–2794.

Badshah, A., et al., "Catalytic reduction of azlactones in alkaline media. Synthesis of amino acids," *J. of Organic Chemistry*, 1972, 37(18), 2916–2918.

Barrett, G.C., "Circular dichroism of N–thiobenzoly–1–α–amino acids. III. Their circular dichroism through the near–ultraviolet wavelength range," *J. Chem. Soc.*, 1967, Section C, 1–5.

Berlin, C. et al., "α4β7 Integrin Mediates Lymphocyte Binding to the Mucosal Vascular Addressin MAdCAM–1," *Cell*, 1993, 74, 185–195.

Binns, R.M. et al., "The Role of E–Selectin in Lymphocyte and Polymorphonuclear Cell Recruitment into Cutaneous Delayed Hypersensitivity Reactions in Sensitized Pigs," *J. Immunol.*, 1996, 157, 4094–409.

Bodor, N., "Novel approaches in prodrug design," *Alfred Benzon Symposium*, 1982, 17, 156–177.

Briskin, M.J. et al., "Structural Requirements for Mucosal Vascular Addressin Binding to Its Lymphocyte Receptor $α_4β_7$," *J. Immunol.*, 1996, 156, 719–726.

Brooks, Peter C., et al., "Antiintegrin αvβ3 blocks human breast cancer growth and angiogenesis in human skin," *J. Clin. Invest.*, 1995, 96, 1815–1822.

Buckle, D.R., et al., "Non Thiazolidinedione Antihyperglycaemic Agents. 1: α–Heteroatom Substituted β–Phenylpropanoic Acids," *Bioorg. Med. Chem. Lett.*, 1996, 6(17), 2121–2126.

Bundgaard, H., *Design of Prodrugs*, 1985, Elsevier, Amsterdam.

Cardarelli, P.M. et al., "Cyclic RGD Peptide Inhibits α4β7 Interaction with Connecting Segment 1 and Vascular Cell Adhesion Molecule," *J. Biol. Chem.*, 1994, 269(28), 18668–18673.

"Cephalosporins," *Jpn. Kokai Tokkyo Koho*, 40 pages, doc. No. 99:5433 (abstract only, 2 pages); JP 57118588.

Koho, *Chemical Abstracts*, "N–[4–Thiazolidinyl)carbonyl] amino acid derivatives," 1981, 95(19), Abstract No. 169173f, 1 page; JP Patent, XP–002114107.

Clausen, K., et al., "Studies on amino acids and peptides. II. Synthesis of protected endothiodipeptides," *J. Chem. Scr.*, 1982, 20(1–2), 14–18, doc. No. 97:163474 (abstract only, 1 page).

Katritzky, A.R., et al. (Eds.), Comprehensive Organic Functional Group Transformations, Pergamon, 1995.

Corey, E.J. et al., "A Synthetic Method for Formyl → Ethynyl Conversion (RCHO → RC≡CH or RC≡CR')," *Tetrahedron Lett.*, 1972, 36, 3769–3772.

Cornforth, J.W., "Oxazoles and Oxazolones," *Chem. Penicillin*, Princeton Book Review, 1949, pp. 688, 799, and 800.

Davies, S..G., et al., "Asymmetric synthesis of R–β–amino butanoic acid and S–β–tyrosine: homochiral lithium amide equivalents for Michael additions to α,β–unsaturated esters," *Tetra. Asymmetry*, 1991, 2(3), 183–186.

Erle, D.J., et al., "Expression and function of the MadCAM–1 receptor, integrin α4β7, on human leukocytes," *J. Immunol.*, 1994, 153, 517–528.

Encyclopedia of Reagents for Organic Synthesis, *John Wiley and Sons* (eds.), 1995.

Ferguson, T.A. et al., "Two integrin–binding peptides abrogate T cell–mediated immune responses in vivo," *Proc. Natl. Acad. Sci. USA*, 1991, 88, 8072–8076.

Frank, R., et al., "Extremely mild reagent for Boc deprotection," *Chem. Commun. (Cambridge)*, 1996, 22, 2509–2510, doc. No. 126:104395 (abstract only, 3 pages).

Fu, H. et al., "Preliminary study on synthesis and antitumor activity in vitro of derivatives of timonacic," *Chemicals Abstracts*, 1988, 108(17), Abstract No. 150358k, 1 page.

Giacomello, et al., "Synthesis of 2,6–naphthyridine," *Tetra. Letters*, 1965, 16, 1117–1121.

Green, T.W., et al., "Protective Groups in Organic Synthesis," *John Wiley and Sons* (eds.), 1991.

Hammes, H., et al., "Subcutaneous injection of a cyclic peptide antagonist of vitronectin receptor–type integrins inhibits retinal neovascularization," *Nature Medicine*, 1996, 2, 529–533.

Harris, R.L.N. et al., *Aust. J. Chem.*, "Potential wool growth inhibitors. 2(1H)–Pyridone analogs of mimosine," 1977, 30(3), 649–655.

Hartke, K. et al., "Dithio and thiono esters. Part 61. Synthesis of α–amino dithioesters and endothiodipeptides,", *J. Prakt. Chem.*, 1996, 338(3), 251–256.

Hodivala–Dilke, K.M., "β3–integrin–deficient mice are a model for glanzmann thrombasthenia showing placental defects and reduced survival," *J. Clin. Invest.*, 1999, 103(2), 229–238.

Holzmann, B., et al., "Peyer's patch–specific lymphocyte homing receptors consist of a VLA–4–like α chain associated with either of two integrin β chains, one of which is novel," *EMBO J.*, 1989, 8(6), 1735–1741.

Humphries, M.J. et al., "Mechanisms of VCAM–1 and fibronectin binding to integrin $\alpha_4\beta_1$: implications for integrin function and rational drug design," *Ciba Foundation Symposium*, 1995, 189, 177–194.

Issekutz, T.B., "Inhibition of Lymphocyte Endothelial Adhesion and In Vivo Lymphocyte Migration to Cutaneous Inflammation by TA–3, a New Monclonal Antibody to Rat LFA–1," *J. Immunol.*, 1992, 149(10), 3394–3402.

Jaynes, B.H. et al., "Synthesis and In Vivo Antibacterial Activity of Hygromycin a Analogs Modified at the $C_4$' Aryl Position," *Bioorg. Med. Chem. Letts.*, 1993, 3(8), 1531–1536.

Jepson, J.B. et al., "Reactions of α–Thioacylamino–acids. Their conversion into Thiazolones and Derivatives Thereof," *J. Chem. Soc.*, 1955, 1791–1797.

Kalvin, D.M., et al., Synthesis of (4R)–D,L–[4–$^2$H]– and (4S)–D,L–[4–$^2$H] homoserine lactones, *J. Org. Chem.*, 1985, 50, 2259–2263.

Keenan, R.M. et al., "Discovery of Potent Nonpeptide Vitronectin Receptor (av$\beta_3$) Antagonists," *J. Med. Chem.*, 1997, 40(15), 2289–2292.

Kobayashi, A., et al., "Synthesis of 2–dialkylamino–4,4–disubstituted 5 (4H)–thiazolones," *J. Yakugaku Zasshi*, 1970, 90(11), 1377–1380, doc. No. 74:31713 (abstract only, 3 pages).

Koenig, H.B., et al., ".beta.–Lactam antibiotics," *Ger. Offen.*, 41 pages, doc. No. 83:97276 (abstract only, 5 pages); German patent.

Koivunen, E., et al., "Selection of peptides binding to the $\alpha_5\beta_1$ integrin from phage display library," *J. Biological Chemistry*, 1993, 268(27), 20205–20210.

Lei, H. et al., "Efficient Synthesis of a Phosphinate Bis–Amino Acid and Its Use in the Construction of Amphiphilic Peptides," *J. Org. Chem.*, 1994, 59, 4206–4210.

Li, Z. et al., "Effect of an anti–Mo1 MAb on ozone–induced airway inflammation and airway hyperresponsiveness in dogs," *Am. J. Physiol.*, 1992, 263(6 Pt 1), L723–726.

Lobb, R.R., et al., "Small molecule antagonists of alpha4 integrins: novel drugs for asthma," *Exp. Opin, Invest. Drugs*, 1999, XP000885957, 8(7), 935–945.

Marlin, S.D. et al., "LFA–1 Immunodeficiency Disease," *J. Exp. Med.*, 1986, 164, 855–867.

Masahiko, M., Japanese Patent No. 57–080370 published May 19, 1982, "Alpha–Methylcinnamic Acid Derivative, its Preparation and Antilipemic Agent Containing The Same," *Patent Abstracts of Japan*, 1982, 1 page.

Masuda, T., *Jpn. Kodai Tokkyo Koho*, 22 pages, doc. No. 115:280022 (abstract only, 1 page); JP patent.

McDowell, R.S. et al., "From Peptide to Non–Peptide. 2. The de Novo Design of Potent, Non–Peptidal Inhibitors of Platelet Aggregation Based on a Benzodiazepinedione Scaffold," *J. Am. Chem. Soc.*, 1994, 116, 5077–5083.

Miller, W.H. et al., "Structure–Activity Relationships in 3–Oxo–1,4–Benzodiazepine–2–Acetic Acid GPIIb/IIIa Antagonists. The 2–Benzazepine Series," *Bioorg. Med. Chem. Lett.*, 1996, 6(21), 2481–2486.

Mitjans, F., et al., "An anti–αv–integrin antibody that blocks integrin function inhibits the development of a human melanoma in nude mice," *J. Cell Science*, 1995, 108, 2825–2838.

Molina, P., et al., "Iminophosphorane–mediated annelation of a pyridine ring into a preformed pyridine one: synthesis of naphthyridine, pyrido [1,2–c] pyrimidine and pyrido [1,2–c] quinazoline derivatives," *Tetrahedron*, 1992, 48(22), 4601–4616.

Nagasawa, H.T. et al., "β–Substituted Cysteines as Sequestering Agents for Ethanol–Derived Acetaldehyde in Vivo," *J. Med. Chem.*, 1987, 30, 1373–1378.

Newham, P., et al., "Integrin adhesion receptors: structure, function and implications for biomedicine," *Nolecular Medicine Today*, 1996, 304–313.

Noike, Y., "Synthesis of Quinolizine Derivatives. VI. Synthesis of 3–Aminoquinolizines. (1). Synthesis of dl–3–Amino–, dl–3–epi–Amino–, and dl–3–epi–Dimethylaminoquinolizidines," *Yakugaku Zasshi*, 1959, 79(12), 1514–1518 (English summary included).

Numata, A., et al., "General synthetic method for naphthyridines and their N-oxides containing isoquinolinic nitrogen," *Synthesis*, 1999, 2, 306-311.

Ohki, S. et al., "Synthesis of quinolizine derivatives. V. Studies on Diastereoisomer of Ethyl 3-Quinolizidinecarboxylate," *Chem. Pharm. Bull.*, 1959, 7(6), 708-712.

Osborne, L., "Leukocyte Adhesion to Endothelium in Inflammation," *Cell*, 1990, 62, 3-6.

Osborn, L. et al., "Direct Expression Cloning of Vascular Cell Adhesion Molecule 1, a Cytokine-Induced Endothelial Protein that Binds to Lymphocytes," *Cell*, 1989, 59, 1203-1211.

Podolsky, D.K. et al., "Attenuation of Colitis in the Cotton-top Tamarin by Anti-α4 integrin Monoclonal Antibody," *J. Clin. Invest.*, 1993, 92, 372-380.

Pfeifer, T., et al., "Specific fragmentation of thioxo peptides facilitates the assignment of the thioxylated amino acid," *J. Mass Spectrom*, 1997, 32(10), 1064-1071, doc. No. 127:331738 (abstract only 2 pages).

Sakamoto, T., et al., "Condensed heteroaromatic ring systems. III. synthesis of naphthyridine derivatives by cyclization of ethynylpyridinecarboxamides," *Chem. Pharm. Bull.* 1985, 33(2), 626-633.

Samanen, J., et al., "Vascular indications for integrin alpha V antagonists," *Current Pharm. Design.*, 1997, 3, 545-584.

Oavrda, J., "CIS-TRANS isomerism of N-ACYL derivatives of proline and its analogues, linear peptides with CIS peptide bonds," *Proc. 14th European Peptide Symposium*, Loffet, A. (ed.), 1976, 653-656.

Sawa, N., et al., "Preparation of 4(5)-thiocarbamoylimidazole compounds," *Jpn. Kokai Tokkyo Koho*, 33 pages, doc. No. 115:183296 (abstract only, 2 pages); JP patent.

Schultz, Von O.-E. et al., "Analogs of nuceic acid bases as antimetabolites," *Arzneimittel Forschung. Drug Res.*, 1967, 17(8), 1060-1064 (English summary included).

Schutkowski, M., et al., "Inhibition of peptidyl-prolyl cis/trans isomerase activity by substrate analog structures: thioxo tetrapeptide-4-nitroanilides," *Biochemistry*, 1995, 34(40), 13016-13026.

Shroff, H.N., et al., "Small peptide inhibitors of $α_4β_7$ mediated MadCAM-1 adhesion to lymphocytes," *Bioorg. Med. Chem. Letts.*, 1996, 6(21), 2495-2500.

Singh, G., et al., "Prodrug approach in new drug design and development," *J. Sci. Ind. Res.*, 1996, 55, 497-510.

Sonnenberg, A., "Integrins and their ligands," *Curr. Topics Microbiol. Immunol.*, 1993, 184, 7-35.

Springer, T.A., "Adhesion receptors of the immune system," *Nature*, 1990, 346, 425-434.

Springer, T.A., "Traffic Signals for Lymphocyte Recirculation and Leukocyte Emigration: The Multistep Paradigm," *Cell*, 1994, 76, 301-314.

Srivatsa, S.S., et al., "Selective αvβ3 integrin blockade potently limits neointimal hyperplasia and lumen stenosis following deep coronary arterial stent injury: evidence for the functional importance of integrin αvβ3 and osteopontin expression during neointima formation," *Cariovascular Research*, 1997, 36, 408-428.

Stupack, D.G., et al., "induction of $α_vβ_3$ integrin-mediated attachment to extracellular matrix in $β_1$ integrin (CD29)-negative B cell lines," *Experi. Cell Research*, 1992, 203, 443-448.

Tan R., et al., "Synthesis of 2, 6-naphthyridine and some of its derivatives," *Tetrahedron Letters*, 1965, 31, 2737-2744.

Tous, G., et al., "O'-(Epoxyalkyl) tyrosines and (Epoxyalkyl) phenylalanine as irreversible inactivators of serine proteases: synthesis and inhibition mechanism," *J. of Medicinal Chemistry*, 1990, 33(6), 1620-1634.

Tsunematsu, H. et al., "Hydrolysis of phenylthiazolones of p-guanidinophenylalanine and arginine by trypsin and related enzymes," *J. Biochem.*, 1983, 94(4), 1119-1125.

Ukai, Y. et al., "A novel synthetic inhibitor of endopeptidase-24.15," *Chemical Abstracts*, 1997, 127(2), 1 page; J. Enzym Inhib., 1996, 11(1), 39-49, reported in CAS.

Vanderslice, P. et al., "A Cyclic Hexapeptide is a Potent Antagonist of α4 Integrins," *J. Immunol.*, 1997, 158, 1710-1718.

Yanigasawa, H. et al., WO 97/37970, "Preparation of phenylalkylcarboxylic acid derivatives lowering blood sugar level," *Chemical Abstracts*, 1997, Abstract 127:307307, 4 pages.

Yang, X., "A predominant role of integrin α4 in the spontaneous development of autoimmune diabetes in nonobese diabetic mice," *Proc. Natl. Acad. Sci. USA*, 1994, 91, 12604-12608.

Yednock, T.A., "Prevention of experimental autoimmune encephalomyelitis by antibodies against α4β1 integrin," *Nature*, 1992, 356, 63-66.

Whitlock, B.J. et al., "Structure and synthesis of lathyrine," *J. Org. Chem.*, 1965, 30, 115-118.

Wojciechowska, H. et al., "Preparation of 2,4-dinitrophenyl derivatives of tyrosine," *Chemical Abstracts*, 1968, 68(25), Abstract No. 114926r, 1 page; *Roc. Chem.*, 1967, 41(9), 1621-1623; reported in CAS.

WPI / Derwent No. XP-002076854, Japanese Patent No. JP 04 193 895 A (Ajinomoto, K.K.), Jul. 13, 1992, DW9234, 1 Page, Abstract Only.

WPI/Derwent No. XP-002076855, Japanese Patent No. JP 56 049 373 A (Dainippon Pharm Co. Ltd.), May 2, 1981, DW8125, 1 page, Abstract only.

Hammadi, A., et al., "Diastereoselective hydrogenation of monodehydro enkephalins controlled by chiral rhodium catalysts," *Tetrahedron: Asymmetry*, 1992, 3(10), XP002106601, 1247-1262.

Nunami, K., et al., "A novel synthesis of methyl 1,5-disubstituted imidazole-4-carboxylates using 3-bromo-2-isocyanoacrylates," *J. Org. Chem.*, 1994, 59, XP002106602, 7635-7642.

Shimohigashi, Y., et al., "Dehydro-enkephalins," *Int. J. Peptide Protein Res.*, 1983, 21, XP002106600, 202-208.

Strange, P.G., et al., "Studies of enzyme-mediated reactions. Part II. Stereochemistry of the elimination of ammonia form L-tyrosine catalysed by the enzyme from maize," *J. Chem. Soc., Perkin I*, 1972, 18, XP002106603, 2364-2372.

WPI/Derwent No. XP002106604, Japanese Patent No. JP 60 190749 (Mitsui Toatsu Chem. Inc.), Sep. 28, 1985, 1 page, Abstract only.

Rico, J.G., et al., "A highly stereoselective michael addition to an αβ-unsaturated ester as the crucial step in the synthesis of a novel β-amino acid-containing fibrinogen receptor antagonist," *J. org. Chem.*, 1993, 58, 7948-7951.

Zablocki, J.A., et al., "Potent in vitro and in vivo inhibitors of platelet aggregation based upon the arg-gly-asp sequence of fibrinogen. (Aminobenzamidino)succinyl (ABAS) series of orally active fibrinogen receptor antagonists," *J. med. Chem.*, 1995, 38, 2378-2394.

Alhaique, F., et al., "91/studies on 2,6–naphthyridine: hydrogenated derivatives and a new ring–closure reaction," *Gazzetta chimica Italinana*, 1975, 105, 1001–1009.

Bordner, J., et al., "1,3–diamino–6,7–dimethoxyisoquinoline derivatives as potential $\alpha_1$–adrenoceptor antagonists," *J. Med. Chem.*, 1988, 31, 1036–1039.

Brun, E.M., et al., "A new synthetic method to 2–pyridones," *Synthesis*, 2000, 2, 273–280.

Brun, E.M., et al., "dienediolates of $\alpha,\beta$–unsaturated carboxylic acids in synthesis: a new synthetic method to 2–pyridones," *Synlett*, 1999, 7, 1088–1090.

Deady, L.W., et al., "Ethoxycarbonylation of $\alpha$–cyano–o–t-oluonitrile and cyclization to isoquinolines and pyrimido[4,5–c]isoquinolines," *Aust. J. Chem.*, 1989, 42, 1029–1034.

Dunn, A.D., "The reaction of some brominated aminopicolines with acetic anhydride and with copper(I) cyanide," *J. prakt. Chem.*, 1996, 338, 663–666.

Falk, H., et al., "On the chemistry of pyrrole pigments, XCI[1]: Copper complexes of pyridinologous linear tri–and tetra–pyrroles as cyclopropanation catalysts," *Monatshefte für Chemie*, 1994, 125, 325–333.

Hiebl, J., et al., "New synthesis of isoquinoline–3–carboxylates," *Tetra. Letts.*, 1999, 40, 7935–7938.

Kaiser, E.M., et al., "Facile synthesis of 1–amino–3–arylisoquinolines," *Synthesis*, 1974, 805–806.

Molina, P., et al., "Preparation and thermal ring–closure of $\beta$–aryl vinyl carbodi–imides: Synthesis of isoquinoline derivatives," *J. Chem. Soc. Perkin Trans. 1*, 1990, 1727–1730.

Myers, A.G., et al., "A practical synthesis of L–azatyrosine," *J. Org. Chem.*, 1996, 61(2), 813–815.

Sheffield, D.J., et al., "Synthesis of some 4–pyridylpyruvic acids as potential lactate dehydrogenase inhibitors," *J.C.S. Perkin I*, 2506–2509.

Tovar, J.D., et al., "Pyrylium salts via electrophilic cyclization: applications for novel 3–arylisoquinoline synthesis," *J. Org. Chem.*, 1999, 64, 6499–6504.

Wenkert, E., et al., "4–acylmethylnicotinonitrile derivatives," *Aust. J. Chem.*, 1972, 25, 433–438.

Wenkert, E., et al., "General methods of synthesis of indole alkaloids. VI. Syntheses of dl–corynantheidine and a camptothecin model," *J. Am. Chem. Soc.*, 1967, 89(25), 6741–6745.

Wu, M., et al., "A direct anionic cyclization of 2–alkynylbenzonitrile to 3–substituted–1(2H)–isoquinolines and 3–benzylideneisoindol–2–ones initiated by methoxide addition," *Tetrahedron*, 1999, 55, 13193–13200.

Crabbe, P., et al., "Cotton effect of dimedone and dihydro–resorcinol condensation compounds of amino acids and peptides," *Tetrahedron*, 1968, 4315–4326.

Aonuma, S., et al., "Effect of thyroid–stimulating hormone, thyroxine, diiodotyrosine, 2,4–dinitrophenol, and related compounds on thiamine metabolism," *Hormones and Related Substances, Chemical Abstracts Service*, 72, accession No. CA57:15725b, XP002206383, CAS RN: 7093–57–4, 1 page (Abstract).

Henke, B.R., et al., "N–(2–Benzoylphenyl)–L–tyrosine PPAR$\gamma$ Agonists. 1. Discovery of a novel series of potent antihyperglycemic and antihyperlipidemic agents," *J. Med. Chem.*, 1998, 41, 5020–5036.

Okuyama, T., "Preparation and properties of 2,4,6–trinitrophenylamino acids and peptides," *Chemical Abstracts Service*, accession No. CA54:244701, XP002206384, CA RNs: 111798–41–5; 133101–94–7 2 pages (abstract).

Penders, T.J., et al., "Mass spectral identification of the methyl esters of 2,4–dinitrophenylamino acids," *Electric and Magnetic Phenomena, Chemical Abstracts Service*, 1966, 65, accession No. CA65:1554b, XP002206328; CAS RNs: 7002–97–1; 10455–88–6, 1 page (Abstract).

\* cited by examiner

ENAMINE DERIVATIVES

This application is a continuation of U.S. application Ser. No. 09/835,656, filed Apr. 16, 2001 now U.S. Pat. No. 6,610,700, which claims the benefit of United Kingdom Application Nos. 0009493.8, filed Apr. 17, 2000; 0018353.3, filed Jul. 26, 2000; and 0018966.2, filed Aug. 2, 2000, each of which is hereby incorporated by reference in its entirety.

The invention relates to a series of enamine derivatives, to compositions containing them, to processes for their preparation, and to their use in medicine.

Over the last few years it has become increasingly clear that the physical interaction of inflammatory leukocytes with each other and other cells of the body plays an important role in regulating immune and inflammatory responses [Springer, T. A., Nature, 346, 425, (1990); Springer, T. A, Cell, A, 301, (1994)]. Specific cell surface molecules collectively referred to as cell adhesion molecules mediate many of these interactions.

The adhesion molecules have been sub-divided into different groups on the basis of their structure. One family of adhesion molecules which is believed to play a particularly important role in regulating immune and inflammatory responses is the integrin family. This family of cell surface glycoproteins has a typical non-covalently linked heterodimer structure. At least 16 different integrin alpha chains and 8 different integrin beta chains have been identified [Newman, P. et al, Molecular Medicine Today, 304, (1996)]. The members of the family are typically named according to their heterodimer composition although trivial nomenclature is widespread in the field. Thus the integrin $\alpha 4\beta 1$ consists of the integrin alpha 4 chain associated with the integrin beta 1 chain, but is also widely referred to as Very Late Antigen 4 or VLA-4. Not all of the potential pairings of integrin alpha and beta chains have yet been observed in nature and the integrin family has been subdivided into a number of subgroups based on the pairings that have been recognised to date [Sonnenberg, A., Current Topics in Microbiology and Immunology, 184, 7, (1993)].

The importance of integrin function in normal physiological responses is highlighted by two human deficiency diseases in which integrin function is defective. Thus in the disease termed Leukocyte Adhesion Deficiency (LAD) there is a defect in one of the families of integrins expressed on leukocytes [Marlin, S. D. et al, J. Exp. Med. 164, 855, (1986)]. Patients suffering from this disease have a reduced ability to recruit leukocytes to inflammatory sites and suffer recurrent infections, which in extreme cases may be fatal. In the case of patients suffering from the disease termed Glanzman's thrombasthenia (a defect in a member of the beta 3 integrin family) there is a defect in blood clotting (Hodivala-Dilke, K. M., J. Clin. Invest. 103, 229, (1999)].

The potential to modify integrin function in such a way as to beneficially modulate cell adhesion has been extensively investigated in animal models using specific antibodies and peptides that block various functions of these molecules [e.g. Issekutz, T. B., J. Immunol. 149, 3394, (1992); Li, Z. et al, Am. J. Physiol. 263, L723, (1992); Mitjans, F. et al, J. Cell Sci. 108, 2825, (1995); Brooks, P. C. et al, J. Clin. Invest. 96, 1815, (1995); Binns, R. M. et al, J. Immunol. 157, 4094, (1996); Hammes, H.-P. et al, Nature Medicine 2, 529, (1996); Srivata, S. et al, Cardiovascular Res. 36, 408 (1997)]. A number of monoclonal antibodies which block integrin function are currently being investigated for their therapeutic potential in human disease, and one, ReoPro, a chimeric antibody against the platelet integrin $\alpha IIb\beta 3$ is in use as a potent anti-thrombotic agent for use in patients with cardiovascular complications following coronary angioplasty.

Integrins recognize both cell surface and extracellular matrix ligands, and ligand specificity is determined by the particular alpha-beta subunit combination of the molecule [Newman, P., ibid]. One particular integrin subgroup of interest involves the $\alpha 4$ chain which can pair with two different beta chains $\beta 1$ and $\beta 7$ [Sonnenberg, A, ibid]. The $\alpha 4\beta 1$ pairing occurs on many circulating leukocytes (for example lymphocytes, monocytes, eosinophils and basophils) although it is absent or only present at low levels on circulating neutrophils. $\alpha 4\beta 1$ binds to an adhesion molecule (Vascular Cell Adhesion Molecule-1 also known as VCAM-1) frequently up-regulated on endothelial cells at sites of inflammation [Osborne, L., Cell, 62, 3, (1990)]. The molecule has also been shown to bind to at least three sites in the matrix molecule fibronectin [Humphries, M. J. et al, Ciba Foundation Symposium, 189, 177, (1995)]. Based on data obtained with monoclonal antibodies in animal models it is believed that the interaction between $\alpha 4\beta 1$ and ligands on other cells and the extracellular matrix plays an important role in leukocyte migration and activation [Yednock, T. A. et al, Nature, 356, 63, (1992); Podolsky, D. K. et al, J. Clin. Invest. 92, 372, (1993); Abraham, W. M. et al, J. Clin. Invest. 93, 776, (1994)].

The integrin generated by the pairing of $\alpha 4$ and $\beta 7$ has been termed LPAM-1 [Holzmann, B. and Weissman, I. L., EMBO J. 8, 1735, (1989)]. The $\alpha 4\beta 7$ pairing is expressed on certain sub-populations of T and B lymphocytes and on eosinophils [Erle, D. J. et al, J. Immunol. 153, 517 (1994)]. Like $\alpha 4\beta 1$, $\alpha 4\beta 7$ binds to VCAM-1 and fibronectin. In addition, $\alpha 4\beta 7$ binds to an adhesion molecule believed to be involved in the homing of leukocytes to mucosal tissue termed MAdCAM-1 [Berlin, C. et al, Cell, 74, 185, (1993)]. The interaction between $\alpha 4\beta 7$ and MAdCAM-1 may also be important sites of inflammation outside of mucosal tissue [Yang, X.-D. et al, PNAS, 91, 12604, (1994)].

Regions of the peptide sequence recognizeded by $\alpha 4\beta 1$ and $\alpha 4\beta 7$ when they bind to their ligands have been identified. $\alpha 4\beta 1$ seems to recognise LDV, IDA or REDV peptide sequences in fibronectin and a QIDSP sequence in VCAM-1 [Humphries, M. J. et al, ibid] whilst $\alpha 4\beta 7$ recognises a LDT sequence in MAdCAM-1 [Birskin, M. J. et al, J. Immunol. 156, 719, (1996)]. There have been several reports of inhibitors of these interactions being designed from modifications of these short peptide sequences [Cardarelli, P. M. et al, J. Biol. Chem., 269, 18668, (1994); Shorff, H. N. et al, Biorganic Med. Chem. Lett., 6, 2495, (1996); Vanderslice, P. et al, J. Immunol., 158, 1710, (1997)]. It has also been reported that a short peptide sequence derived from the $\alpha 4\beta 1$ binding site in fibronectin can inhibit a contact hypersensitivity reaction in a trinitrochlorobenzene sensitised mouse [Ferguson, T. A, et al, PNAS, 88, 8072, (1991)].

Since the alpha 4 subgroup of integrins are predominantly expressed on leukocytes their inhibition can be expected to be beneficial in a number of immune or inflammatory disease states. However, because of the ubiquitous distribution and wide range of functions performed by other members of the integrin family it is important to be able to identify selective inhibitors of the alpha 4 subgroup.

We have now found a group of compounds which are potent and selective inhibitors of $\alpha 4$ integrins. Members of the group are able to inhibit $\alpha 4$ integrins such as $\alpha 4\beta 1$ and/or $\alpha 4\beta 7$ at concentrations at which they generally have no or minimal inhibitory action on $\alpha$ integrins of other subgroups. These compounds possess the additional advantage of good pharmacokinetic properties, especially low plasma clearance.

Thus according to one aspect of the invention we provide a compound of formula (1)

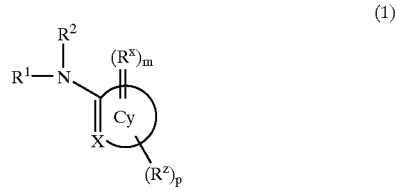

wherein

R$^1$ is a group Ar$^1$L$^2$Ar$^2$Alk- in which Ar$^1$ is an optionally substituted aromatic or heteroaromatic group, L$^2$ is a covalent bond or a linker atom or group, Ar$^2$ is an optionally substituted arylene or heteroarylene group and Alk is a chain

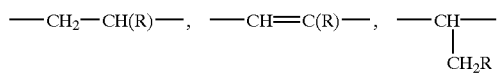

in which R is a carboxylic acid (—CO$_2$H) or a derivative or biostere thereof;

R$^2$ is a hydrogen atom or a C$_{1-6}$alkyl group;

the ring Cy is an unsaturated cycloaliphatic or heterocycloaliphatic ring containing X, in which X is a N atom or a C(R$^w$) group;

R$^w$ is a group R$^z$;

R$^x$ which may be present or any available carbon atom of the ring Cy is a oxo (═O), thioxo (═S) or imino (═NR$^{30}$) group in which R$^{30}$ is an aliphatic, heteroaliphatic, cycloaliphatic, heterocycloaliphatic, aromatic or heteroaromatic group;

m is zero or the integer 1, 2 or 3;

R$^z$ which may be present on any available carbon or nitrogen atom of the ring Cy is selected from a halogen atom or -(Alk$^4$)$_v$L$^1$(Alk$^1$)$_n$R$^3$ in which Alk$^4$ is a straight or branched C$_{1-3}$alkylene chain, v is zero or the integer 1, L$^1$ is a covalent bond or a linker atom or group, n is zero or the integer 1, Alk$^1$ is an optionally substituted aliphatic chain and R$^3$ is a hydrogen atom or a —CN, —NO$_2$ or an optionally substituted heteroaliphatic, cycloaliphatic, heterocycloaliphatic, polycycloaliphatic, heteropolycycloaliphatic, aromatic or heteroaromatic group;

p is zero or the integer 1, 2, 3 or 4;

provided that Cy is not a cyclobutenedione group;

and the salts, solvates, hydrates and N-oxides thereof.

It will be appreciated that compounds of formula (1) may have one or more chiral centres, and exist as enantiomers or diastereomers. The invention is to be understood to extend to all such enantiomers, diastereomers and mixtures thereof, including racemates. Formula (1) and the formulae hereinafter are intended to represent all individual isomers and mixtures thereof, unless stated or shown otherwise.

Optionally substituted aromatic groups represented by Ar$^1$ when present in the group R$^1$ include for example optionally substituted monocyclic or bicyclic fused ring C$_{6-12}$ aromatic groups, such as phenyl, 1- or 2-naphthyl, 1- or 2-tetrahydronaphthyl, indanyl or indenyl groups.

Optionally substituted heteroaromatic groups represented by the group Ar$^1$ when present in the group R$^1$ include for example optionally substituted C$_{1-9}$ heteroaromatic groups containing for example one, two, three or four heteroatoms selected from oxygen, sulphur or nitrogen atoms. In general, the heteroaromatic groups may be for example monocyclic or bicyclic fused ring heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example eight- to thirteen-membered fused-ring heteroaromatic groups containing one, two or more heteroatoms selected from oxygen, sulphur or nitrogen atoms.

Particular examples of heteroaromatic groups of these types include pyrrolyl, furyl, thienyl, imidazolyl, N—C$_{1-6}$ alkylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, [2,3-dihydro]benzothienyl, benzothienyl, benzotriazolyl, indolyl, isoindolyl, benzimidazolyl, imidazo[1,2-a]pyridyl, benzothiazolyl, benzoxazolyl, benzopyranyl, [3,4-dihydro]benzopyranyl, quinazolinyl, quinoxalinyl, naphthyridinyl, e.g. 2,6-naphthyridinyl, pyrido[3,4-b]pyridyl, pyrido[3,2-b] pyridyl, pyrido[4,3-b]-pyridyl, quinolinyl, isoquinolinyl, tetrazolyl, 5,6,7,8-tetrahydroquinolinyl, 5,6,7,8-tetrahydroisoquinolinyl, and imidyl, e.g. succinimidyl, phthalimidyl, or naphthalimidyl such as 1,8-naphthalimidyl.

Each aromatic or heteroaromatic group represented by the group Ar$^1$ may be optionally substituted on any available carbon or, when present, nitrogen atom. One, two, three or more of the same or different substituents may be present and each substituent may be selected for example from an atom or group -L$^3$(Alk$^2$)$_t$L$^4$(R$^4$)$_u$ in which L$^3$ and L$^4$, which may be the same or different, is each a covalent bond or a linker atom or group, t is zero or the integer 1, u is an integer 1, 2 or 3, Alk$^2$ is an aliphatic or heteroaliphatic chain and R$^4$ is a hydrogen or halogen atom or a group selected from optionally substituted C$_{1-6}$alkyl, C$_{3-8}$ cycloalkyl, C$_{6-12}$aromatic or C$_{1-9}$heteroaromatic, —OR$^5$ [where R$^5$ is a hydrogen atom, an optionally substitued C$_{1-6}$alkyl or C$_{3-8}$ cycloalkyl group], —SR$^5$, —NR$^5$R$^6$ [where R$^6$ is as just defined for R$^5$ and may be the same or different], —NO$_2$, —CN, —CO$_2$R$^5$, —SO$_3$H, —SOR$^5$, —SO$_2$R$^5$, —SO$_3$R$^5$, —OCO$_2$R$^5$, —CONR$^5$R$^6$, —OCONR$^5$R$^6$, —CSNR$^5$R$^6$, —COR$^5$, —OCOR$^5$, —N(R$^5$)COR$^6$, —N(R$^5$)CSR$^6$, —SO$_2$N(R$^5$)(R$^6$), —N(R$^5$)SO$_2$R$^6$, N(R$^5$)CON(R$^6$)(R$^7$) [where R$^7$ is a hydrogen atom, an optionally substituted C$_{1-6}$alkyl or C$_{3-8}$cycloalkyl group], —N(R$^5$)CSN(R$^6$)(R$^7$) or —N(R$^5$)SO$_2$N(R$^6$)(R$^7$), provided that when t is zero and each of L$^3$ and L$^4$ is a covalent bond then u is the integer 1 and R$^4$ is other than a hydrogen atom Optionally substituted C$_{6-12}$aromatic and C$_{1-6}$heteroaromatic groups represented by R$^4$ include those aromatic and heteroaromatic groups as described hereinbefore for the group Ar$^1$. Optional substituents which may be present on these groups include those R$^{13}$ optional substituents as described hereinafter.

When L$^3$ and/or L$^4$ is present in these substituents as a linker atom or group it may be any divalent linking atom or group. Particular examples include —O— or —S— atoms or —C(O)—, —C(O)O—, —OC(O)—, —C(S)—, —S(O)—, —S(O)$_2$—, —N(R$^8$)— [where R$^8$ is a hydrogen atom or an optionally substituted straight or branched C$_{1-6}$alkyl group], —CON(R$^8$)—, —OC(O)N(R$^8$)—, —CSN (R$^8$)—, —N(R$^8$)CO—, —N(R$^8$)C(O)O—, —N(R$^8$)CS—, —S(O)$_2$N(R$^8$)—, —N(R$^8$)S(O)$_2$—, —N(R$^8$)O—, —ON (R$^8$)—, —N(R$^8$)N(R$^8$)—, —N(R$^8$)CON(R$^8$)—, —N(R$^8$)

CSN($R^8$)—, or —N($R^8$)SO$_2$N($R^8$)— groups. Where the linker group contains two $R^8$ substituents, these may be the same or different.

When $R^4$, $R^5$, $R^6$, $R^7$ and/or $R^8$ is present as a $C_{1-6}$alkyl group it may be a straight or branched $C_{1-6}$alkyl group, e.g. a $C_{1-3}$alkyl group such as a methyl or ethyl group. $C_{3-8}$cycloalkyl groups represented by $R^4$, $R^5$, $R^6$, $R^7$ and/or $R^8$ include $C_{3-6}$cycloalkyl groups e.g. cyclopropyl, cyclobutyl, cyclopentyl and cyclohexyl groups. Optional substituents which may be present on such groups include for example one, two or three substituents which may be the same or different selected from halogen atoms, for example fluorine, chlorine, bromine or iodine atoms, or hydroxy or $C_{1-6}$alkoxy e.g. methoxy or ethoxy groups.

When the groups $R^5$ and $R^6$ or $R^6$ and $R^7$ are both $C_{1-6}$alkyl groups these groups may be joined, together with the N atom to which they are attached, to form a heterocyclic ring. Such heterocyclic rings may be optionally interrupted by a further heteroatom selected from —O—, —S— or —N($R^5$)—. Particular examples of such heterocyclic rings include piperidinyl, morpholinyl, thiomorpholinyl, pyrrolidinyl, imidazolidinyl and piperazinyl rings.

When $Alk^2$ is present as an aliphatic or heteroaliphatic chain it may be for example any divalent chain corresponding to the below-mentioned aliphatic or heteroaliphatic group described for $Alk^1$ or $R^3$ respectively.

Halogen atoms represented by $R^4$ in the optional $Ar^1$ substituents include fluorine, chlorine, bromine, or iodine atoms.

Examples of the substituents represented by -$L^3$($Alk^1$)$_v$$L^4$($R^4$)$_u$ when present in $Ar^1$ groups in compounds of the invention include atoms or groups -$L^3$$Alk^2$$L^4$$R^4$, -$L^3$$Alk^2$$R^4$, -$L^3$$R^4$, -$R^4$ and -$Alk^2$$R^4$ wherein $L^3$, $Alk^2$, $L^4$ and $R^4$ are as defined above. Particular examples of such substituents include -$L^3$CH$_2$$L^4$$R^4$, -$L^3$CH(CH$_3$)$L^4$$R^4$, -$L^3$CH(CH$_2$)$_2$$L^4$$R^4$, -$L^3$CH$_2$$R^4$, —$L^3$CH(CH$_3$)$R^4$, -$L^3$(CH$_2$)$_2$$R^4$, —CH$_2$$R^4$, —CH(CH$_3$)$R^4$, —(CH$_2$)$_2$$R^4$ and -$R^4$ groups.

Thus $Ar^1$ in compounds of the invention may be optionally substituted for example by one, two, three or more halogen atoms, e.g. fluorine, chlorine, bromine or iodine atoms, and/or $C_{1-6}$alkyl, e.g. methyl, ethyl, n-propyl, i-propyl, n-butyl or t-butyl, $C_{3-8}$cycloalkyl, e.g. cyclopropyl, cyclobutyl, cyclopentyl or cyclohexyl, $C_{1-6}$hydroxyalkyl, e.g. hydroxymethyl, hydroxyethyl or —C(OH)(CF$_3$)$_2$, carboxy$C_{1-6}$alkyl, e.g. carboxyethyl, $C_{1-6}$alkylthio e.g. methylthio or ethylthio, carboxy$C_{1-6}$alkylthio e.g. carboxymethylthio, 2-carboxyethylthio or 3-carboxypropylthio, $C_{1-6}$alkoxy, e.g. methoxy or ethoxy, hydroxy$C_{1-6}$alkoxy, e.g. 2-hydroxyethoxy, halo$C_{1-6}$alkyl, e.g. —CF$_3$, —CHF$_2$, CH$_2$F, halo$C_{1-6}$alkoxy, e.g. —OCF$_3$, —OCHF$_2$, —OCH$_2$F, $C_{1-6}$alkylamino, e.g. methylamino or ethylamino, amino (—NH$_2$), amino$C_{1-6}$alkyl, e.g. aminomethyl or aminoethyl, $C_{1-6}$dialkylamino, e.g. dimethylamino or diethylamino, $C_{1-6}$alkylamino$C_{1-6}$alkyl, e.g. ethylaminoethyl, $C_{1-6}$dialkylamino$C_{1-6}$alkyl, e.g. diethylaminoethyl, amino$C_{1-6}$alkoxy, e.g. aminoethoxy, $C_{1-6}$alkylamino$C_{1-6}$alkoxy, e.g. methylaminoethoxy, $C_{1-6}$dialkylamino$C_{1-6}$alkoxy, e.g. dimethylaminoethoxy, diethylaminoethoxy, diisopropylaminoethoxy, or dimethylaminopropoxy, nitro, cyano, amidino, hydroxyl (—OH), formyl [HC(O)—], carboxyl (—CO$_2$H), —CO$_2$$Alk^3$ [where $Alk^3$ is as defined below for $Alk^7$], $C_{1-6}$ alkanoyl e.g. acetyl, thiol (—SH), thio$C_{1-6}$alkyl, e.g. thiomethyl or thioethyl, sulphonyl (—SO$_3$H), —SO$_3$$Alk^3$, $C_{1-6}$alkylsulphinyl, e.g. methylsulphinyl, $C_{1-6}$alkylsulphonyl, e.g. methylsulphonyl, aminosulphonyl (—SO$_2$NH$_2$), $C_{1-6}$ alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, phenylaminosulphonyl, carboxamido (—CONH$_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, amino$C_{1-6}$alkylaminocarbonyl, e.g. aminoethylaminocarbonyl, $C_{1-6}$dialkylamino$C_{1-6}$alkylaminocarbonyl, e.g. diethylaminoethylaminocarbonyl, aminocarbonylamino, $C_{1-6}$alkylaminocarbonylamino, e.g. methylaminocarbonylamino or ethylaminocarbonylamino, $C_{1-6}$dialkylaminocarbonylamino, e.g. dimethylaminocarbonylamino or diethylaminocarbonylamino, $C_{1-6}$alkylaminocabonyl$C_{1-6}$alkylamino, e.g. methylaminocarbonylmethylamino, aminothiocarbonylamino, $C_{1-6}$alkylaminothiocarbonylamino, e.g. methylaminothiocarbonylamino or ethylaminothiocarbonylamino, $C_{1-6}$dialkylaminothiocarbonylamino, e.g. dimethylaminothiocarbonylamino or diethylaminothiocarbonylamino, $C_{1-6}$alkylaminothiocarbonyl$C_{1-6}$alkylamino, e.g. ethylaminothiocarbonylmethylamino, $C_{1-6}$alkylsulphonylamino, e.g. methylsulphonylamino or ethylsulphonylamino, $C_{1-6}$dialkylsulphonylamino, e.g. dimethylsulphonylamino or diethylsulphonylamino, aminosulphonylamino (—NHSO$_2$NH$_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, $C_{1-6}$alkanoylamino, e.g. acetylamino, amino$C_{1-6}$ alkanoylamino e.g. aminoacetylamino, $C_{1-6}$dialkylamino$C_{1-6}$ alkanoylamino, e.g. dimethylaminoacetylamino, $C_{1-6}$alkanoylamino$C_{1-6}$alkyl, e.g. acetylaminomethyl, $C_{1-6}$alkanoylamino$C_{1-6}$alkylamino, e.g. acetamidoethylamino, $C_{1-6}$alkoxycarbonylamino, e.g. methoxycarbonylamino, ethoxycarbonylamino or t-butoxycarbonylamino groups.

$L^2$ when present as part of the group $R^1$ in compounds of the invention may be a linker atom or group $L^{2a}$ or a linker -($Alk^a$)$L^{2a}$-, where $Alk^a$ is an optionally substituted aliphatic or heteroaliphatic chain as previously defined for $Alk^2$, and $L^{2a}$ is a linker atom or group as described above for $L^3$ and $L^4$.

Optionally substituted arylene groups represented by $Ar^2$ when present as part of the group $R^1$ include those aromatic groups as previously described for $Ar^1$.

Optionally substituted heteroarylene groups represented by $Ar^2$ when present as part of the group $R^1$ include those heteroaromatic groups as previously described for $Ar^1$.

Each arylene or heteroarylene group represented by $Ar^2$ may be attached to the remainder of the molecule through any available ring carbon or nitrogen atoms.

The arylene and heteroarylene groups represented by $Ar^2$ may be optionally substituted by one, two or more substituents selected from the atoms or groups -$L^3$($Alk^2$)$_v$$L^4$($R^4$)$_u$ described herein. Where two of these atoms or groups are present they may be the same or different.

When the group R is present in $R^1$ in compounds of the invention as a derivative of a carboxylic acid it may be for example a carboxylic acid ester or amide. Particular esters and amides include —CO$_2$$Alk^7$ and —CONR$^5$R$^6$ groups as defined herein. When R is a biostere of a carboxylic acid it may be for example a tetrazole or other acid such as phosphonic acid, phosphinic acid, sulphonic acid, sulphinic acid or boronic acid or an acylsulphonamide group.

Esters (—CO₂Alk⁷) and amide (—CONR⁵R⁶) derivatives of the carboxylic acid group (—CO₂H) in compounds of formula (1) may advantageously be used as prodrugs of the active compound. Such prodrugs are compounds which undergo biotransformation to the corresponding carboxylic acid prior to exhibiting their pharmacological effects and the invention particularly extends to produgs of the acids of formula (1). Such prodrugs are well known in the art, see for example International Patent Application No. WO00/23419, Bodor, N. (Alfred Benzon Symposium, 1982, 17, 156–177), Singh, G. et al (J. Sci. Ind. Res., 1996, 55, 497–510) and Bundgaard, H., (Design of Prodrugs, 1985, Elsevier, Amsterdam).

Esterified carboxyl groups represented by the group —CO₂Alk⁷ wherein Alk⁷ include groups is a straight or branched optionally substituted $C_{1-8}$alkyl group such as a methyl, ethyl, n-propyl, i-propyl, n-butyl, i-butyl, s-butyl or t-butyl group, an optionally substituted $C_{2-8}$alkenyl group such as a propenyl e.g. 2-propenyl or butenyl e.g. 2-butenyl or 3-butenyl group, an optionally substituted $C_{2-8}$alkynyl group such as a ethynyl, propynyl e.g. 2-propynyl or butynyl e.g. 2-butynyl or 3-butynyl group, an optionally substituted $C_{3-8}$cycloalkyl group such as a cyclopropyl, cyclobutyl, cyclopentyl, cyclohexyl or cycloheptyl group; an optionally substituted $C_{3-8}$cycloalkyl$C_{1}$8alkyl group such as a cyclopentylmethyl, cyclohexylmethyl or cyclohexylethyl group; an optionally substituted $C_{3-8}$heterocycloalkyl$C_{1-6}$alkyl group such as a morpholinyl-N-ethyl, thiomorpholinyl-N-methyl, pyrrolidinyl-N-ethyl, pyrrolidinyl-N-propyl, piperidinyl-N-ethyl, pyrazolidinyl-N-methyl or piperazinyl-N-ethyl group; an optionally substituted $C_{1-6}$alkyloxy$C_{1-6}$alkyl group such as a methyloxyethyl or propyloxyethyl group; an optionally substituted $C_{1-6}$alkylthio$C_{1-6}$alkyl group such as an ethylthioethyl group; an optionally substituted $C_{1-6}$alkylsulfinyl$C_{1-6}$alkyl group such as an methylsulfinylethyl group; an optionally substituted $C_{1-6}$alkylsulfonyl$C_{1-6}$alkyl group such as an methylsulfonylmethyl group; an optionally substituted $C_{3-8}$cycloalkyloxy$C_{1-6}$alkyl group such as a cyclohexyloxymethyl group; an optionally substituted $C_{3-8}$cycloalkylthio$C_{1-6}$alkyl group such as a cyclopentylthiomethyl group; an optionally substituted $C_{3-8}$cycloalkylsulfinyl$C_{1-6}$alkyl group such as a cyclopentylsulfinylmethyl group; an optionally substituted $C_{3-8}$cycloalkylsulfonyl$C_{1-6}$alkyl group such as a cyclopentylsulfonylmethyl group; an optionally substituted $C_{1-6}$alkyloxycarbonyl$C_{1-6}$alkyl group such as isobutoxycarbonylpropyl group; an optionally substituted $C_{1-6}$alkyloxycarbonyl$C_{1-6}$alkenyl group such as isobutoxycarbonylpentenyl group; an optionally substituted $C_{1-6}$alkyloxycarbonyloxy$C_{1-6}$alkyl group such as an isopropoxycarbonyloxyethyl e.g a 1-(isopropoxycarbonyloxy) ethyl, 2-(isopropoxycarbonyloxy)ethyl or ethyloxycarbonyloxymethyl group; an optionally substituted $C_{1-6}$alkyloxycarbonyloxy$C_{1-6}$alkenyl group such as a isopropoxycarbonyloxybutenyl group, an optionally substituted $C_{3-8}$cycloalkyloxycarbonyloxy$C_{1-6}$alkyl group such as a cyclohexyloxycarbonyloxyethyl, e.g. a 2-(cyclohexyloxycarbonyloxy)ethyl group, an optionally substituted N-di-$C_{1-8}$alkylamino$C_{1-8}$alkyl group such as a N-dimethylaminoethyl or N-diethylaminoethyl group; an optionally substituted N—$C_{6-12}$aryl-N—$C_{1-6}$alkylamino$C_{1-6}$ alkyl group such as a N-phenyl-N-methylaminomethyl group; an optionally substituted N-di-$C_{1-8}$alkylcarbamoyl$C_{1-8}$alkyl group such as a N-diethylcarbamoylmethyl group; an optionally substituted $C_{6-10}$aryl$C_{1-6}$alkyl group such as an optionally substituted benzyl, phenylethyl, phenylpropyl, 1-naphthylmethyl or 2-naphthylmethyl group; a $C_{6-10}$aryl group such as an optionally substituted phenyl, 1-naphthyl or 2-naphthyl group; a $C_{6-10}$aryloxy$C_{1-8}$alkyl group such as an optionally substituted phenyloxymethyl, phenyloxyethyl, 1-naphthyloxymethyl, or 2-naphthyloxymethyl group; a $C_{6-12}$arylthio$C_{1-8}$alkyl group such as an optionally substituted phenylthioethyl group; a $C_{6-12}$arylsulfinyl$C_{1-8}$alkyl group such as an optionally substituted phenylsulfinylmethyl group; a $C_{6-12}$arylsulfonyl$C_{1-8}$alkyl group such as an optionally substituted phenylsulfonylmethyl group; an optionally substituted $C_{1-8}$alkanoyloxy$C_{1-8}$alkyl group, such as a acetoxymethyl, ethoxycarbonyloxyethyl, pivaloyloxymethyl, propionyloxyethyl or propionyloxypropyl group; an optionally substituted $C_{4-8}$imido$C_{1-8}$alkyl group such as a succinimidomethyl or phthalamidoethyl group; a $C_{6-12}$aroyloxy$C_{1-8}$alkyl group such as an optionally substituted benzoyloxyethyl or benzoyloxypropyl group or a triglyceride such as a 2-substituted triglyceride e.g. a 1,3-di-$C_{1-8}$alkylglycerol-2-yl group such as a 1,3-diheptylglycerol-2-yl group. Optional substituents present on the Alk⁷ group include $R^{13a}$ substituents described above.

Optional substituents which may be present on the Alk⁷ group include $R^{13a}$ substituents as defined hereinafter.

When the group $R^2$ is present in compounds of the invention as a $C_{1-6}$alkyl group it may be for example a straight or branched $C_{1-6}$alkyl group, e.g. a $C_{1-3}$alkyl group such as a methyl or ethyl group.

Unsaturated cycloaliphatic groups represented by the ring Cy include unsaturated $C_{4-10}$ cycloaliphatic groups. Particular examples of unsaturated cycloaliphatic groups represented by Cy include $C_{3-7}$cycloalkenyl groups.

Particular examples of unsaturated cycloaliphatic groups represented by Cy include cyclobutenyl, cyclopentenyl, cyclohexenyl and cycloheptenyl groups.

Unsaturated heterocycloaliphatic groups represented by the ring Cy include unsaturated $C_{3-10}$ heterocycloaliphatic groups. Particular examples include optionally substituted $C_{3-10}$ heterocycloalkenyl e.g. $C_{3-7}$ heterocycloalkenyl groups, each of said groups containing one, two, three or four heteroatoms or heteroatom containing groups $L^7$ where $L^7$ is as defined above for $L^3$ where $L^3$ is a linker atom or group. It will be appreciated that when X in the ring Cy is a nitrogen atom then a further heteroatom or heteroatom containing group $L^7$ need not be present in the ring Cy.

Particular examples of unsaturated heterocycloaliphatic groups represented by Cy include dihydrofuranyl, dihydrothiophenyl, 2,3-dihydrothiophene-1,1-dioxide, 3-amino-4,5-dihydro-1,1-dioxothiophenyl [where amino refers to the group $NR^1R^2$], 3,4-dihydrol-1,1-dioxo-2H-thiopyranyl, 2,3,4,5-tetrahydro-1,1-dioxo-thiopinyl, pyrrolinyl, e.g. 2- or 3-pyrrolinyl, oxazolinyl, thia-zolinyl, imidazolinyl, pyrazolinyl, isoxazolinyl, isothiazolinyl, pyranyl, dihydropyridyl, tetrahydropyridyl, dihydropyridazinyl, tetrahydropyridazinyl, dihydropyrimidinyl, tetrahydropyrimidinyl, dihydropyrazinyl, tetrahydro-pyrazinyl, dihydrotriazinyl, tetrahydrotriazinyl, oxazinyl or dihydrothiadia-zinyl group.

When the unsaturated cycloaliphatic or heterocycloaliphatic ring represented by Cy is substituted by a group $R^x$, $R^x$ may be a oxo (═O), thioxo (═S) or imino (═NR³⁰) group. It will be understood that when the ring Cy includes such a group $R^x$, then the corresponding hydroxy (—OH), thiol (—SH) or amino (—NHR³⁰) tautomers in which the double bond migrates to become part of the ring Cy are also included.

When the group $R^{30}$ is present in compounds of formula (1) as an aliphatic group it may be any aliphatic chain as described hereinafter for $Alk^1$ but with each containing a terminal hydrogen atom. When the group $R^{30}$ is present in compounds of formula (1) as a heteroaliphatic, cycloaliphatic, heterocycloaliphatic, aromatic or heteroaromatic group it may be any heteroaliphatic, cycloaliphatic, heterocycloaliphatic, aromatic or heteroaromatic group as described hereinafter for the group $R^3$. Optional substituents which may be present on these groups include any optional substituents described herein in relation to the corresponding $Alk^1$ aliphatic chains or $R^3$ heteroaliphatic, cycloaliphatic, heterocycloaliphatic, aromatic or heteroaromatic groups.

The group $R^z$ when present may be attached to any suitable carbon or nitrogen atom of the unsaturated cycloaliphatic or heterocycloaliphatic ring represented by Cy.

Halogen atoms represented by the group $R^z$ include fluorine, chlorine, bromine and iodine atoms.

$C_{1-3}$ alkylene chains represented by $Alk^4$ in the group $R^z$ in compounds of formula (1) include for example a —$CH_2$—, —$CH_2CH_2$—, —$CH_2CH_2CH_2$—, —$CH(CH_3)CH_2$— or —$CH_2CH(CH_3)$— chain.

When present the linker atom or group represented by $L^1$ in the group $R^z$ in compounds of formula (1) may be any linker atom or group as described above for the linker atom or group $L^3$.

When $Alk^1$ is present in the group $R^z$ in compounds of formula (1) as an optionally substituted aliphatic chain it may be an optionally substituted $C_{1-10}$ aliphatic chain. Particular examples include optionally substituted straight or branched chain $C_{1-6}$ alkylene, $C_{2-6}$ alkenylene, or $C_{2-6}$ alkynylene chains.

Particular examples of aliphatic chains represented by $Alk^1$ include optionally substituted —$CH_2$—, —$(CH_2)_2$—, —$CH(CH_3)CH_2$—, —$(CH_2)_2CH_2$—, —$(CH_2)_3CH_2$—, —$CH(CH_3)(CH_2)_2$—, —$CH_2CH(CH_3)CH_2$—, —$C(CH_3)_2CH_2$—, —$CH_2C(CH_3)_2CH_2$—, —$(CH_2)_2C(CH_3)_2CH_2$—, —$(CH_2)_4CH_2$—, —$(CH_2)_5CH_2$—, —CHCH—, —CHCHCH$_2$—, —CH$_2$CHCH—, —CHCHCH$_2$CH$_2$—, —CH$_2$CHCHCH$_2$—, —$(CH_2)_2$CHCH—, —CC—, —CCCH$_2$—, —CH$_2$CC—, —CCCH$_2$CH$_2$—, —CH$_2$CCCH$_2$— or —$(CH_2)_2$CCH— groups.

Heteroaliphatic groups represented by the group $R^3$ when present in the group $R^z$ in compounds of formula (1) include the aliphatic chains just described for $Alk^1$ but with each containing a terminal hydrogen atom and additionally containing one, two, three or four heteroatoms or heteroatom-containing groups. Particular heteroatoms or groups include atoms or groups $L^5$ where $L^5$ is as defined above for $L^3$ when $L^3$ is a linker atom or group. Each $L^5$ atom or group may interrupt the aliphatic group, or may be positioned at its terminal carbon atom to connect the group to an adjoining atom or group. Particular examples include optionally substituted -$L^5CH_3$, —$CH_2L^5CH_3$, -$L^5CH_2CH_3$, —$CH_2L^5CH_2CH_3$, —$(CH_2)_2L^5CH_3$, —$(CH_2)_3L^5CH_3$, —$L^5(CH_2)_3$, and —$(CH_2)_2L^5CH_2CH_3$ groups.

The optional substituents which may be present on aliphatic chains or heteroaliphatic groups represented by $Alk^1$ and $R^3$ respectively or aliphatic groups represented by -$Alk^1R^3$ include one, two, three or more substituents where each substituent may be the same or different and is selected from halogen atoms, e.g. fluorine, chlorine, bromine or iodine atoms, or —OH, —$CO_2H$, —$CO_2R^9$, where $R^9$ is an optionally substituted straight or branched $C_{1-6}$alkyl group as defined above for $R^4$, —$CONHR^9$, —$CON(R^9)_2$, —$COR^9$, —$COCH_3$, $C_{1-6}$alkoxy, e.g. methoxy or ethoxy, halo$C_{1-6}$alkoxy e.g. —$OCF_3$, thiol, —$S(O)R^9$, —$S(O)_2R^9$, $C_{1-6}$alkylthio e.g. methylthio or ethylthio, amino or substituted amino groups. Substituted amino groups include —$NHR^9$ and —$N(R^9)_2$ groups. Where two $R^9$ groups are present in any of the above substituents these may be the same or different.

Optionally substituted cycloaliphatic groups represented by the group $R^3$ when present in the group $R^z$ in compounds of the invention include optionally substituted $C_{3-10}$ cycloaliphatic groups. Particular examples include optionally substituted $C_{3-10}$ cycloalkyl, e.g. $C_{3-7}$ cycloalkyl or $C_{3-10}$ cycloalkenyl, e.g $C_{3-7}$ cycloalkenyl groups.

Optionally substituted heterocycloaliphatic groups represented by the group $R^3$ when present in the group $R^z$ include optionally substituted $C_{3-10}$heterocycloaliphatic groups. Particular examples include optionally substituted $C_{3-10}$heterocycloalkyl, e.g. $C_{3-7}$ heterocycloalkyl, or $C_{3-10}$heterocycloalkenyl, e.g. $C_{3-7}$ hetercycloalkenyl groups, each of said groups containing one, two, three or four heteroatoms or heteroatom-containing groups $L^5$ as defined above.

Optionally substituted polycycloaliphatic groups represented by the group $R^3$ when present in the group $R^z$ include optionally substitued $C_{7-10}$ bi- or tricycloalkyl or $C_{7-10}$bi- or tricycloalkenyl groups. Optionally substituted heteropolycycloaliphatic groups represented by the group $R^3$ include the optionally substituted polycycloalkyl groups just described, but with each group additionally containing one, two, three or four $L^5$ atoms or groups.

Particular examples of cycloaliphatic, polycycloaliphatic, heterocycloaliphatic and heteropolycycloaliphatic groups represented by the group $R^3$ include optionally substituted cyclopropyl, cyclobutyl, cyclopentyl, cyclohexyl, cycloheptyl, 2-cyclobuten-1-yl, 2-cyclopenten-1-yl, 3-cyclopenten-1-yl, adamantyl, norbornyl, norbornenyl, tetrahydrofuranyl, tetrahydropyranyl, tetrahydrothiopyranyl, pyrroline, e.g. 2- or 3-pyrrolinyl, pyrrolidinyl, pyrrolidinone, oxazolidinyl, oxazolidinone, dioxolanyl, e.g. 1,3-dioxolanyl, imidazolinyl, e.g. 2-imidazolinyl, imidazolidinyl, pyrazolinyl, e.g. 2-pyrazolinyl, pyrazolidinyl, pyranyl, e.g. 2- or 4-pyranyl, piperidinyl, piperidinone, 1,4-dioxanyl, morpholinyl, morpholinone, 1,4-dithianyl, thiomorpholinyl, piperazinyl, 1,3,5-trithianyl, oxazinyl, e.g. 2H-1,3-, 6H-1,3-, 6H-1,2-, 2H-1,2- or 4H-1,4-oxazinyl, 1,2,5-oxathiazinyl, isoxazinyl, e.g. o- or p-isoxazinyl, oxathiazinyl, e.g. 1,2,5 or 1,2,6-oxathiazinyl, or 1,3,5,-oxadiazinyl groups.

The optional substituents which may be present on the cycloaliphatic, polycycloaliphatic, heterocycloaliphatic or heteropolycycloaliphatic groups represented by the group $R^3$ include one, two, three or more substituents each selected from halogen atoms, e.g. fluorine, chlorine, bromine or iodine atoms, or $C_{1-6}$alkyl, e.g. methyl, ethyl or propyl, halo$C_{1-6}$alkyl, e.g. halomethyl or haloethyl such as difluoromethyl or trifluoromethyl, optionally substituted by hydroxyl, e.g. —$C(OH)(CF_3)_2$, $C_{1-6}$alkoxy, e.g. methoxy, ethoxy or propoxy, halo$C_{1-6}$alkoxy, e.g. halomethoxy or haloethoxy such as difluoromethoxy or trifluoromethoxy, thiol, $C_{1-6}$alkylthio e.g. methylthio, ethylthio or propylthio, or -$(Alk^{4a})_gR^{10}$ groups in which $Alk^{4a}$ is a straight or branched $C_{1-3}$alkylene chain, g is zero or an integer 1 and $R^{10}$ is a —OH, —SH, —$N(R^{11})_2$, (in which $R^{11}$ is an atom or group as defined herein for $R^8$) —CN, —$CO_2R^{11}$, —$NO_2$, —$CON(R^{11})_2$, —$CSN(R^{11})_2$, —$COR^{11}$, —$CSN(R^{11})_2$, —$N(R^{11})COR^{11}$, —$N(R^{11})CSR^{11}$, —$SO_2N(R^{11})_2$, —$N(R^{11})SO_2R^{11}$, —$N(R^{11})CON(R^{11})_2$, —$N(R^{11})CSN(R^{11})$, $N(R^{11})SO_2N(R^{11})_2$ or optionally substituted phenyl group. Where two $R^{11}$ atoms or groups are present in these substituents these may be the same or different. Optionally substituted phenyl groups include phenyl substituted by one, two or three of the $R^{13}$ groups described below Additionally, when the group $R^3$ is a heterocycloaliphatic group containing one or more nitrogen atoms each nitrogen atom may be optionally substituted by a group -$(L^6)_p(Alk^5)_q$ $R^{12}$ in which $L^6$ is —C(O)—, —C(O)O—, —C(S)—, —S(O)$_2$—, —CON($R^{11}$)—, —CSN($R^{11}$)— or SO$_2$N($R^{11}$)—; p is zero or an integer 1; Alk$^5$ is an optionally substituted aliphatic or heteroaliphatic chain; q is zero or an integer 1; and $R^{12}$ is a hydrogen atom or an optionally substituted cycloaliphatic, heterocycloaliphatic, polycycloaliphatic, polyheterocycloaliphatic, aromatic or heteroaromatic group.

$C_{1-3}$alkylene chains represented by Alk$^{4a}$ include those groups as previously described for Alk$^4$.

Optionally substituted aliphatic or heteroaliphatic chains represented by Alk$^5$ include those optionally substituted chains described above for Alk$^1$ and $R^3$ respectively. Optional substituents which may be present on these groups include those described above in relation to Alk$^1$ and $R^3$ aliphatic and heteroaliphatic chains.

Cycloaliphatic, heterocycloaliphatic, polycycloaliphatic or polyheterocycloaliphatic groups represented by $R^{12}$ include those groups just described for the group $R^3$. Optional substituents which may be present on those groups include those described above in relation to $R^3$ cycloaliphatic groups.

Aromatic or heteroaromatic groups represented by $R^{12}$ include those groups described herein for the group Ar$^1$. Optional substituents which may be present on these groups include those $R^{13}$ optional substituents described hereinafter.

When the group $R^3$ is an optionally substituted aromatic or heteroaromatic group it may be for example an aromatic or heteroaromatic group as described herein for the group Ar$^1$.

Optional substituents which may be present on the aromatic or heteroaromatic groups represented by the group $R^3$ include one, two, three or more substituents, each selected from an atom or group $R^{13}$ in which $R^{13}$ is -$R^{13a}$ or -Alk$^6$($R^{13a}$)$_m$, where $R^{13a}$ is a halogen atom, or an amino (—NH$_2$), substituted amino, nitro, cyano, amidino, hydroxyl (—OH), substituted hydroxyl, formyl, carboxyl (—CO$_2$H), esterified carboxyl, thiol (—SH), substituted thiol, —COR$^{14}$ [where $R^{14}$ is an -Alk$^6$($R^{13a}$)$_m$, aryl or heteroaryl group], —CSR$^{14}$, —SO$_3$H, —SOR$^{14}$, —SO$_2$R$^{14}$, —SO$_3$R$^{14}$, —SO$_2$NH$_2$, —SO$_2$ NHR$^{14}$ SO$_2$N(R$^{14}$)$_2$, —CONH$_2$, —CSNH$_2$, —CONHR$^{14}$, —CSNHR$^{14}$, —CON[R$^{14}$]$_2$, —CSN(R$^{14}$)$_2$, —N(R$^{11}$)SO$_2$R$^{14}$, —N(SO$_2$R$^{14}$)$_2$, —NH(R$^{11}$)SO$_2$NH$_2$, —N(R$^{11}$)SO$_2$NHR$^{14}$, —N(R$^{11}$)SO$_2$N(R$^{14}$)$_2$, —N(R$^{11}$)COR$^{14}$, —N(R$^{11}$)CONH$_2$, —N(R$^{11}$)CONHR$^{14}$, —N(R$^{11}$)CON(R$^{14}$)$_2$, —N(R$^{11}$)CSNH$_2$, —N(R$^{11}$)CSNHR$^{14}$, —N(R$^{11}$)CSN(R$^{14}$)$_2$, —N(R$^{11}$)CSR$^{14}$, —N(R$^{11}$)C(O)OR$^{14}$, —SO$_2$NHet$^1$ [where —NHet$^1$ is an optionally substituted $C_{5-7}$cyclicamino group optionally containing one or more other —O— or —S— atoms or —N(R$^{11}$)—, —C(O)—, —C(S)—, S(O) or —S(O)$_2$ groups], —CONHet$^1$, —CSNHet$^1$, —N(R$^{11}$)SO$_2$NHet$^1$, —N(R$^{11}$)CONHet$^1$, —N(R$^{11}$)CSNHet$^1$, —SO$_2$N(R$^{11}$)Het$^2$ [where Het$^2$ is an optionally substituted monocyclic $C_{5-7}$carbocyclic group optionally containing one or more —O— or —S— atoms or —N(R$^{11}$)—, —C(O)— or —C(S)— groups], -Het$^2$, —CON(R$^{11}$)Het$^2$, —CSN(R$^{11}$)Het$^2$, —N(R$^{11}$)CON(R$^{11}$)Het$^2$, —N(R$^{11}$)CSN(R$^{11}$)Het$^2$, cycloaliphatic, heterocycloaliphatic, aryl or heteroaryl group; Alk$^6$ is a straight or branched $C_{1-6}$alkylene, $C_{2-6}$alkenylene or $C_{2-6}$alkynylene chain, optionally interrupted by one, two or three —O— or —S— atoms or —S(O)$_n$ [where n is an integer 1 or 2] or —N(R$^{15}$)— groups [where R$^{15}$ is a hydrogen atom or $C_{1-6}$alkyl, e.g. methyl or ethyl group]; and m is zero or an integer 1, 2 or 3. It will be appreciated that when two $R^{11}$ or $R^{14}$ groups are present in one of the above substituents, the $R^{11}$ or $R^{14}$ groups may be the same or different.

When in the group -Alk$^6$($R^{13a}$)$_m$ m is an integer 1, 2 or 3, it is to be understood that the substituent or substituents $R^{13a}$ may be present on any suitable carbon atom in -Alk$^6$. Where more than one $R^{13a}$ substituent is present these may be the same or different and may be present on the same or different atom in -Alk$^6$. Clearly, when m is zero and no substituent $R^{13a}$ is present the alkylene, alkenylene or alkynylene chain represented by Alk$^6$ becomes an alkyl, alkenyl or alkynyl group.

When $R^{13a}$ is a substituted amino group it may be for example a group —NHR$^{14}$ [where $R^{14}$ is as defined above] or a group —N(R$^{14}$)$_2$ wherein each $R^{14}$ group is the same or different.

When $R^{13a}$ is a halogen atom it may be for example a fluorine, chlorine, bromine, or iodine atom.

When $R^{13a}$ is a substituted hydroxyl or substituted thiol group it may be for example a group —OR$^{14}$ or a —SR$^{14}$ or —SC(=NH)NH$_2$ group respectively.

Esterified carboxyl groups represented by the group $R^{13a}$ include groups of formula —CO$_2$Alk$^7$ wherein Alk$^7$ is a group as defined hereinbefore.

When Alk$^6$ is present in or as a substituent it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —S(O)$_2$— or —N(R$^9$)— groups.

Cycloaliphatic or heterocycloaliphatic groups represented by the groups $R^{13a}$ or $R^{14}$ include those optionally substituted $C_{3-10}$cycloaliphatic or $C_{3-10}$ heterocycloaliphatic groups described above for $R^3$.

Aryl or heteroaryl groups represented by the groups $R^{13}$a or $R^{14}$ include mono- or bicyclic optionally substituted $C_{6-12}$ aromatic or $C_{1-9}$ heteroaromatic groups as described above for the group Ar$^1$. The aromatic and heteroaromatic groups may be attached to the remainder of the compound of formula (1) by any carbon or hetero e.g. nitrogen atom as appropriate.

When —NHet$^1$ or -Het$^2$ forms part of a substituent $R^{13}$ each may be for example an optionally substituted pyrrolidinyl, pyrazolidinyl, piperazinyl, morpholinyl, thiomorpholinyl, piperidinyl or thiazolidinyl group. Additionally Het$^2$ may represent for example, an optionally substituted cyclopentyl or cyclohexyl group. Optional substituents which may be present on —NHet$^1$ or -Het$^2$ include those $R^7$ substituents described above.

Particularly useful atoms or groups represented by $R^{13}$ include fluorine, chlorine, bromine or iodine atoms, or $C_{1-6}$alkyl, e.g. methyl, ethyl, n-propyl, i-propyl, n-butyl or t-butyl, optionally substituted phenyl, pyridyl, pyrimidinyl, pyrrolyl, furyl, thiazolyl, thienyl, morpholinyl, thiomorpholinyl, piperazinyl, e.g. t-butyloxycarbonylpiperazinyl, pyrrolidinyl, dioxolanyl, dioxanyl, oxazolidinyl, thiazolidinyl, imidazolidinyl or piperidinyl, $C_{1-6}$hydroxyalkyl, e.g. hydroxymethyl or hydroxyethyl, carboxy$C_{1-6}$alkyl, e.g. carboxyethyl, $C_{1-6}$alkylthio e.g. methylthio or ethylthio, carboxy$C_{1-6}$ alkylthio, e.g. carboxymethylthio, 2-carboxyethylthio or 3-carboxypropylthio, $C_{1-6}$alkoxy, e.g. methoxy or ethoxy, hydroxyC$_{1-6}$alkoxy, e.g. 2-hydroxyethoxy, optionally substituted phenoxy, pyridyloxy, thiazolyoxy, phenylthio or pyridylthio, C$_{4-7}$cycloalkyl, e.g. cyclobutyl, cyclopentyl, C$_{5-7}$cycloalkoxy, e.g. cyclopentyloxy, haloC$_{1-6}$alkyl, e.g. trifluoromethyl, haloC$_{1-6}$alkoxy, e.g. trifluoromethoxy, C$_{1-6}$alkylamino, e.g. methylamino, ethylamino or propylamino, C$_{6-12}$arylC$_{1-6}$alkylamino, e.g. benzylamino, 4-fluorobenzylamino or 4-hydroxyphenylethylamino, amino (—NH$_2$), aminoC$_{1-6}$alkyl, e.g. aminomethyl or aminoethyl, C$_{1-6}$dialkylamino, e.g. dimethylamino or diethylamino, aminoC$_{1-6}$alkylamino, e.g. aminoethylamino or aminopropylamino, optionally substituted Het$^1$NC$_{1-6}$alkylamino, e.g. 3-morpholinopropylamino, C$_{1-6}$alkylaminoC$_{1-6}$alkyl, e.g. ethylaminoethyl, C$_{1-6}$dialkylaminoC$_{1-6}$alkyl, e.g. diethylaminoethyl, aminoC$_{1-6}$alkoxy, e.g. aminoethoxy, C$_{1-6}$alkylaminoC$_{1-6}$alkoxy, e.g. methylaminoethoxy, C$_{1-6}$dialkylaminoC$_{1-6}$alkoxy, e.g. dimethylaminoethoxy, diethylaminoethoxy, diisopropylaminoethoxy, or dimethylaminopropoxy, hydroxyC$_{1-6}$alkylamino, e.g. 2-hydroxyethylamino, 3-hydroxypropylamino or 3-hydroxybutylamino, imido, such as phthalimido or naphthalimido, e.g. 1,8-naphthalimido, nitro, cyano, amidino, hydroxyl (—OH), formyl [HC(O)—], carboxyl (—CO$_2$H), —CO$_2$Alk$^7$ [where Alk$^7$ is as defined above], C$_{1-6}$ alkanoyl e.g. acetyl, propyryl or butyryl, optionally substituted benzoyl, thiol (—SH), thioC$_{1-6}$alkyl, e.g. thiomethyl or thioethyl, —SC(=NH)NH$_2$, sulphonyl (—SO$_3$H), —SO$_3$Alk$^7$, C$_{1-6}$alkylsulphinyl, e.g. methylsulphinyl, ethylsulphinyl or propylsulphinyl, C$_{1-6}$alkylsulphonyl, e.g. methylsulphonyl, ethylsulphonyl or propylsulphonyl, aminosulphonyl (—SO$_2$NH$_2$), C$_{1-6}$alkylaminosulphonyl, e.g. methylaminosulphonyl, ethylaminosulphonyl or propylaminosulphonyl C$_{1-6}$dialkylaminosulphonyl, e.g. dimethylaminosulphonyl or diethylaminosulphonyl, phenylaminosulphonyl, carboxamido (—CONH$_2$), C$_{1-6}$alkylaminocarbonyl, e.g. methylaminocarbonyl, ethylaminocarbonyl or propylaminocarbonyl, C$_{1-6}$dialkylaminocarbonyl, e.g. dimethylaminocarbonyl or diethylaminocarbonyl, aminoC$_{1-6}$alkylaminocarbonyl, e.g. aminoethylaminocarbonyl, C$_{1-6}$alkylaminoC$_{1-6}$alkylaminocarbonyl, e.g. methylaminoethylaminocarbonyl, C$_{1-6}$dialkylaminoC$_{1-6}$alkylaminocarbonyl, e.g. diethylaminoethylaminocarbonyl, aminocarbonylamino, C$_{1-6}$alkylaminocarbonylamino, e.g. methylaminocarbonylamino or ethylaminocarbonylamino, C$_{1-6}$dialkylaminocarbonylamino, e.g. dimethylaminocarbonylamino or diethylaminocarbonylamino, C$_{1-6}$alkylaminocabonylC$_{1-6}$alkylamino, e.g. methylaminocarbonylmethylamino, aminothiocarbonylamino, C$_{1-6}$alkylaminothiocarbonylamino, e.g. methylaminothiocarbonylamino or ethylaminothiocarbonylamino, C$_{1-6}$dialkylaminothiocarbonylamino, e.g. dimethylaminothiocarbonylamino or diethylaminothiocarbonylamino, C$_{1-6}$alkylaminothiocarbonylC$_{1-6}$alkylamino, e.g. ethylaminothiocarbonylmethylamino, —CONHC(=NH)NH$_2$, C$_{1-6}$alkylsulphonylamino, e.g. methylsulphonylamino or ethylsulphonylamino, haloC$_{1-6}$alkylsulphonylamino, e.g. trifluoromethylsulphonylamino, C$_{1-6}$dialkylsulphonylamino, e.g. dimethylsulphonylamino or diethylsulphonylamino, optionally substituted phenylsulphonylamino, aminosulphonylamino (—NHSO$_2$NH$_2$), C$_{1-6}$alkylaminosulphonylamino, e.g. methylaminosulphonylamino or ethylaminosulphonylamino, C$_{1-6}$dialkylaminosulphonylamino, e.g. dimethylaminosulphonylamino or diethylaminosulphonylamino, optionally substituted morpholinesulphonylamino or morpholinesulphonylC$_{1-6}$alkylamino, optionally substituted phenylaminosulphonylamino, C$_{1-6}$alkanoylamino, e.g. acetylamino, aminoC$_{1-6}$alkanoylamino e.g. aminoacetylamino, C$_{1-6}$dialkylaminoC$_{1-6}$alkanoylamino, e.g. dimethylaminoacetylamino, C$_{1-6}$alkanoylaminoC$_{1-6}$alkyl, e.g. acetylaminomethyl, C$_{1-6}$alkanoylaminoC$_{1-8}$alkylamino, e.g. acetamidoethylamino, C$_{1-6}$alkoxycarbonylamino, e.g. methoxycarbonylamino, ethoxycarbonylamino or t-butoxycarbonylamino or optionally substituted benzyloxy, pyridylmethoxy, thiazolylmethoxy, benzyloxycarbonylamino, benzyloxycarbonylaminoC$_{1-6}$alkyl e.g. benzyloxycarbonylaminoethyl, thiobenzyl, pyridylmethylthio or thiazolylmethylthio groups.

Where desired, two R$^{13}$ substituents may be linked together to form a cyclic group such as a cyclic ether, e.g. a C$_{1-6}$alkylenedioxy group such as methylenedioxy or ethylenedioxy.

It will be appreciated that where two or more R$^{13}$ substituents are present, these need not necessarily be the same atoms and/or groups. In general, the substituent(s) may be present at any available ring position in the aromatic or heteroaromatic group represented by R$^3$.

Where desired two R$^z$ substituents attached to a single carbon atom of the ring Cy may be linked together to form an optionally substituted spiro-linked monocyclic C$_{3-7}$cycloaliphatic or C$_{2-7}$heterocycloaliphatic group. C$_{3-7}$cycloaliphatic groups of this type include cyclopropyl, cyclobutyl, cyclopentyl, cyclohexyl, cycloheptyl, cyclopentenyl and cyclohexenyl groups. C$_{2-7}$heterocycloaliphatic groups include pyrrolidinyl, tetrahydrofuranyl, tetrahydropyranyl, piperidinyl, and tetrahydrothiophenyl groups. Optional substituents which may be present on such groups include those optional substituents described hereinbefore in relation to R$^3$ cycloaliphatic and heterocycloaliphatic groups.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isothionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

In the compounds according to the invention the group R$^1$ is preferably an Ar$^1$L$^2$Ar$^2$Alk- group. In compounds of this type Ar$^1$ is preferably an optionally substituted phenyl, monocyclic heteroaromatic or bicyclic heteroaromatic group. Particularly useful monocyclic heteroaromatic groups are optionally substituted five- or six-membered heteroaromatic groups as described previously, especially five- or six-membered heteroaromatic groups containing one or two heteroatoms selected from oxygen, sulphur or nitrogen atoms. Nitrogen-containing groups are especially useful, particularly pyridyl or pyrimidinyl groups. Particularly useful substituents present on these $Ar^1$ groups include halogen atoms or alkyl, haloalkyl, —$OR^5$, —$SR^5$, —$NR^5R^6$, —$CO_2H$, —$CO_2CH_3$, —$NO_2$, —$N(R^5)COR^6$ or —CN groups as described above in relation to the compounds of formula (1). Particularly useful bicyclic heteroaromatic groups represented by $Ar^1$ include optionally substituted ten-membered fused-ring heteroaromatic groups containing one or two heteroatoms, especially nitrogen atoms. Particular examples include optionally substituted naphthyridinyl, especially 2,6-naphthyridinyl and 2,7-naphthyridinyl, quinolinyl and isoquinolinyl, especially isoquinolin-1-yl groups. Particular optional substituents include those just described for monocyclic heteroaromatic groups. In compounds according to the invention the ring Cy is preferably an optionally substituted unsaturated cycloaliphatic or heterocycloaliphatic ring. One particularly useful class of Cy rings is that in which m is the integer 1 and $R^x$ represents an oxo substituent (=O) on a carbon atom adjoined to the group X. A further particularly useful class of Cy rings is that in which m is zero, X is a $C(R^n)$ group and the ring Cy contains an $L^7$ sulfoxide or sulfone heteroatom containing group within its ring structure.

A particularly useful group of compounds according to the invention has the formula (2a):

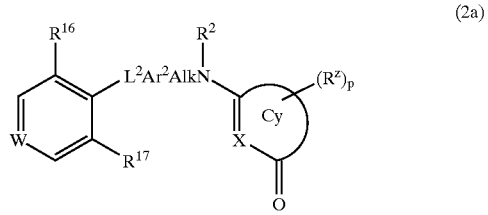

(2a)

wherein —W= is —CH= or —N=;

$R^{16}$ and $R^{17}$, which may be the same or different is each a hydrogen atom or an atom or group -$L^3(Alk^2)_tL^4(R^4)_u$ in which $L^3$, $Alk^2$, t, $L^4$ $R^4$ and u are as defined previously;

$L^2$, $Ar^2$, Alk, $R^2$, Cy, X, $R^z$ and p are as defined for formula (1);

provided that Cy is other than a cyclobutenedione group;

and the salts, solvates, hydrates and N-oxides thereof.

In one particularly useful class of compounds of formula (2a) —W= is a —N= atom.

In another particularly useful class of compounds of formula (2a) —W= is a —CH= group.

$R^{16}$ and $R^{17}$ in compounds of formula (2a) is each preferably as particularly described above for compounds of formula (1), other than a hydrogen atom. Particularly useful $R^{16}$ and $R^{17}$ substituents include halogen atoms, especially fluorine or chlorine atoms, or methyl, halomethyl, especially —$CF_3$, —$CHF_2$ or —$CH_2F$, methoxy or halomethoxy, especially —$OCF_3$, —$OCHF_2$ or —$OCH_2F$ groups.

A further particularly useful group of compounds according to the invention has the formula (2b):

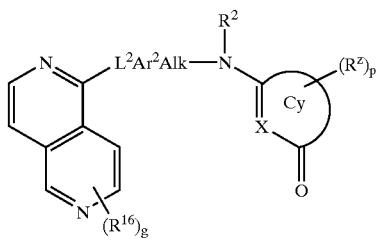

(2b)

wherein $R^{16}$, $L^2$, $Ar^2$, Alk, Cy, $R^2$, X, $R^z$ and p are as defined for formula (2a);

g is the integer 1, 2, 3 or 4.

provided that Cy is other than a cyclobutenedione group;

and the salts, solvates, hydrates and N-oxides thereof.

Each $R^{16}$ atom or group in compounds of formula (2b) may be independently selected from an atom or group -$L^3(Alk^2)_tL^4(R^4)_u$ in which $L^2$, $Alk^2$, t, $L^3$, $R^4$ and u are as previously defined. Particularly useful $R^{16}$ substituents when present in compounds of formula (2b) include halogen atoms, especially fluorine or chlorine atoms, or straight or branched $C_{1-6}$alkyl, especially methyl, ethyl or isopropyl, $C_{3-8}$cycloalkyl especially cyclopropyl, halo$C_{1-6}$alkyl, especially halomethyl, most especially —$CF_3$ or —$CHF_2$, straight of branched $C_{1-6}$alkoxy, especially methoxy or ethoxy, halo$C_{1-6}$alkoxy, especially halomethoxy, most especially —$OCF_3$ or —$OCHF_2$, —$SR^5$ especially methylthio or ethylthio, —CN, —$CO_2Alk^3$, especially —$CO_2CH_3$, —$NO_2$, amino (—$NH_2$), substituted amino (—$NR^5R^6$), —$N(R^5)COR^6$, especially —$NHCOCH_3$, —$COR^5$, especially —$COCH_3$, optionally substituted $C_{6-12}$aromatic, especially optionally substituted phenyl and $C_{1-9}$heteroaromatic groups, especially optionally substituted thienyl, pyridyl and pyrimidinyl groups.

A further particularly useful group of compounds according to the invention has the formula (2c):

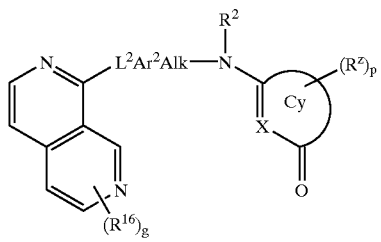

(2c)

wherein $R^{16}$, g, $L^2$, $Ar^2$, Alk, Cy, $R^2$, X, $R^z$ and p are as defined for formula (2b);

provided that Cy is other than a cyclobutenedione group;

and the salts, solvates, hydrates and N-oxides thereof.

Each $R^{16}$ atom or group in compounds of formula (2d) may be independently selected from an atom or group -$L^3(Alk^2)_tL^4(R^4)_u$ as previously defined for compounds of formula (2b).

In one particularly preferred class of compounds of formula (2c) 9 is zero.

In another particularly preferred class of compounds of formula (2c) g is the integer 1 or 2.

An especially preferred class of compounds of formula (2c) is that where g is the integer 1 and $R^{16}$ is a substituent at the 3-position of the 2,7-naphthyridine ring. In this class of compounds $R^{16}$ is most preferably a methyl or halomethyl, especially —CF₃ group, or an optionally substituted phenyl group.

Particularly useful optional substituents which may be present on $R^{16}$ aromatic and heteroaromatic groups when present in compounds of formula (2b) or (2c) include halogen atoms, especially fluorine and chlorine atoms, $C_{1-6}$alkyl groups, especially fluorine and chlorine atoms, $C_{1-6}$alkyl groups, especially methyl, ethyl and i-propyl groups and —CF₃, —OCH₃, —OCH₂CH₃, —OCH(CH₃)₂, —OCF₃, —SCH₃, —NHCH₃, —N(CH₃)₂, —CN, —CO₂CH₃, —COCH₃, and —N(CH₃)COCH₃ groups.

A further particularly useful group of compounds according to the invention has the formula (2d):

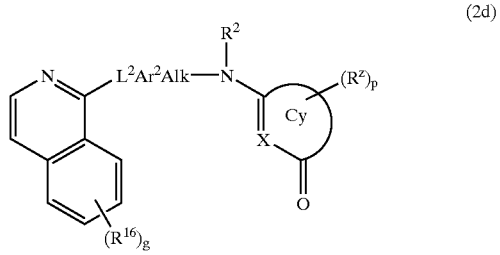

(2d)

wherein $R^{16}$, g, $L^2$, $Ar^2$, Alk, Cy, $R^2$, X, $R^z$ and p are as defined for formula (2b);

provided that Cy is other than a cyclobutenedione group;

and the salts, solvates, hydrates and N-oxides thereof.

Each $R^{16}$ atom or group in compounds of formula (2d) may be independently selected from an atom or group -$L^3(Alk^2)_tL^4(R^4)_u$ as previously defined for compounds of formula (2b).

In one preferred class of compounds of formula (2d) g is zero.

In another preferred class of compounds of formula (2d) g is the integer 1. In this class of compounds $R^{16}$ is preferably a substituent at the 3-positions of the isoquinoline ring as just defined. Most especially useful $R^{16}$ substituents of this type include halogen atoms, especially fluorine and chlorine atoms and straight or branched $C_{1-6}$alkyl groups, especially methyl, ethyl or isopropyl, most especially methyl groups.

In another preferred class of compounds of formula (2d) g is the integer 2 or 3 where one $R^{16}$ group is as just generally and particularly defined, and is located at the 3-position of the isoquinoline ring. In this class of compounds the second and when present third $R^{16}$ optional substituents may be selected from an $R^{16}$ optional substituent as described for compounds of formula (2b) or when g is the integer 3 a $C_{1-6}$alkylenedioxy group, especially a methylenedioxy or ethylenedioxy group. In one particularly useful group of compounds of this class g is the integer 2 where one $R^{16}$ group is at the 3-position of the isoquinoline ring as previously generally and particularly described and the other $R^{16}$ group is at the 6-, 7- or 8-position of the isoquinoline ring, most especially the 7-position. Most especially preferred substituents at the 7-position include a halogen atom, especially a fluorine or chlorine atom, or a $C_{1-6}$alkoxy group, especially a methoxy group.

It will be understood that compounds according to formulae (2a), (2b), (2c) and (2d) include, where applicable, the corresponding hydroxy tautomers.

Alk in compounds of the invention is preferably:

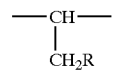

or, especially, —CH₂CH(R)—.

In one preferred class of compounds of formulae (1), (2a), (2b), (2c) and (2d) $R^2$ is a hydrogen atom.

In another preferred class of the compounds of formulae (1), (2a), (2b), (2c) and (2d) R is preferably a —CO₂H group.

In a further preferred class of compounds of formulae (1) and (2) R is an esterified carboxyl group of formula —CO₂Alk⁷. In this class of compound Alk⁷ is preferably a $C_{1-8}$alkyl group, especially a methyl, ethyl, propyl or i-propyl group, an optionally substituted $C_6$-ioaryl group, especially a phenyl group, an optionally substituted $C_{6-10}$aryl$C_{1-6}$alkyl group, especially a benzyl group, a $C_{3-8}$heterocycloalkyl$C_{1-6}$alkyl group, especially a morpholinyl-N-ethyl group or a $C_{1-6}$alkyloxy$C_{1-6}$alkyl group, especially a methyloxyethyl group. Especially preferred esterified carboxyl groups include —CO₂CH₃, —CO₂CH₂CH₃, —CO₂CH₂CH₂CH₃ and —CO₂CH(CH₃)₂ groups.

In general in compounds of formula (2a) when W is a —N= atom, $L^2$ is preferably $L^{2a}$ where $L^{2a}$ is a —CON($R^8$)— group, especially —CONH— or -(Alk$^a$)$L^{2a}$- where -(Alk$^a$)$L^{2a}$- is especially a —CH₂O— group. Most preferred is a —CONH— group.

In general in compounds of formula (2a) when W is a —CH= group $L^2$ is preferably a covalent bond or $L^{2a}$ where $L^{2a}$ is a —CON(R)⁸— group, especially —CONH— or -(Alk$^a$)$L^{2a}$- where -(Alk$^a$)$L^{2a}$- is especially a —CH₂O— group. When W in compounds of formula (2a) is a —CH= group $L^2$ is most preferably a covalent bond.

In general in compounds of formula (2b), (2c) and (2d) $L^2$ is preferably $L^{2a}$ where $L^{2a}$ is an —O— atom or —N($R^8$)— group. An especially useful —N($R^8$)— group is —NH—.

The group $Ar^2$ in compounds of formulae (1), (2a), (2b), (2c) and (2d) is preferably an optionally substituted phenylene group. Particularly useful groups include optionally substituted 1,4-phenylene groups.

The ring Cy in compounds of formulae (1), (2a), (2b), (2c) and (2d) is preferably an optionally substituted cyclopentenyl, cyclohexenyl, cyclohepenyl, dihydropyrimidinyl, dihydropyridinyl or imidazolinyl group, each containing a oxo substituent (=O) within their ring structure on the carbon atom adjoined to the group X.

It will be understood that the corresponding hydroxy (—OH) tautomers of those oxo (=O) containing Cy rings, where the double bond migrates to become part of the Cy ring structure are also included in the definition or preferred Cy rings.

In one preferred class of compounds of formulae (1), (2a), (2b), (2c) and (2d) the group X in the unsaturated heteroaliphatic ring represented by Cy is preferably a N atom. Preferred Cy rings containing this X group include optionally substituted 2-aminopyrimidin4-ones [where amino refers to the group —N($R^2$)—], 4-aminopyrimidin-2-ones, 2-aminopyridin-4-ones, 6-aminopyridin-2-ones and 2-aminoimidazolin-4-ones.

In another preferred class of compounds of formulae (1), (2a), (2b), (2c) and (2d) the group X in the unsaturated cycloaliphatic or heteroaliphatic ring represented by Cy is preferably a C($R^w$) group. Particularly useful $R^w$ atoms and groups that may be present in the group X include hydrogen and halogen atoms, especially fluorine, chlorine or bromine atoms or nitro, $C_{1-6}$alkyl, especially —$CH_3$, —$CH_2CH_3$, —$CH_2CH_2CH_3$, —$(CH_2)_3CH_3$, —$CH(CH_3)_2$, —$C(CH_3)_3$, —$CH(CH_2CH_3)_2$, —$CH_2CH(CH_3)_2$, and —$CH_2C(CH_3)_3$ $C_{2-6}$alkynylene, especially —$CH_2CHCH_2$ and —$CH_2CH_2CHCH_2$, $C_{2-6}$alkylnylene especially —$CH_2CCH$ and —$CH_2CH_2CCH$, optionally substituted $C_{1-6}$alkyl$C_{6-12}$aromatic, especially optionally substituted benzyl or phenylethyl, optionally substituted $C_{6-12}$aromatic, especially optionally substituted phenyl, optionally substituted $C_{3-10}$cycloaliphatic, especially optionally substituted $C_{3-7}$cycloalkyl, most especially optionally substituted cyclopentyl, cyclohexyl or cycloheptyl or optionally substituted $C_{3-10}$heterocycloaliphatic especially $C_{3-7}$heterocycloalkyl, most especially tetrahydropyranyl and tetrahydrothiopyranyl groups. Particularly preferred Cy rings in compounds of formulae (1), (2a), (2b), (2c) and (2d) containing such X groups include optionally substituted 3-amino-2-cyclopenten-1-one [where amino refers to the group —$N(R^2)$—] and 3-amino-2-cyclohexen-1-one rings.

In general in compounds of formula (1), (2a), (2b), (2c) and (2d) p is preferably zero or the integer 1 or 2.

In one preferred class of compounds of formulae (1), (2a), (2b), (2c) and (2d) p is zero or the integer 1 or 2. In this class of compounds Cy is preferably an optionally substituted 3-amino-2-cyclopenten-1-one ring. In one most preferred group of compounds of this class p is zero.

In another preferred class of compounds of formulae (1), (2a), (2b), (2c) and (2d) p is zero or the integer 1 or 2. In this class of compounds Cy is preferably an optionally substituted 3-amino-2-cyclohexen-1-one ring.

In general in compounds of formulae (1), (2a), (2b), (2c) and (2d) when v and n in the group $R^z$ are zero or the integer 1 the group $R^3$ may especially be an optionally substituted heteroaliphatic, cycloaliphatic, heterocycloaliphatic, aromatic or heteroaromatic group as defined herein. Particularly useful groups of this type include optionally substituted $C_{2-6}$heteroalkyl, particularly $C_{1-3}$alkoxy$C_{1-3}$alkyl, especially methoxypropyl, optionally substituted $C_{3-7}$cycloalkyl, especially optionally substituted cyclopropyl, cyclobutyl cyclopropyl or cyclohexyl, optionally substituted $C_{5-7}$heterocycloaliphatic, optionally substituted pyrrolidinyl or thiazolidinyl, optionally substituted phenyl and optionally substituted $C_{5-7}$heteroaromatic, especially optionally substituted pyridyl groups. Optional substituents on these groups include in particular $R^{13}$ atoms or groups where the group is an aromatic or heteroaromatic group and -$(L^8)_p(Alk^5)_qR^{12}$ groups as described earlier where the group is a nitrogen-containing heterocycloaliphatic group such as a pyrrolidinyl or thiazolidinyl group. Particularly useful -$(L^6)_p(Alk^5)_qR^{12}$ groups include those in which $L^6$ is a —CO— group. $Alk^5$ in these groups is preferably present (i.e. q is preferably an integer 1) and in particular is a —$CH_2$— chain. Compounds of this type in which $R^{12}$ is a hydrogen atom or an optionally substituted aromatic or heteroaromatic group, especially an optionally substituted phenyl, pyridyl or imidazolyl group are particularly preferred.

In another preferred class of compounds of formulae (1), (2a), (2b), (2c) and (2d) v is zero, $Alk^1$ in the group $R^z$ is present as an optionally substituted aliphatic chain as defined herein (i.e. n is the integer 1) and $R^3$ is a hydrogen atom. Compounds of this type where -$Alk^1R^3$ is an optionally substituted $C_{1-6}$alkyl group, particularly a methyl, ethyl, n-propyl i-propyl, i-butyl, t-butyl or n-butyl group or an allyl (—$CH_2CHCH_2$) or (propargyl) —$CH_2CCH$ group are especially useful. In one preferred group of compounds of this type $L^1$ is a covalent bond. In another preferred group of compounds of this type $L^1$ is a group —$N(R^8)$— as previously generally and particularly defined.

Particularly preferred optional substituents which may be present on aliphatic groups of formula -$Alk^1R^3$ include one, two, three or more halogen atoms, esepcially fluorine, chlorine or bromine atoms or $C_{1-6}$alkoxy groups e.g. methoxy or ethoxy, halo$C_{1-6}$alkoxy groups e.g. —$OCF_3$, substituted amino groups e.g. —$NHCH_3$ or —$N(CH_3)_2$ or —$COR^9$ groups e.g. —$COCH_3$ or carboxyl (—$CO_2H$) or esterified carboxyl e.g. —$CO_2CH_3$ or $C_{02}C(CH_3)_2$ groups.

In one most preferred class of compounds of formulae (1), (2a), (2b), (2c) and (2d) p is the integer 1 and $R^z$ is an optionally substituted aliphatic group -$Alk^1R^3$ as just defined.

In another preferred class of compounds of formulae (1), (2a), (2b), (2c) and (2d) p is the integer 2 and $R^z$ is an optionally substituted aliphatic group -$Alk^1R^3$ as just defined. Most preferably the $R^z$ groups are identical and especially preferred is the case where the $R^z$ groups are each attached to the same carbon atom of the Cy ring.

In another preferred class of compounds of formulae (1), (2a), (2b), (2c) and (2d) p is the integer 2 and two $R^z$ groups are joined to form a spiro-linked optionally substituted cycloaliphatic group (both $R^z$ groups joined to a single carbon atom of Cy). Especially preferred optionally substituted cycloaliphatic groups of this type include spiro-fused cyclopentyl and cyclohexyl groups. Particularly preferred optional substituents which may be present on such groups include those just described in relation to —$Ak$ $^1R^3$.

A further paticularly useful group of compounds according to the invention has the formula (2e):

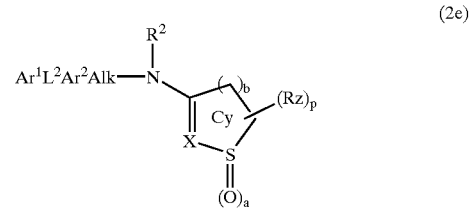

(2e)

wherein:

$Ar^1$ is an aromatic or heteroaromatic group of formula

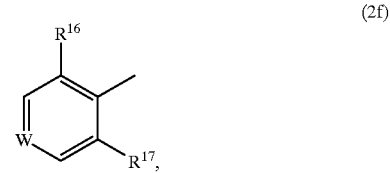

(2f)

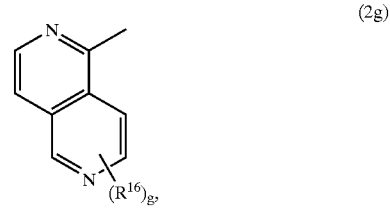

(2g)

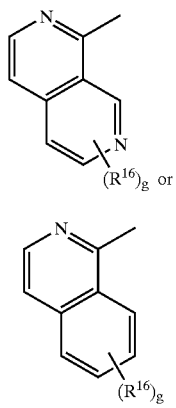

(2h)

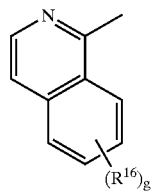

(2i)

in which W, $R^{16}$, $R^{17}$ and g are as previously defined for formula (1);
a is the integer 1 or 2;
b is the integer 1, 2 or 3;
X is a group $C(R^w)$;
and the salts, solvates, hydrates and N-oxides thereof.

In compounds of formula (2e) where $Ar^1$ is an aromatic group of formula (2f) W, $R^{16}$, $R^{17}$ and $L^2$ are in partiuclar atoms or groups as particularly described in relation to compounds of formula (2a) hereinbefore.

In compounds of formula (2e) where $Ar^1$ is a heteroaromatic group of formula (2g, (2h) or (2i) $R^{16}$, g and $L^2$ are in particular atoms or groups as partciularly described in relation to compounds of formula (2b), (2c) and (2d) respectively.

In compounds of formula (2e), $Ar^2$, Alk, $R^2$ and R are in particular atoms or groups as particularly described in relation to compounds of formula (2a).

In one particularly preferred class of compounds of formula (2e) a is the integer 1.

In a most particularly preferred class of compounds of formula (2e) a is the integer 2.

In a further particularly preferred class of compound of formula (2e) b is the integer 1.

In compounds of formula (2e) $R^w$ is preferably an atom or group as generally and particularly described hereinbefore in relation to compounds of formula (2a).

In one preferred class of compounds of formula (2e) p is the integer 1 and $R^z$ is an aliphatic chain $-Alk^1R^3$ as particularly described in relation to compounds of formula (2a).

In another preferred class of compounds of formula (2e) p is the integer 2 and $R^2$ is an aliphatic chain $-Alk^1R^2$ or spiro-linked cycloaliphatic group as particularly described in relation to compounds of formula (2a).

Particularly useful compounds of the invention include:
(S)-3-[4-[(2,6-Naphthyridinyl)amino]phenyl]-2-[(2-(1-ethylpropyl)-3-oxo-1-cyclopentenyl)amino]propionic acid;
(S)-3-[4-[(3-Methyl-2,7-naphthyridinyl)oxy]phenyl]-2-[(2-propyl-3-oxo-1-cyclopentenyl)amino]propionic acid;
(S)-3-[(4-[3-Methyl-2,7-naphthyridinyl]oxy)phenyl]-2-[(2-isobutyl-3-oxo-1-cyclopentenyl)amino]propionic acid;
(S)-3-[(4-(2,7-Naphthyridin-1-yl)oxy)phenyl]-2-[(2-isobutyl-3-oxo-1-cyclopentenyl)amino]propionic acid;
(S)-3-[4-[(3,5-Dichloropyrid-4-yl)carboxamido)phenyl]-2-[(2-isobutyl-3-oxo-1-cyclopentenyl)amino]propionic acid;
(S)-3-[4-[(3-Methyl-2,7-naphthyridin-1-yl)amino]phenyl]-2-((2-isobutyl-3-oxo-1-cyclopentenyl)amino]propionic acid;
(S)-3-[4-(-2',6'-Dimethoxy)biphenyl]-2-[(2-isobutyl-3-oxo-1-cyclo-pentenyl)amino]propionic acid;
(2S)-3-[4-(2,6-Naphthyridin-1-yl)amino)phenyl]-2-[(2-isobutyl-3-oxo-1-cyclopentenyl)amino]propionate;
(2S)-3-[4-(2,6-Naphthyridin-1-yl)amino)phenyl]-2-[(2-isopropyl-3-oxo-1-cyclopentenyl)amino]propionic acid
(2S)-3-[4-(2,6-Naphthyridin-1-yl)amino)phenyl]-2-[(2-allyl-3-oxo-1-cyclopentenyl)amino]propionate;
(2S)-3-[4-(2,6-Naphthyridin-1-yl)amino)phenyl]-2-[(2-propyl-3-oxo-1-cyclopentenyl)amino]propionate;
and the salts, solvates, hydrates and N-oxides and carboxylic acid ester, particularly methyl, ethyl, propyl and i-propyl esters thereof.

Compounds according to the invention are potent and selective inhibitors of α4 integrins. The ability of the compounds to act in this way may be simply determined by employing tests such as those described in the Examples hereinafter.

The compounds are of use in modulating cell adhesion and in particular are of use in the prophylaxis and treatment of diseases or disorders including inflammation in which the extravasculation of leukocytes plays a role and the invention extends to such a use and to the use of the compounds for the manufacture of a medicament for treating such diseases or disorders, Diseases or disorders of this type include inflammatory arthritis such as rheumatoid arthritis vasculitis or polydermatomyositis, multiple sclerosis, allograft rejection, diabetes, inflammatory dermatoses such as psoriasis or dermatitis, asthma and inflammatory bowel disease.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline ellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols $Ar^1$, $Ar^2$, Alk, $R^1$, $R^2$, $R^3$, $L^1$, $L^2$, $Alk^1$, Cy, X, $R^x$, m, $R^z$, p, $R^w$ and n when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1999]. In some instances, deprotection may be the final step in the synthesis of a compound of formula (1) and the processes according to the invention described hereinafter are to be understood to extend to such removal of protecting groups. For convenience the processes described below all refer to a preparation of a compound of formula (1) but clearly the description applies equally to the preparation of compounds of formula (2).

Thus according to a further aspect of the invention, a compound of formula (1) in which R is a —$CO_2H$ group may be obtained by hydrolysis of an ester of formula (3):

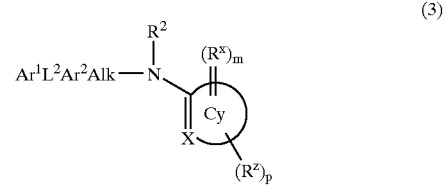

(3)

where Alk represents a group

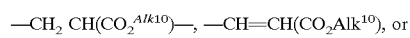

, or

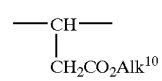

[where $Alk^{10}$ is an alkyl group, for example a $C_{1-6}$alkyl group]

The hydrolysis may be performed using either an acid or a base depending on the nature of $Alk^{10}$, for example an organic acid such as trifluoroacetic acid or an inorganic base such as lithium, sodium or potassium hydroxide optionally in an aqueous organic solvent such as an amide e.g. a substituted amide such as dimethylformamide, an ether e.g. a cyclic ether such as tetrahydrofuran or dioxane or an alcohol e.g. methanol at a temperature from ambient to the reflux temperature. Where desired, mixtures of such solvents may be used.

According to a further aspect of the invention a compound of formula (1) ay be prepared by condensation of a compound of formula (4):

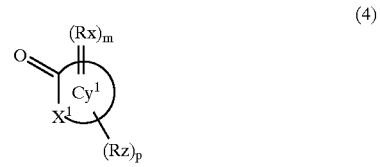

(4)

where $Cy^1$ is a cycloaliphatic or heterocycloaliphatic ring in which the double bond of the Cy ring of compounds of formula (1) is replaced by a single bond and an oxo (=O) substituent is attached to the carbon atom to which $R^1R^2N$— will subsequently be joined and $X^1$ is a CH($R^w$) or NH group, with an amine $R^1R^2NH$ or a salt thereof.

The reaction may be performed in an inert solvent or mixture of solvents, for example a hydrocarbon such as an aromatic hydrocarbon e.g. benzene or toluene and/or a halogenated hydrocarbon such as 1,2-dichloroethane, at a temperature from 0° C. to the reflux temperature. Where necessary, for example when a salt of an amine $R^1R^2NH$ is used, an organic base such as diisopropylethylamine can be added.

Any carboxylic acid group present in the intermediate of formula (4) or the amine $R^1R^2NH$ may need to be protected during the displacement reaction, for example as an ethyl ester. The desired acid may then be obtained through subsequent hydrolysis, for example as particularly described above and generally described below.

A compound of formula (1) may also be prepared by displacement of a leaving group from a compound of formula (5):

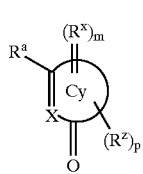

(5)

where $R^a$ is a leaving group, with an amine $R^1R^2NH$ or a salt thereof. Suitable leaving groups represented by $R^a$ include a halogen atom especially a chlorine, bromine or iodine atom, or alkoxy e.g. methoxy or ethoxy or isopropyloxy, alkylthio e.g. methylthio or ethylthio, alkylsulphoxide e.g. methylsulphoxide, aryloxy e.g. dinitrophenyloxy or araalkoxy e.g. benzyloxy group.

The reaction may be performed in an inert solvent or mixture of solvents for example a substituted amide such as dimethylformamide, or alcohol such as methanol or ethanol and/or a halogenated hydrocarbon such as dichloromethane, at a temperature from 0° C. to the reflux temperature. Where necessary, for example when the salt of an amine $R^1R^2NH$ is used an organic base such as diisopropylethylamine can be added.

Where desired the displacement reaction may also be performed on an intermediate of formulae (4) or (5) or $R^1R^2NH$ which is linked, for example via its $R^1$ or $R^3$ group, to a solid support, such as a polystyrene resin. After the reaction the desired compound of formula (1) may be displaced from the support by any convenient method, depending on the original linkage chosen.

Intermediates of formulae (4), (5) and $R^1R^2NH$ may be obtained from simpler, known compounds by one or more standard synthetic methods employing substitution, oxidation, reduction or cleavage reactions. Particular substitution approaches include conventional alkylation, arylation, heteroarylation, acylation, thioacylation, halogenation, sulphonylation, nitration, formylation and coupling procedures. It will be appreciated that these methods may also be used to obtain or modify other compounds of formulae (1) and (2) where appropriate functional groups exist in these compounds.

Thus compounds of the invention and intermediates thereto may be prepared by alkylation, arylation or heteroarylation. For example, compounds containing a -$L^1$H or -$L^2$H group (where $L^1$ and $L^2$ is each a linker atom or group) may be treated with a coupling agent $R^3(Alk^1)_nX^1$ or $Ar^1X^1$ respectively in which $X^1$ is a leaving atom or group such as a halogen atom, e.g. a fluorine, bromine, iodine or chlorine atom or a sulphonyloxy group such as an alkylsulphonyloxy, e.g. trifluoromethylsulphonyloxy or arylsulphonyloxy, e.g. p-toluenesulphonyloxy group.

The reaction may be carried out in the presence of a base such as a carbonate, e.g. caesium or potassium carbonate, an alkoxide, e.g. potassium t-butoxide, or a hydride, e.g. sodium hydride, or an organic amine e.g. triethylamine or N,N-diisopropylethylamine or a cyclic amine, such as N-methylmorpholine or pyridine, in a dipolar aprotic solvent such as an amide, e.g. a substituted amide such as dimethylformamide or an ether, e.g. a cyclic ether such as tetrahydrofuran.

Compounds of formula $Ar^1X^1$ may be prepared from alcohols of formula $Ar^1OH$ by reaction with a halogenating agent, for example a phosphorous oxyhalide such as phosphorous oxychloride at an elevated temperature e.g. 110° C.

Intermediate alcohols of formula $Ar^1OH$ in which, for example, $Ar^1$ represents a 2,6-naphthyridine may be prepared by methods well known to a person skilled in the art, e.g. by the method of Sakamoto, T. et al [Chem. Pharm. Bull. 33, 626–633, (1985)].

Alternatively alkylating agents of formula $Ar^1X^1$ in which, for example, $Ar^1$ represents a 2,6-naphthyridine may be prepared by reaction of a 2,6-naphthyridine N-oxide or N,N'-dioxide with a halogenating agent, e.g. a phosphorous oxyhalide such as phosphorous oxychloride to give a 1-halo or 1,5-dihalo-2,6-napthyridine respectively. In the case of 1,5-dihalo-2,6-napthyridines each halogen atom may be substituted separately by a reagent such as $HL^2Ar^2AlkN(R^2)H$ or $HL^3(Alk^2)_tL^4(R^4)_u$ by the particular methods just described above.

2,6-Napthyridine N-oxides and N,N'-dioxides may be generated from the corresponding 2,6-napthyridines by the general methods of synthesis of N-oxides described below or they may be synthesised by the methods of Numata, A. et al (Synthesis, 1999, 306–311).

Further alkylating agents of formula $Ar^1X^1$ in which, for example, $Ar^1$ represents a 2,6-naphthyridine, may be prepared by the methods of Giacomello G. et al [Tetrahedron Letters, 1117–1121 (1965)], Tan, R. and Taurins, A. [Tetrahedron Lett., 2737–2744, (1965)], Ames, D. E. and Dodds, W. D. [J. Chem. Soc. Perkin 1, 705–710 (1972)] and Alhaique, F. et al [Tetrahedron Lett., 173–174 (1975)].

Intermediate alcohols of formula $Ar^1OH$ in which $Ar^1$ represents an optionally substituted 2,7-naphthyridin-1-yl group may be prepared by methods well known to a person skilled in the art, e.g. by the method of Sakamoto, T. et al [Chem. Pharm. Bull. 33, 626–633, (1985)] or Baldwin, J, J. et al [J. Org. Chem, 43, 4878–4880, (1978)]. Thus for example the method of Baldwin may be modified to allow the synthesis of intermediate 3-substituted 2,7-naphthyridin-1-yl groups of formula $Ar^1OH$ as depicted in Scheme 1:

Scheme 1

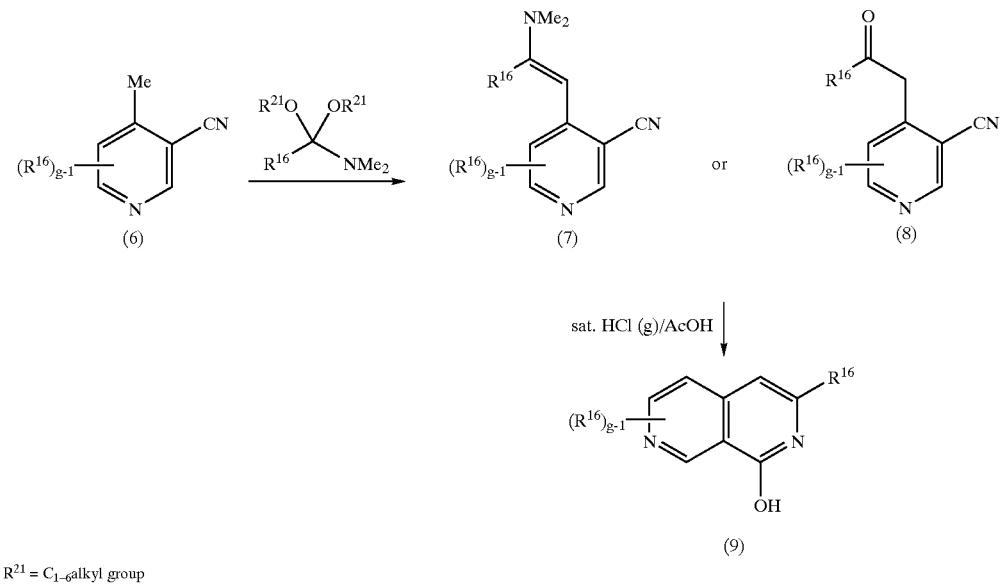

$R^{21} = C_{1-6}$alkyl group

Reaction of an optionally substituted 4-methyl-3-cyano pyridine of formula (6) with a N,N-dimethylformamide di-$C_{1-6}$alkyl acetal, e.g. N,N-dimethylformamide diethyl acetal, in a dipolar solvent such as an amide e.g. a substituted amide such as dimethylformamide at an elevated temperature e.g. 140–150° gives a compound of formula (7) or (8) or a mixture thereof depending on the nature of the group $R^{16}$.

Compounds of formula (7) or (8) may be cyclised to 3-substituted 2,7-naphthyridin-1-yl alcohol of formula (9) by treatment with an acid e.g. an inorganic acid such as hydrochloric acid or hydrobromic acid or an acidic gas such as hydrogen chloride gas in an organic solvent e.g. an organic acid such as acetic acid optionally in the presence of water at a temperature from about ambient to 50° C.

Alternatively alkylating agents of formula $Ar^1X^1$ in which $Ar^1$ represents an optionally substituted 2,7-naphthyridin-yl group may be prepared by reaction of a 2,7-naphthyridine N-oxide or N,N'-dioxide with a halogenating agent, e.g. a phosphorous oxyhalide such as phosphorous oxychloride to give a 1-halo or 1,6-dihalo- and/or-1,8-dihalo-2,7-napthyridine respectively. In the case of 1,6-dihalo- and/or 1,8-dialo-2,6-napthyridines each halogen atom may be substituted separately by a reagent such as $HL^2Ar^2AlkN(R^2)H$ or $HL^3(Alk^2)_rL^4(R^4)_u$ by the particular methods just described above.

2,7-Napthyridine N-oxides and N,N'-dioxides may be generated from the corresponding 2,7-naphthyridines by the general methods of synthesis of N-oxides described below or they may be synthesised by the methods of Numata, A. et al (Synthesis, 1999, 306–311).

Further alkylating agents of formula $Ar^1X^1$ in which, for example, $Ar^1$ represents a 2,7-naphthyridin-1-yl, may be prepared by the methods of Wenkert E. et al J. Am. Chem. Soc. 89, 6741–5 (1967), and Aust. J. Chem. 433 (1972), and Sheffield D. J. J. Chem. Soc. Perkin. Trans I, 2506 (1972).

Intermediate alcohols of formula $Ar^1OH$ in which $Ar^1$ represents a 3-substituted isoquinolin-1-yl group may be prepared by methods well known to a person skilled in the art, e.g. by the methods of Wu M.-J. et al Tetrahedron, 55, 13193–200 (1999), Hiebl J. et al Tetrahedron Lett. 40, 7935–8 (1999), Nagarajan A. et al Indian J. Chem., Sect. B, 28B, 67–78 (1989), Brun E. M. et al Synlett, 7, 1088–90 (1999) and Brun, E. M. et al Synthesis, 273–280 (2000).

Further alkylating agents of formula $Ar^1X^1$ in which, for example, $Ar^1$ represents a isoquinolin-1-yl group, may be prepared by the methods of Falk H. et al Monatsch. Chem. 25, 325–33 (1994), and Deady, L. W. et al Aust. J. Chem 42, 1029–34 (1989).

In a further example intermediates of formula $R^1R^2NH$ may be obtained by reaction of a compound of formula $Ar^1L^2H$ with a compound of formula $X^1Ar^2AlkN(R^2)H$ under the reaction conditions just described.

Compounds of formula $Ar^1L^2H$ in which, for example $Ar^1$ represents a 2,6-naphthyridine and $L^2$ is a —$N(R^8)$— group, may be prepared from substituted 4-cyano-3-cyanomethylpyridines by the methods of Alhaique, F. et al (ibid and Gazz. Chim. Ital. 1975, 105, 1001–1009) or from 3-fomylpyridines by the methods of Molina, P. at al (Tetrahedron 1992, 48, 4601–4616).

Compounds of formula $Ar^1L^2H$ in which, for example $Ar^1$ represents a 2,7-naphthyridin-1-yl group and $L^2$ is a —$N(R^8)$— group, may be prepared from substituted 4-formylpyridines by the methods of Molina, P. et al Tetrahedron, 48, 4601–4616, (1992), or by the methods described in U.S. Pat. No. 3,938,367.

Compounds of formula $Ar^1L^2H$ in which, for example $Ar^1$ represents a 3-substituted isoquinolin-1-yl group and $L^2$ is a —$N(R^8)$— group, may be prepared by the methods of Bordner, J. et al J. Med. Chem. 31, 1036–9 (1988), Tovar J. D. et al J. Org. Chem., 64, 6499–6504 (1999), Karser E. M. et al Synthesis, 11, 805–6 (1974), and Molino, P et al J. Chem. Soc. Perkin Trans. 1 1727–31 (1990).

In another example, compounds containing a -$L^1$ H or -$L^2$H or group as defined above may be functionalised by acylation or thioacylation, for example by reaction with one of the alkylating agents just described but in which $X^1$ is replaced by a —$C(O)X^2$, —$C(S)X^2$, —$N(R^8)COX^2$ or —$N(R^8)C(S)X^2$ group in which $X^2$ is a leaving atom or group as described for $X^1$. The reaction may be performed in the presence of a base, such as a hydride, e.g. sodium hydride or an amine, e.g. triethylamine or N-methylmorpholine, in a solvent such as a halogenated hydrocarbon, e.g. dichloromethane or carbon tetrachloride or an amide, e.g. dimethylformamide, at for example ambient temperature. Alternatively, the acylation may be carried out under the same conditions with an acid (for example one of the alkylating agents described above in which $X^1$ is replaced by a —$CO_2H$ group) in the presence of a condensing agent, for example a diimide such as 1-(3-dimethylaminopropyl)-3-ethylcarbodiimide or N,N'-dicyclohexylcarbodiimide, advantageously in the presence of a catalyst such as a N-hydroxy compound e.g. a N-hydroxytriazole such as 1-hydroxybenzotriazole. Alternatively the acid may be reacted with a chloroformate, for example ethylchloroformate, prior to the desired acylation reaction.

In a further example compounds may be obtained by sulphonylation of a compound containing an —OH group by reaction with one of the above alkylating agents but in which $X^1$ is replaced by a —S(O)Hal or —$SO_2Hal$ group [in which Hal is a halogen atom such as chlorine atom] in the presence of a base, for example an inorganic base such as sodium hydride in a solvent such as an amide, e.g. a substituted amide such as dimethylformamide at for example ambient temperature.

In another example, compounds containing a -$L^1$ H or -$L^2$H group as defined above may be coupled with one of the alkylation agents just described but in which $X^1$ is replaced by an —OH group in a solvent such as tetrahydrofuran in the presence of a phosphine, e.g. triphenylphosphine and an activator such as diethyl, diisopropyl- or dimethylazodicarboxylate.

In a further example, ester groups —$CO_2R^5$, —$CO_2R^{11}$ or —$CO_2Alk^7$ in the compounds may be converted to the corresponding acid [—$CO_2H$] by acid- or base-catalysed hydrolysis depending on the nature of the groups $R^5$, $R^{11}$ or $Alk^7$. Acid- or base-catalysed hydrolysis may be achieved for example by treatment with an organic or inorganic acid, e.g. trifluoroacetic acid in an aqueous solvent or a mineral acid such as hydrochloric acid in a solvent such as dioxan or an alkali met al hydroxide, e.g. lithium hydroxide in an aqueous alcohol, e.g. aqueous methanol.

In a further example, —$OR^5$ or —$OR^{14}$ groups [where $R^5$ or $R^{14}$ each represents an alkyl group such as methyl group] in compounds of formula (1) may be cleaved to the corresponding alcohol —OH by reaction with boron tribromide in a solvent such as a halogenated hydrocarbon, e.g. dichloromethane at a low temperature, e.g. around –78° C.

Alcohol [—OH] groups may also be obtained by hydrogenation of a corresponding —$OCH_2R^{14}$ group (where $R^{14}$ is an aryl group) using a met al catalyst, for example palladium on a support such as carbon in a solvent such as ethanol in the presence of ammonium formate, cyclohexadiene or hydrogen, from around ambient to the reflux temperature. In another example, —OH groups may be generated from the corresponding ester [$CO_2Alk^7$ or $CO_2R^5$] or aldehyde [—CHO] by reduction, using for example a complex met al hydride such as lithium aluminium hydride or sodium borohydride in a solvent such as methanol.

In another example, alcohol —OH groups in the compounds may be converted to a corresponding —$OR^5$ or —$OR^{14}$ group by coupling with a reagent $R^5OH$ or $R^{14}OH$ in a solvent such as tetrahydrofuran in the presence of a phosphine, e.g. triphenylphosphine and an activator such as diethyl-, diisopropyl-, or dimethylazodicarboxylate.

Aminosulphonylamino [—$NHSO_2NHR^3$ or —$NHSO_2NHAr^1$] groups in the compounds may be obtained, in another example, by reaction of a corresponding amine [—$NH_2$] with a sulphamide $R^3NHSO_2NH_2$ or $Ar^1NHSO_2NH_2$ in the presence of an organic base such as pyridine at an elevated temperature, e.g. the reflux temperature.

In another example compounds containing a —$NHCSAr^1$, —$CSNHAr^1$, —$NHCSR^3$ or —$CSNHR^3$ may be prepared by treating a corresponding compound containing a —$NHCOAr^1$, —$CONHAr^1$, —$NHCOR^3$ or —$CONHR^3$ group with a thiation reagent, such as Lawesson's Reagent, in an anhydrous solvent, for example a cyclic ether such as tetrahydrofuran, at an elevated temperature such as the reflux temperature.

In a further example amine (—$NH_2$) groups may be alkylated using a reductive alkylation process employing an aldehyde and a borohydride, for example sodium triacetoxyborohyride or sodium cyanoborohydride, in a solvent such as a halogenated hydrocarbon, e.g. dichloromethane, a ketone such as acetone, or an alcohol, e.g. ethanol, where necessary in the presence of an acid such as acetic acid at around ambient temperature.

In a further example, amine [—$NH_2$] groups in compounds of formula (1) may be obtained by hydrolysis from a corresponding imide by reaction with hydrazine in a solvent such as an alcohol, e.g. ethanol at ambient temperature.

In another example, a nitro [—$NO_2$] group may be reduced to an amine [—$NH_2$], for example by catalytic hydrogenation using for example hydrogen in the presence of a met al catalyst, for example palladium on a support such as carbon in a solvent such as an ether, e.g. tetrahydrofuran or an alcohol e.g. methanol, or by chemical reduction using for example a met al, e.g. tin or iron, in the presence of an acid such as hydrochloric acid.

Aromatic halogen substituents in the compounds may be subjected to halogen-met al exchange with a base, for example a lithium base such as n-butyl or t-butyl lithium, optionally at a low temperature, e.g. around –78° C., in a solvent such as tetrahydrofuran and then quenched with an electrophile to introduce a desired substituent. Thus, for example, a formyl group may be introduced by using dimethylformamide as the electrophile; a thiomethyl group may be introduced by using dimethyidisulphide as the electrophile.

In another example, sulphur atoms in the compounds, for example when present in a linker group $L^1$ or $L^2$ may be oxidised to the corresponding sulphoxide or sulphone using an oxidising agent such as a peroxy acid, e.g. 3-chloroperoxybenzoic acid, in an inert solvent such as a halogenated hydrocarbon, e.g. dichloromethane, at around ambient temperature.

In another example compounds of formula $Ar^1X^1$ (where $X^1$ is a halogen atom such as a chlorine, bromine or iodine atom) may be converted to such compounds as $Ar^1CO_2R^{20}$ (in which $R^{20}$ is an optionally substituted alkyl, aryl or heteroaryl group), $Ar^1CHO$, $Ar^1CHCHR^{20}$, $Ar^1CCR^{20}$, $Ar^1N(R^{20})H$, $Ar^1N(R^{20})_2$, for use in the synthesis of for example compounds of formula $Ar^1L^2Ar^2AlkN(R^2)H$, using such well know and commonly used palladium mediated reaction conditions as are to be found in the general reference texts *Rodd's Chemistry of Carbon Compounds*, Volumes 1–15 and Supplementals (Elsevier Science Publishers, 1989), *Fieser and Fieser's Reagents for Organic Synthesis*, Volumes 1–19 (John Wiley and Sons, 1999), *Comprehensive Heterocyclic Chemistry*, Ed. Katritzky et al, Volumes 18, 1984 and Volumes 1–11, 1994 (Pergamon), *Comprehensive Organic Functional Group Transformations*, Ed. Katritzky et al, Volumes 1–7, 1995 (Pergamon), *Comprehensive Organic Synthesis*, Ed. Trost and Flemming, Volumes 1–9, (Pergamon, 1991), *Encyclopedia of Reagents for Organic Synthesis*, Ed. Paquette, Volumes 1–8 (John Wiley and Sons, 1995), *Larock's Comprehensive Organic Transformations* (VCH Publishers Inc., 1989) and *March's Advanced Organic Chemistry* (John Wiley and Sons, 1992).

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate base in a suitable solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral base. The diastereomers may then be separated by any convenient means, for example by crystallisation and the desired enantiomer recovered, e.g. by treatment with an acid in the instance where the diastereomer is a salt.

In another resolution process a racemate of formula (1) may be separated using chiral High Performance Liquid Chromatography. Alternatively, if desired a particular enantiomer may be obtained by using an appropriate chiral intermediate in one of the processes described above.

Chromatography, recrystallisation and other conventional separation procedures may also be used with intermediates or final products where it is desired to obtain a particular geometric isomer of the invention.

The following Examples illustrate the invention. All temperatures are in ° C. The following abbreviations are used:

NMM — N-methylmorpholine;
EtOAc — ethyl acetate;
MeOH — methanol;
BOC — butoxycarbonyl;
DCM — dichloromethane;
AcOH — acetic acid;
DIPEA — diisopropylethylamine;
EtOH — ethanol;
Pyr — pyridine;
Ar — aryl;
DMSO — dimethylsulphoxide;
iPr — isopropyl;
$Et_2O$ — diethylether;
Me — methyl;
THF — tetrahydrofuran;
DMF — N,N-dimethylformamide;
FMOC — 9-fluorenylmethoxycarbonyl;
DBU — 1,8-diazabicyclo[5,4,0]undec-7-ene All NMR's were obtained at 300 MHz and 400 MHz.

INTERMEDIATE 1

2-Benzyl-1,3-cyclopentanedione

To a suspension of 1,3-cyclopentanedione (500 mg, 5.10 mmol) and anhydrous lithium iodide (750 mg, 5.61 mmol) in acetonitrile (10 ml) was added DBU. After 30 min benzyl bromide (1.74 g, 10.2 mmol) was added and the reaction heated for 24 h at reflux. The reaction was poured into water (40 ml), extracted with EtOAc (4×50 ml), dried ($MgSO_4$), the solution concentrated in vacuo and the residue purified by chromatography ($SiO_2$; EtOAc) to give the title compound as an off white solid (222 mg, 23%). δ H ($CD_3OD$) 7.20 (4H, d), 7.10 (1H, m), 3.41 (2H, s), 2.52 (4H, s). m/z (ESI, 70V) 189 ($MH^+$).

INTERMEDIATE 2

2-Allyl-1,3-cyclopentanedione

Prepared in a similar manner to Intermediate 1, from 1,3-cyclopentanedione and alkyl bromide, heating to reflux for 3 days to give the title compound as an refluxing for 3d with allyl bromide off-white solid (115 mg, 8%). δ H ($CD_3OD$) 5.80 (1H, m), 5.00–4.80 (2H, 3×m), 2.85 (2H, d), 2.48 (4H, s). m/z (ESI, 70V) 139 ($MH^+$).

INTERMEDIATE 3

2-Butyl-1,3-cyclopentanedione

To a suspension of cyclopent-4-ene-1,3-dione (1.22 g, 12.6 mmol) in acetic anhydride (4 ml) were added ethyl orthobutyrate (3.74 g, 25.3 mmol) and anhydrous $ZnCl_2$. The reaction was heated at 80° for 24 h, solid removed by filtration, the filtrate concentrated in vacuo and the residues purified by chromatography ($SiO_2$; 70:30 hexane/EtOAc) to give 2-(α-methoxypropylidene)cyclopent-4-ene-1,3-dione as a brown oil. δ H ($CDCl_3$) 6.88 (2H, s), 4.07 (3H, s), 3.00 (2H, t), 1.63 (2H, m), 1.08 (3H, t). m/z (ESI, 70V) 181 ($MH^+$).

A solution of this oil (EtOH, 11 ml) was subjected to catalytic (Pd/C, 200 mg) hydrogenation for 24 h, filtered, the solution concentrated in vacuo, and the residue purified by chromatography ($SiO_2$; EtOAc) to give the title compound as a white, waxy solid (494 mg, 25%). δ H ($CD_3OD$) 2.46 (4H, s), 2.09 (2H, t, J 7.3 Hz), 1.33 (4H, m), 0.89 (3H, t, J 9.5 Hz). m/z (ESI, 70V) 155 ($MH^+$).

INTERMEDIATE 4

2-Phenyl-1,3-Cyclopentanedione

To a solution of $BF_3.OEt_2$ (1.3 g, 9.2 mmol) and benzaldehyde diemethylacet al (1.0 g, 6.6 mmol) in DCM (5 ml) under $N_2$ at −78° was added a solution of 1,2-bistrimethylsilyloxycyclobutene (1.4 g, 6.1 mmol) in DCM (3 ml) maintaining a temperature of less than −70°. After 3 h at −78 C the solution was poured into saturated $NaHCO_3$ solution (40 ml), extracted into DCM, washed ($NaHCO_3$×1, $H_2O$×1), dried ($MgSO_4$), the solution concentrated in vacuo and the residue distilled (170°, 0.4 mm Hg) to give 1.1 g of clear liquid. To this liquid was added TFA (20 ml) and the solution heated at reflux for 15 min. The solvent was removed in vacuo, the residue slurried in $Et_2O$ and the off-white solids isolated by filtration and dried to give the title compound (760 mg, 72%). δ H ($d^6$-DMSO) 7.80 (2H, d, J 8.4 Hz), 7.31 (2H, t), 7.16 (1H, t, J 7.35 Hz), 2.51 (4H, s). m/z (ESI, 70V) 175 ($MH^+$).

INTERMEDIATE 5

2-Propyl-1,3-cyclopentanedione

To a solution of $BF_3.OEt_2$ (1.30 g, 9.2 mmol) and butyraldehyde (0.40 g, 5.5 mmol) in DCM (5 ml) under $N_2$ at −78° was added a solution of 1,2-bis trimethylsilyloxycyclobutene (1.4 g, 6.1 mmol) in DCM (3 ml) maintaining a temperature of less than −70°. After 2 h at −78° the solution was poured into saturated NaHCO$_3$, extracted into EtOAc, washed (brine), dried (MgSO$_4$) and the solution concentrated in vacuo to yield a clear liquid. To this liquid was added TFA (20 ml) and the solution heated at reflux for 24 h.

The solution was concentrated in vacuo and the residue purified by chromatography (SiO$_2$, 50:50 EtOAc/hexane) to yield the title compound as an off-white solid (140 mg, 18%). δ H (CD$_3$OD) 2.46 (4H, s), 2.07 (2H, t, J 7.5 Hz), 1.40 (2H, m), 0.86 (3H, t, j 7.4 Hz). m/z (ESI, 70V) 141 (MH$^+$).

INTERMEDIATE 6

2-Isopropyl-1,3-cyclopentanedione

To a solution of TiCl$_4$ (1.47 g, 7.77 mmol) and isobutyraldehyde (559 mg, 7.75 mmol) in DCM (16 ml) under N$_2$ at −78° was added a solution of 1,2-bistrimethylsilyloxycyclobutene (1.97 g, 8.56 mmol) in DCM (16 ml) maintaining a temperature of less than −70°. After 30 min the reaction was poured into water, extracted into DCM, washed (H$_2$O×2), dried (MgSO$_4$) and the solution concentrated in vacuo to yield a clear oil. To this oil was added TFA (20 ml) and the solution heated at reflux for 24 h. The solution was concentrated in vacuo and the residue purified by chromatography (SiO$_2$; 50:50 EtOAc/hexane) to give the title compound as an off-white solid (180 mg, 17%). δ H (d$^6$-DMSO) 2.61 (1H, sept, J 7.0 Hz), 2.29 (4H, s), 1.04 (6H, d, J 7.0 Hz). m/z (ESI, 70V) 141 (MH$^+$).

INTERMEDIATE 7

2-Isobutyl-1,3-cyclopenentanedione

To a stirring mixtue of silica gel (45 g) isobutyraldehyde (375 mg, 5.20) and 4-methylbenzenethiol (3.80g, 30.6 mmol) in DCM (15 ml) was addd 1,3-cyclopentanedione (300 mg, 3.06 mmol). The suspension was stirred for 24 h, the solvent removed in vacuo, the residues dry packed onto the top of a silica column and the column run with gradient elution (SiO$_2$; 100:0–50:50 Hexane/EtOAc) to give a thiol trapped intermediate as a white solid (400 mg, 47%). To this intermediate (300 mg, 1.09 mmol) in MeOH (5 ml) was added NaCNBH$_3$ (55 mg, 0.8 mmol), the reaction stirred for 24 h and quenched with water. The solution was concentrated in vacuo and the residue purified by chromatography (SiO$_2$: 50:50, EtOAc/hexane) to give the title compound as an off-white solid (80 mg, 28% overall). δ H (CD$_3$OD) 2.43 (4H, s), 1.96 (2H, d, J 7.1 Hz), 1.77 (1H, sept, J 6.6 Hz), 0.83 (6H, d, J 6.6 Hz). m/z (ESI, 70V) 155 (MH$^+$).

INTERMEDIATE 8

2-(1-Ethylpropyl-1,3-cyclopentanedione

Prepared in a similar manner to intermediate 6 from 2-ethylbutyraldehyde δ H (CD$_3$OD) 2.46 (4H, s), 2.30 (1H, m), 1.67 (2H, m), 1.52 (2H, m), 0.76 (6H, t, J 7.4 Hz). m/z (ESI, 70V) 169 (MH$^+$).

INTERMEDIATE 9

2-Cyclohexyl-1,3-cyclopentanedione

To a suspension of 1,3-cyclopentandedione (4.00 g, 0.040 mmol) in water (30 ml) were added LiOH.H$_2$O (1.88g, 0.045 moll) and 3-bromocyclohexene (7.18 g, 0.045 mmol). The solution was stirred overnight, the pH raised to 12–14 (LiOH.H$_2$O) and stirred for 2 h. The solution was washed with Et$_2$O (4×40 ml), acidified to pH 1–2 and resulting solids isolated by filtration, washed and dried to give 2-cyclohexene-1,3-cyclopentanedione. [δ H (CD$_3$OD) 5.69 (1H, m), 5.44 (1H, m), 3.20 (1H, m), 2.47 (4H, s), 2.15–1.19–(6H, m). m/z ESI, 70V) 179 (MH$^+$)]. The product was dissolved in EtOH (50 ml) and reduced under an atmosphere of H$_2$ at RT with Pd/C (200 mg). After 5 h the reaction was filtered and the solvent removed to give the title compound as a white solid (890 mg. 12%). δ H (CD$_3$OD) 2.44 (4H, 2), 2.39 (1H, m), 1.85–1.70 (5H, m), 1.50–1.45 (2H, m), 1.35–1.15 (3H, m). m/z (ESI, 70V) 181 (MH$^+$).

INTERMEDIATE 10

4-(2-(N,N-Domethylamino)ethylen-1-yl)-3-cyanopyridine

A solution of 4-methyl-3-cyanopyridine (prepared according to Ref: J. Prakt. Chem. 338, 663 (1996), 8.0 g, 67.8 mmol) and N,N-dimethylformamide diethyl acetal (11.0 g, 74.8 mmol) in dry DMF (50 ml) was stirred at 140° under N$_2$ for 2 days. An additional portion of N,N,-dimethylformamide diethyl acetal (5 g) was added and stirred at 140° for 4 h. The volatiles were removed in vacuo and the obtained dark oil partitioned between EtOAc (300 ml) and water (50 ml). The phases were separated and the aqueous layer re-extracted with EtOAc (3×100 ml). The combined organic extracts were washed with brine (30 ml), dried (Na$_2$SO$_4$), treated with activated charcoal, filtered and evaporated in vacuo to afford essentially pure title compound as a dull orange solid (10.1 g, 85%). δ H (CDCl$_3$) 8.49 (1H, s), 8.25 (1h, d, J 5.9 hz), 7.29 (1H, d, J 13.2 Hz), 7.09 (1H, d, J 5.9 Hz), 5.25 (1H, d, J 13.2 Hz) and 2.99 (6H, s); m/z (ES$^+$, 70V) 174 (MH$^+$).

INTERMEDIATE 11

1-Hydroxy-2,7-naphthyridine Hydrochloride Salt

HCl gas was bubbled through a stirred solution of Intermediate 10 (6.2 g, 3.58 mmol) in glacial acetic acid (50 ml) and water (0.64 ml, 3.55 mmol) for 1–2 min. The reaction mixture was stirred in a stoppered flask at 40° for 18 h. The volatiles were removed in vacuo affording a dark residue, which was treated with water (3×20 ml) and re-evaporated in vacuo. The obtained dark semi-solid was treated with 40 ml warm ethanol, ice-cooled, and the undissolved solid collected by filtration affording the title compound as a green coloured solid (5.2 g, 80%) δ H (DMSO-D$^6$) 12.5 (1H, br, s), 9.38 (1H, s), 8.84 (1H, d, J 7.0 Hz), 8.15 (1H, d, J 7.0 Hz), 7.89 (1H, br, dd, J7.0, 5.0 Hz) and 6.85 (1H, d, J 7.0 Hz); m/z (ES$^+$, 70V), 147 (MH$^+$).

INTERMEDIATE 12

1-Chloro-2,7-naphthyridine

Intermediate 11 (5.2 g, 28.5 mmol) was stirred with phosphorous oxychloride (75 ml) at 110° for 24 h. The volatiles were removed in vacuo affording a dark oil which was poured into an ica-bath cooled mixture of saturated aqueous NaHCO$_3$ (100 ml containing 20 g solid NaHCO$_3$) and EtOAc (100 ml). After thorough mixing the phases were separated and the aqueous layer re-extracted with EtOAc (2×75 ml). The combined organic extracts were washed with brine (15 ml), dried (Na$_2$SO$_4$) and evaporated in vacuo to afford the title compound as a yellow solid (4.0 g, 85%) δ H (CDCl$_3$) 9.45 (1H, s), 8.81 (1H, d, J 5.7 Hz), 8.47 (1H, d, J 5.7 Hz), 7.66 (1H, d, J 5.7 Hz) and 7.60 (1H, d, J 5.7 Hz); m/z (ES$^+$, 70V) 165 and 167 (MH$^+$).

INTERMEDIATE 13

Ethyl (S)-3-[4-(2,7-Naphthyridin-1-ylamino)phenyl]-2-aminopropanoate

A solution of ethyl-(S)-3-[4-aminophenyl]-2-[t-butoxycarbonylamino]propanoate (638 mg, 2.07 mmol) and Intermediate 12 (310 mg, 1.88 mmol) in ethoxyethanol (2 ml) was stirred at 120° for 15 min and at 100° for 1 h under nitrogen. The volatiles were removed in vacuo and the dark residue partitioned between EtOAc (70 ml) and saturated aqueous NaHCO$_3$ (10 ml). The phases were separated and the aqueous layer re-extracted with EtOAc (2×30 ml). The combined organic extracts were washed with brine (10 ml), dried (Na$_2$SO$_4$) and evaporated in vacuo to afford a dark foam. Chromatography (SiO$_2$; 5 to 10% MeOH/DCM) afforded a mixture of ethyl-(S)-3-[4-(2,7-naphthyridin-1-ylamino)phenyl]-2-[(t-butoxycarbonyl)amino]propanoate and some of the title compound (730 mg). This mixture was treated with a solution of trifluoroacetic acid (5 ml) and DCM (5 ml) at room temperature for 1 h. The volatiles were removed in vacuo and the residue partitioned between EtOAc (75 ml) and saturated aqueous NaHCO$_3$ (20 ml). The phases were separated and the aqueous layer re-extracted with EtOAc (3×30 ml). The combined organic extracts were washed with brine (10 ml), dried (Na$_2$SO$_4$) and evaporated in vacuo to afford an orange solid. Chromatography (silica; 10% MeOH/DCM) afforded the title compound as a straw-coloured solid (420 mg, 60% over two steps). δ H (CDCl$_3$) 10.70 (1H, s), 10.31 (1H, s), 9.44 (1H, d, J 5.6 Hz), 8.94 (1H, d, J 5.6 Hz), 8.55 (1H, d, J 7.3 Hz), 8.54 (2H, d, J 8.5 Hz), 8.46 (1H, d, J 5.6 Hz), 7.94 (2H, d, J 8.5 Hz), 4.84 (2H, q, J 7.1 Hz), 4.35 (1H, t, J 6.6 Hz), 4.10 (2H, br, s), 3.64 (1H, dd, J 13.5, 6.4 Hz), 3.56 (1H, dd, J 13.5, 7.0 Hz) and 1.95 (3H, t, J 7.1 Hz); m/z (ES$^+$, 70V) 337 (MH$^+$).

INTERMEDIATE 14

Ethyl (S)-3-[4-(2,7-Naphthyridin-1-yloxy)phenyl]-2-aminopropanoate

A mixture of N-(BOC)-(S)-tyrosine ethyl ester (1.79 g, 5.80 (mmol) potassium carbonate (0.80 g, 5.80 mmol) and Intermediate 12 (1.0 g, 6.08 mmol) in dry DMF (10 ml) was stirred at room temperature for 18 h, and at 40° for 18 h. The DMF was removed in vacuo and the residue partitioned between EtOAc (80 ml) and 10% aqueous Na$_2$CO$_3$ (20 ml). The phases were separated and the aqueous layer re-extracted with EtOAc (2×20 ml). The combined organic extracts were washed with brine (10 ml), dried (Na$_2$SO$_4$) and evaporated in vacuo to afford a new colourless oil. Chromatography (silica; 2.5% MeOH/DCM) afforded reasonably pure N-t-butoxycarbonyl protected title compound (1.81 g, 71%). This material was dissolved in EtOAc (40 ml) and HCl gas was bubbled through the stirred solution for 1 min. then the mixture was stirred for an additional 0.5 h. The volatiles were removed in vacuo affording a yellow solid which was partitioned between EtOAc (80 ml) and saturated aqueous NaHCO$_3$ (20 ml). The phases were separated and the aqueous layer re-extracted with EtOAc (2×20 ml). The combined organic extracts were washed with brine (10 ml), dried (Na$_2$SO$_4$) and evaporated in vacuo. The obtained oil was chromatographed (silica; 5% MeOH/DCM) to afford the title compound as a near colourless oil (0.87 g, 62%) 8H (CDCl$_3$) 9.77 (1H, s), 8.75 (1H, d, J 5.8 Hz), 8.10 (1H, d, J 5.8 Hz), 7.58 (1H, d, J 5.8 Hz), 7.29 (2H, d, J 8.4 Hz), 7.25 (1H, d, J 5.9 Hz), 7.21 (2H, d, J 8.4 Hz), 4.22 (2H, q, J 7/1 Hz), 3.80–3.70 (1H, obscured m), 3.15 (1H, dd, J 13.6, 5.1 Hz), 2.88 (1H, dd, J 13.6, 8.0 Hz) 1.30 (3H, t, J 7.1 Hz) and 0.78 (2H, br, s); m/z (ES$^+$, 70V) 324 (MH$^+$).

INTERMEDIATE 15

4-Acetonyl-3-cyanopyridine

A solution of 4-methyl-3-cyanopyridine (4 g, 33.9 mmol) and N,N-dimethylacetamide dimethylacetyl (5.4 g, 40.6 mmol) in dry DMF (20 ml) was stirred at 130° for 7 h. The volatiles were removed in vacuo to afford a dark oil which solidified on standing. This material was chromatographed (silica; 50% EtOAc/Hexane—100% EtOAc) affording the title compound as an off-yellow solid (3.739, 69%). δ H (CDCl$_3$) 8.87 (1H, s), 8.74 (1H, d, J 5.2 Hz), 7.28 (1H, d, J 5,2 Hz), 4.00 (2H, s) and 2.36 (3H, s); m/z (ES$^+$, 70V) 161 (MH$^+$).

INTERMEDIATE 16

1-Hydroxy-3-methyl-2,7-naphthyridine Hydrochloride

HCl gas was bubbled through a stirred solution of Intermediate 15 (3.73 g, 23.3 mmol) in glacial acetic acid (40 ml) for several minutes. The flask was stoppered and reaction stirred for 18 h at ambient temperature. The volatiles were removed in vacuo affording a straw-coloured solid. This was twice treated with water (30 ml portions) and re-evaporated in vacuo to dryness, affording the title compound (contaminated with ~25% unidentified by-product) as a dark straw coloured solid (4.1 g). δ H (DMSO-d$^6$) 12.46 (1H, br, s), 9.32 (1H, s), 8.71 (1H, d, J 6.5 Hz), 7.98 (1H, d, J 6.5 Hz), 6.67 (1H, s) and 2.38 (3H, s); m/z (ES$^+$, 70V) 161 (MH$^+$). Used without further purification.

INTERMEDIATE 17

1-Chloro-3-methyl-2,7-naphthyridine

Intermediate 16 (4.1 g) was treated with phosphorus oxychloride (50 ml) at 130° for 3 h, affording a dark solution. The volatiles were removed in vacuo and the obtained dark oil extracted with Et$_2$O (100 ml). Saturated aqueous NaHCO$_3$ (ice cold; containing 10 g additional solid NaHCO$_3$) was poured (with CARE!) onto the crude product with swirling and ice-bath cooling. After thorough shaking, addition Et$_2$O (80 ml) was added, the mixture re-shaken, and the phases separated. The aqueous layer was re-extracted with Et$_2$O (2×80 ml) and the combined ethereal extracts washed with brine (20 ml), dried (Na$_2$SO$_4$) and evaporated in vacuo to afford an orange solid (3.6 g). Chromatography (silica; 70% EtOAc/Hexane—100% EtOAc) afforded a more-polar by-product (3-methyl-1H-pyrano[3,4-C]pyridin-1-one, (0.7 g) and the title compound as a white solid (2.82 g, 79% from intermediate 7) δ H (CDCl$_3$) 9.66 (1H, s), 8.73 (1H, d, J 5.8 hz), 7.56 (1H, d, J 5.8 Hz), 7.40 (1H, s) and 2,69 (3H, s); m/z (ES$^+$, 70V) 179 and 181 (MH$^+$).

INTERMEDIATE 18

Ethyl (S)-3-[4-(3-Methyl-2,7-naphthyridin-1-ylaminolphenyl]-2-[N-(tertbutyloxycarbonyl)amino]propanoate Hydrochloride Acetylchloride (55 mg, 50 µl, 0.70 mmol) was added to absolute ethanol (25 ml) and stirred for one minute. Intermediate 17 (2.50 g, 14.0 mmol) and ethyl-(S)-3-[4-aminophenyl]-2-{tert-butyloxycarbonyl]propanoate (4.31 g, 14.0 mmol) were added and the reaction mixture stirred at 60° for 2.75h. The volatiles were removed in vacuo to afford a yellow-orange solid. This was treated with EtOAc (~25 ml), warmed, re-cooled and the precipitate collected by filtration, with Et$_2$O washing, affording the title compound as yellow solid (4.96 g, 73%). δ H (CDCl$_3$) 10.44 (1h, br, s), 10.33 (1H, br, s), 8.60 (1H, d, J 6.5 Hz), 8.00 (1H, d, J 6.5 Hz), 7.85 (2H, d, J 8.5 Hz), 7.28 (1H, d, J 8.0 Hz), 7.23 (2H, d, J 8.5 Hz), 7.16 (1H, s), 4.19–4.01 (1H, m), 4.08 (2H, q, J 7.0 Hz), 2.97 (1H, dd, J 13.8, 5.4 Hz), 2.86 (1H, dd, J 13.8, 10.0 Hz), 2.50 (3H, s), 1.34 (9H, s) and 1.15 (3H, t, J 7.0 Hz); m/z (ES$^+$, 70V) 451 (MH$^+$).

INTERMEDIATE 19

Ethyl-(S)-3-[4-(3-methyl-2,7-naphthyridin-1-ylamino)phenyl]-2-aminopropanoate HCl gas was bubbled through a stirred solution of Intermediate 18 (4.95 g, 10.2 mmol) for 1–2 min. After 30 min stirring at ambient temperature the volatiles were removed in vacuo affording a yellow powder. This was treatd with saturated aqueous NaHCO$_3$ (30 ml) then extracted with EtOAc (100 ml, and 3×50 ml). The combined organic extracts were washed with brine (10 ml), dried (Na$_2$SO$_4$) and evaporated in vacuo affording the title compound as a yellow solid (3.56, 100%). δ H (CDCl$_3$) 9.25 (1H, s), 8.50 (1H, d, J 5.6 Hz), 7.66 (2H, d, J 8.4 Hz), 7.35 (1H, d, J 5.6 Hz), 7.34 (1H, masked s), 7.14 (2H, d, J 8.4 Hz), 6.81 (1H, s), 4.12 (2H, q, J 7.2 Hz), 3.65 91H, dd, J 7.8, 5.2 Hz), 3.02 (1H, dd, J 13.7, 5.2 Hz), 2.80 (1H, dd, J 13.7, 7.8 Hz), 2.48 (3H, s), 1.56 (2H, br, s) and 1.21 (3H, t, J 7.2 Hz); m/z (ES$^+$, 70V) 351 (MH$^+$).

INTERMEDIATE 20

Ethyl (S)-3-[4-(3-Methyl-2,7-naphthyridin-1-yloxy)phenyl]-2-(N-t-butyloxycarbonylamino)-propanoate A mixture of N-tbutyloxycarbonyl-(S)-tyrosine ethyl ester (14.5 g, 46.9 mmol), caesium carbonate (14.05 g, 43.1 mmol) and Intermediate 17 (7.0 g, 39.2 mmol) in dry DMF (60 ml) was stirred at room temperature for 48 h. The reaction was diluted with Et$_2$O (150 ml) and filtered off. The filtrate was evaporated under high vacuum and the residue was chromatographed (SiO$_2$; 40%–60% EtOAc/Hexane) which afforded the title compound as a viscous, straw-coloured oil (16.2g, 77%) δ H (CDCl$_3$) 9.56 (1H, s), 8.58 (1H, d, J 5.8 Hz), 7.39 (1H, d, J 5.8 Hz), 7.15–7.10 (4H, m), 7.00 (1H, s), 4.99–4.91 (1H, m), 4.54–4.46 (1H, m), 4.09 (2H, q, J 7.1 Hz), 3.10–2.99 (2H, m), 2.36 (3H, s), 1.34 (9H, s) and 1.15 (3H, t, J 7.1 Hz); m/z (ES$^+$, 70V) 452 (MH$^+$).

INTERMEDIATE 21

Ethyl (S)-3-[4-(3-Methyl-2,7-naphthyridin-1-yloxy)phenyl]-2-aminopropanoate

HCl gas was bubbled through a stirred solution of Intermediate 20 (16 g) in EtOAc (300 ml) until a persistent fine white precipitate formed (~2 minutes). After stirring for 0.5 h the volatiles were removed in vacuo. The obtained solid was partitioned between EtOAc (250 ml) and saturated aqueous NaHCO$_3$ (80 ml plus 5 g solid NaHCO$_3$). The phases were separated and the aqueous layer re-extracted with EtOAc (5×50 ml). The combined organic extracts were washed with brine (10 ml), dried (Na$_2$SO$_4$) and evaporated in vacuo to afford an oil Chromatography (SiO$_2$; 100% EtOAC—10% EtOH/EtOAc) afforded the title compound as a viscous oil (11.1 g, 89%). δ H (CDCl$_3$) 9.71 (1H, s), 8.70 (1H, d, J 5 Hz), 7.50 (1H, d, J 5.8 Hz), 7.31–7.28 (4H, m), 7.11 (1H, s), 4.23 (2H, q, J 7.1 Hz), 3.79–3.72 (1H, m), 3.14 (1H, dd, J 14.1, 5.4 Hz), 2.94 (1H, dd, J 14.1, 7.8 Hz), 2.47 (3H, s), 1.75–1.50 (2H, br, s) and 1.30 (3H, t, J 7.1 Hz); m/z (ES$^+$, 70V) 352 (MH$^+$).

INTERMEDIATE 22

Methyl (2S)-2-[(tert-Butoxycarbonyl)amino]-3-(4-{[trifluoromethylsulphonyl]oxy}phenyl)propanoate Triflic anhydride (5.05 ml, 30 mmol) was added to a mixture of N-BOC tyrosine methyl ester (7.38 g, 25 mmol) and pyridine (10 ml, 125 mmol) in DCM (40 ml) at 0°. After 45 min at 0° water (80 ml) and DCM (100 ml) were added. The organic phase was washed with NaOH aq. (0.5M, 60 ml), water (60 ml), citric acid (10%, 2×80 ml) and water (60 ml), dried (Na$_2$SO$_4$) and concentrated in vacuo to give the title compound as a yellow oil which solidified on standing (10.6 g). δ H (CDCl$_3$) 7.26–7.18 (4H, m), 5.05 (1H, v br, d), 4.59 (1H, v br, q), 3.70 (3H, s), 3.16 (1H, dd, J 13.7, 5.7 Hz), 3.02 (1H, dd, J 13.8, 6.5 Hz), 1.40 (9H, s); m/z (ES$^+$, 70V) 450 (M+$^+$Na).

INTERMEDIATE 23

Methyl (2S)-2-[(tert-Butoxycarbonyl)amino]-3-(4-[2',6'-dimethoxy]biphenylyl)propanoate A mixture of the Intermediate 22 (4.27 g, 10 mmol), 2,6-dimethoxybenzene boronic acid (4.55 g, 25 mmol), potassium carbonate (6.9 g, 50 mmol) tetrakis (triphenylphosphine)palladium(0) (2.31 g) in DME (45 ml) and water (5 ml) was heated at 80° overnight. The mixture was diluted with EtOAc, washed with dilute HCl, NaHCO$_3$ (aq.), water and brine, dried (Na$_2$SO$_4$) and concentrated in vacuo. Column chromatography (SiO$_2$; EtOAc/hexane, 20:80–30:70) gave the title compound (2.27 g). δ H (DMSO-d$^6$) 7.33 (1H, d, J 8.2 Hz), 7.27 (1H, t, J 8.3 Hz), 7.20 (2H, d, J 8.1 Hz), 7.10 (2H, d, J 8.0 Hz), 6.71 (2H, d, J 8.4 Hz), 4.2 (1H, m), 3.63 (9H, s), 3.01 (1H, dd, J 13.9, 4.5 Hz), 2.84 (1H, dd, J 13.7, 10.3 Hz), 1.34 (9H, s); m/z (ES$^+$, 70V) 438 (M+$^+$Na).

INTERMEDIATE 24

Methyl (2S)-2-Amino-3-(4-[2',6'-dimethoxy]biphenylyl)propionate Hydochloride Anhydrous HCl was bubbled through a solution of Intermediate 23 (1.30 g, 3.13 mmol) in EtOAc (30 ml) for a few seconds. The mixture was stirred at room temperature for 1 h. Some solvent was removed in vacuo until material began to precipitate. The precipitate was filtered off and dried to give the title compound as pale yellow crystals (888 mg, 81%). δ H (DMSO-d$^6$) 8.7 (2H, br, s), 7.28 (1H, t, J 8.4 Hz), 7.21 (2H, d, J 8.4 Hz), 7.17 (2H, d, J 8.3 Hz), 6.73 (2H, d, J 8.4 Hz), 4.30 (1H, t, J 6.6 Hz), 3.69 (3H, s), 3.64 (6H, s), 3.18 (1H, dd, J 4.1, 6.2 Hz), 3.10 (1H, dd, J 14.1, 7.1 Hz); m/z (ES$^+$, 70V) 316 (MH$^+$).

INTERMEDIATE 25

Ethyl N-(Diphenylmethylene)-2-amino-3-(5-benzenesulphonyloxypyrid-2-yl)propionate A solution of ethyl N-(diphenylmethylene)glycinate (1.71 g, 6.40 mmol) in dry THF (10 ml) was added to a stirrred solution of LDA (2M in heptane/TNF/ethylbenzene, 320 ml, 6.40 mmol) in dry THF 910 ml) at −70° under nitrogen. After stirring at this temperture for 0.75 h, a solution of 5-benzenesulphonyloxy-2-bromomethylpyridine (2.00 g, 6.01 mmol); [prepared as described by Myers et al, J.O.C. 61, 813 (1996)] in dry THF (10 ml) was added. The reaction mixture was stirred at −70° for 1 h then at room temperature for 18 h. The reaction was quenched with water 910 ml) then partitioned between EtOAc (70 ml) and bring (30 ml). The phases were separated and the aqueous phase re-extracted with EtOAc (2×40 ml). The combined organic extracts were washed with brine (10 ml), dried ($Na_2SO_4$) and evaporated in vacuo to afford the crude product as a dark oil. Chromatography (silica: 60–75% $Et_2O$/Hexane) afforded the title compound as a tan-coloured solid (2.25 g, 72%). δ H ($CDCl_3$) 8.02 (1H, d, J 2.8 Hz), 7.72 (2H, d, J 8.0 hz), 7.59 (1H, t, J 8.0 hz), 7.50 (2H, dd, J 8.4 Hz), 7.40–7.27 (8H, m), 7.19 (1H, dd, J 8.5, 2.8 Hz), 7.11 (1H, d, J 8.5 Hz), 6.67 (2H, br, d, J 8.0 Hz), 4.50 (1H, dd, J 9.0, 4.6 Hz), 4.25–4.10 (2H, m), 3.50–3.33 (2H, m) and 1.24 (3H, t, J 7.2 Hz), m/z ($ES^+$, 70V) 515 ($MH^+$).

INTERMEDIATE 26

Ethyl 2-Amino-3-(5-benzenesulphonyloxypyrid-2-yl)propionate

A solution of Intermediate 25 (1.9 g, 3.7 mmol) in 10% aqueous HCl (5 ml) and ethanol (120 ml) was stirred at room temperature for 1.5 h. Most of the solvent was removed in vacuo and the residue partitioned between half-saturated aqueous $NaHCO_3$ (50 ml) and EtOAc (80 ml). The phases were separated and the aqueous layer re-extracted with EtOAc (4×40 ml). The combined organic extracts were dried ($Na_2SO_4$) and evaporated in vacuo. The obtained yellow oil was chromatographed (silica; EtOAc) to afford the title compound as a coourless oil (1.15 g, 78%). δ H ($CDCl_3$) 8.04 (1H, d, J 2.8 Hz), 7.80 (2H, d, t 8.0 Hz), 7.65 (1H, t, J 80 Hz), 7.51 (2H, t, J 8.0 Hz), 7.31 (1H, dd, J 8.5, 2.8 Hz), 7.12 (1H, d, J 8.5 Hz), 4.10 (2H, q, J 7.1 Hz), 3.86 (1H, dd, J 7.9, 4.9 Hz), 3.19 (1H, dd, J 14.4, 4.9 Hz), 2.99 (1H, dd, J 14.4, 7.9 Hz), 1.66 (2H, br, s) and 1.17 (3H, t, J 7.1 Hz). m/z ($ES^+$, 70V) 351 ($MH^+$).

INTERMEDIATE 27

Ethyl-2-(N-t-butyloxycarbonylamino)-3(5-hydroxypyrid-2-yl)propionate

A solution of Intermediate 26 (3.50 g, 10 mmol) and LiOH/$H_2O$ (920 mg, 22 mmol) in dioxan (20 ml) and water (30 ml) was stirred at room temperature for 5 h. The volatiles were removed in vavuo and the residue treated with ethanol (50 ml). HCl gas was bubbled through the mixture for a few minutes and the reaction mixture heated at 50° overnight. The volatiles were removed in vacuo and the residue treated with a mixture of di-tert-butyl dicarbonate (1.53 g, 7.0 mmol) and $NaHCO_3$ (3.36 g, 40 mmol) in THF (10 ml) and water (20 ml). After stirring at room temperature for 2 h, additional di-tert-butyidicarbonate (150 mg, 0.7 mmol) was added, the reaction mixture stirred for a further 2 h. The organic volatiles were removed in vacuo and aqueous residue was extracted with EtOAc (2×75 ml). The combined organic extracts were washed with brine (5 ml), dried ($MgSO_4$) and evaporated in vacuo. The crude product was chromatographed (silica, 50% EtOAc/hexane) to afford the title compound as a white solid (1.81 g, 58%), δ H ($CDCl_3$; 8:3 ratio of rotamers) 8.14 (0.73H, br, s), 8.01 (0.27H, br, s), 7.18–7.08 (1H, m), 7.086.90 (1H, m), 6.24 (0.27H, br, dm, J 8.5 Hz), 5.77 (0.73H, br, d, J 8.5 Hz), 4.64 (0.73H, m), 4.43 (0.27H, m), 4.17 (2H, q, J 7.1 Hz), 3.27–3.14 (2H, m), 1.41 (9H, s and 1.23 (3H, t, J 7.1 Hz). m/z ($ES^+$, 70V) 311 ($MH^+$).

INTERMEDIATE 28

Ethyl-2-(N-t-butyloxycarbonylamino)-3-[5-(3-methyl-2,7-naphthyridin-1-yloxy)-pyrid-2-yl] propionate A mixture of intermediate 27 (1.814 g, 5.85 mmol), Intermediate 17 (0.87 g, 4.87 mmol) and $Cs_2CO_3$ (1.73 g, 5.31 mmol) in dry DMF (12 ml) was stirred at 40° overnight. The inorganics were removed by filtration with DCM washed and the filtrate evaporated in vacuo to afford a dark oil. Chromatography (silica; 50% EtOAc/Hexane—100% EtOAc) afforded the title compound as a white foam (1.69 g, 77%). δ H ($CDCl_3$) 9.71 (1H, s), 8.72 (1H, d, J 5.8 Hz), 8.56 (1H, d, J 2.7 Hz), 7.62 (1H, dd, J 8.4, 2.7 Hz), 7.53 (1H, dd, J 5.8, 0.8 Hz), 7.26 (1H, d, J 8.4 Hz), 7.15 (1H, s), 5.86 (1H, br, d, J 9.2 Hz), 4.71 (1H, m), 4.81 (2H, m), 3.45–3.29 (2H, m), 1.46 (9H, s) and 1.27 (3H, t, J 7.2 Hz); m/z ($ES^+$, 70V) 453 ($MH^+$).

INTERMEDIATE 29

Ethyl-2-amino-3-[5-(3-methyl-2,7-nalphthyridin-1-yloxy)pyrid-2-yl]propionate Intermediate 28 was dissolved in EtOAc and HCl gas bubbled through for 10 min. Solution neutralised with aqueous $NaHCO_3$ and extracted into EtOAc to quantitatively give the title compound used crude without purification.

INTERMEDIATE 30

1,1-Dioxo-tetrahydrothiophen-3-one

Tetrahydrothiophen-3-one (2 g, 19.6 mmol) in $CH_2Cl_2$ (100 ml) at 0° was treated with 3-chloroperoxybenzoic acid (9 g) in $CH_2Cl_2$ (10 ml). After 3 h the reaction was complete and the solid removed by filtration and the filtrate concentrated in vacuo. The title compound was purified by chromatography ($SiO_2$; EtOAc/hexane 4:1) to give the title compound as a white solid (340 mg; 2.5 mmol; 13%). δ H ($CDCl_3$) 3.72 (2H, s), 3.60 (2H, t, J 7.8 Hz), 3.10 (2H, t, J 7.8 Hz). m/z ($ES^+$, 70V) 135 ($MH^+$).

EXAMPLE 1

(2S)-Ethyl-3-{4-(3,5-dichloropyrid-4-ylcarboxamido)phenyl]-2-[(3-oxo-1-cyclopentenyl)amino]propionate A solution of (S)-ethyl-3-[4-(3,5-dichloropyrid-4-yl carboxamido)phenyl]-2-aminopropionate (prepared from 3,5-dichloroisonicotinoyl chloride and N-BOC-L-4 aminophenylalanine ethylester) (128 mg, 0.34 mmol), and 1,3-cyclopentanedione (49 mg, 0.50 mmol) in chloroform (5 ml) was treated with 4 Å molecular sieves (~1 g) and heated to reflux for 24 h. The sieves were removed by filtration, the solution concentrated in vacuo and the residue purified by chromatography ($SiO_2$, gradient elution 98:2–96:4 DCM/MeOH) to give the title compound as a white solid (120 mg, 77%). δ H ($CD_3OD$) 8.61 (2H, s), 7.59 (2H, d, J 8.5 Hz), 7.25 (2H, d, J 8.5 Hz), 4.98 (1H, s), 4.33 (1H, t), 4.16 (2H, q, J 7.1 Hz), 3.29–3.03 (2H, m), 2.63 (2H, m), 2.32 (2H, t, J 5.1 Hz), 1.22 (3H, t, J 7.1 Hz). m/z (ESI, 70V) 462 ($MH^+$).

In a similar manner to Example 1 were prepared Examples 2 to 4.

EXAMPLE 2

(2S)-Ethyl-3-[4-(3,5-dichloropyrid-4-ylcarboxamido)phenyl]-2-[(3-oxo-1-cyclohexenyl)amino]propionate Prepared from 1,3-cyclohexanedione δ H (CD$_3$OD) 8.62 (2H, s), 7.59 (2H, d, J 8.5 Hz), 7.25 (2H, d, J 8.5 Hz), 5.04 (1H, s), 4.35 (1H, t), 4.14 (2H, q, J 7.1 Hz), 3.21–3.03 (2H, m), 2.43 (2H, m), 2.23 (2H, t, J 6.3 Hz), 1.89 (2H, m), 1.19 (3H, t, J 7.1 Hz). m/z (ESI, 70V) 476 (MH$^+$).

EXAMPLE 3

(2S)-Ethyl-3-[4-(3,5-dichloropyrid-4-ylcarboxamido)phenyl]-2-[(2-ethyl-3-oxo-1-cyclopentenyl)amino]propionate Prepared from 2-ethyl-1,3-cyclopentanedione. Heated at reflux in 1,2-dichloro-ethane for 5 days. δ H (CD$_3$OD) 8.62 (2H, s), 7.59 (2H, d, J 8.4 Hz), 7.29 (2H, d, J 8.4 Hz), 4.48 (1H, m), 4.22 (2H, q, J 7.1 Hz), 3.32 (1H, dd, J 13.7, 4.6 Hz), 3.06 (1H, dd, J 13.7, 9.8 Hz), 2.5–2.0 (6H, m), 1.27 (3H, t, J 7.1 Hz), 0.91 (3H, t, J 7.4 Hz). m/z (ESI, 70V) 490 (MH$^+$).

EXAMPLE 4

(2S)-Ethyl-3-[4-(3,5-dichloropyrid-4-ylcarboxamido)phenyl]-2-[(5,5-dimethyl-3-oxo-1-cyclohexenyl)amino]propionate Using 5,5-dimethyl-1,3-cyclohexanedione. Heated at reflux in 1,2-dichloroethane for 5 days (SiO$_2$, gradient 75:25–100:0 EtOAc/hexane). δ H (CD$_3$OD) 8.64 (2H, s), 7.58 (2H, d, J 8.5 Hz), 7.26 (2H, d, J 8.5 Hz), 5.03 (1H, s), 4.36 (1H, m), 4.16 (2H, q, J 7.1 Hz), 3.22 (1H, m), 3.05 (1H, m), 2.29–2.11 (4H, m), 1.23 (3H, t, J 7.1 Hz), 1.03 (3H, s), 0.97 (3H, s). m/z (ESI, 70V) 504 (MH$^+$).

EXAMPLE 5

(2S)-Ethyl-3-[4-(2,6-Naphthyridin-1-yl)amino)phenyl]-2-[(2-methyl-3-oxo-1-cyclopentenyl)amino]propionate A solution of (S)-ethyl-3-(2,6-naphthyrid-1-yl)amino)phenyl]-2-aminopropionate (prepared from 1-chloro-2,6-naphthyridine and N-BOC-L-4-aminophenylalanine ethyl ester as described in International Patent Application WO 00/73260) (512 mg, 1.52 mmol) and 2-methyl-1,3-cyclopentanedione (179 mg, 1.60 mmol) in 1,2-dichloroethane (20 ml) was treated with 4 Å molecular sieves (0.5 g) and heated at 90° C. for 3 days. The solution was filtered, concentrated in in vacuo and the residue purified by chromatography (SiO$_2$, 98.2: 96.4 DCM/MeOH) to give the title compound as a yellow solid (388 mg, 59%). δ H (CD$_3$OD) 9.13 (1H, s), 8.56 (1H, d, J 6.0 Hz), 8.22 (1H, dt, J 6.0, 0.9 Hz), 8.08 (1H, d, J 5.8 Hz), 7.66 (2H, d, J 8.6 Hz), 7.26 (2H, d, J 8.6 Hz), 7.24 (1H, d, J 5.9 Hz), 4.50 (1H, m), 4.24 (2H, q, J 7.1 Hz), 3.30 (1H, m), 3.03 (1H, dd, J 13.7, 9.7 Hz), 2.44 (1H, m), 2.30–2.05 (3H, m), 1.60 (3H, s), 1.29 (3H, t, J 7.1 Hz). m/z (ESI, 70V) 431 (MH+.

In a similar manner to Example 5 from (S)-ethyl-3-[4-[(2,6-naphthyridin-1-yl)amino]phenyl]-2-aminopropionate and the appropriate dione were prepared Examples 6–16.

EXAMPLE 6

(2S)-Ethyl-3-[4-(2,6-naphthyridin-1-yl)amino)phenyl]-2-[(2-ethyl-3-oxo-1-cyclopentenyl)amino]propionate Prepared from 2-ethyl-1,3-cyclopentanedione. δ H (CD$_3$OD) 9.13 (1H, s), 8.57 (1H, d, J 5.9 Hz), 8.22 (1H, d, J 6.0 Hz), 8.08 (1H, d, J 5.8 Hz), 7.67 (22H, d, J 8.5 Hz), 7.26 (2H, d, J 8.5 Hz), 7.25 (1H, d, J 5.0 Hz), 4.48 (1H, m), 4.25 (2H, q, J 7.1 Hz), 3.31 (1H, m), 3.05 (1H, m), 2.48 (1H, m), 2.25–2.05 (5H, m), 1.30 (3H, t, J 7.1 Hz), 0.93 (3H, t, J 6.5 Hz). m/z (ESI, 70V) 445 (MH$^+$).

EXAMPLE 7

(2S)-Ethyl-3-[4-(2,6-naphthyridin-1-yl)amino)phenyl]-2-[(2-allyl-3-oxo-1-cyclohexenyl)amino]propionate Prepared from 2-allyl-1,3-cyclohexanedione. δ H (CDl$_3$) 9.16 (1H, s), 8.62 (1H, d, J 5.9 Hz), 8.20 (1H, d, J 5.6 Hz), 7.88 (1H, d, J 5.8 Hz), 7.73 (2H, d, J 8.3 Hz), 7.18 (1H, d, J 5.8 Hz), 7.12 (2H, d, J 8.3 Hz), 5.68 (1H, m), 4.98 (2H, m), 4.36 (1H, m), 4.23 (2H, q, J 7.1 Hz), 3.25–2.95 (4H, m), 2.40–1.70 (6H, 3×m), 1.30 (3H, t, J 7.1 Hz). m/z (ESI, 70V) 471 (MH$^+$).

EXAMPLE 8

(2S)-Ethyl-3-[4-(2,6-naphthyridin-1-yl)amino)phenyl]-2-[(5-phenyl-3-oxo-1-cyclohexenyl)amino]propionate Prepared from 5-phenyl-1,3-cyclohexanedione. δ H (CDl$_3$) 9.19 (1H, s), 8.70 (1H, 2×d J 5.8 Hz), 8.16–8.15 (1H, 2×d, J 5.1 Hz), 8.01 (1H, br), 7.66—7.61 (2H, 2×d, J 8.4 Hz), 7.35–7.05 (9H, m), 5.20 (1H, br), 4.24–4.22 (2H, 2×q, J 7.1 Hz), 3.34 (1H, m), 3.25 (1H, m), 3.05 (1H, m), 2.80–2.40 (4H, m), 1.32–1.30 (3H, 2×t, J 7.1 Hz). m/z (ESI, 70V) 507 (MH$^+$).

EXAMPLE 9

(2S)-Ethyl-3-[4-(2,6-naphthyridin-1-yl)amino)phenyl]-2-[(5-propyl-3-oxo-1-cyclohexenyl)amino]propionate Prepared from 5-propyl-1,3-cyclohexanedione 4 Å sieves replaced with Na$_2$SO$_4$ (~1 g) and acetic acid (1 drop). δ H (CD$_3$OD) 9.13 (1H, s), 8.57 (1H, d, J 6.0 Hz), 8.23 (1H, d, J 6.0 Hz), 8.09 (1H, d, J 5.8 Hz), 7.68 (2H, d, J 8.4 Hz), 7.24 (3H, m), 4.33 (1H, m), 4.16 (2H, m), 3.18 (1H, m), 3.05 (1H, m), 2.60–1.90 (3H, m), 1.35 (4H, br), 1.23–1.22 (3H, 2×t, J 7.1 Hz), 0.91 (3H, t). m/z (ESI, 70V) 473 (MH$^+$).

EXAMPLE 10

(2S)-Ethyl-3-[4-(2,6-naphthyridin-1-yl)amino)phenyl]-2-[(2-benzyl-3-oxo-1-cyclopentenyl)amino]propionate Prepared from Intermediate 1. δ H (CD$_3$OD) 9.15 (1H, s), 8.59 (1H, d, J 6.0 Hz), 8.24 (1H, d, J 6.0 Hz), 8.12 (1H, d, J 5.8 Hz), 7.62 (2H, d, J 18.4 Hz), 7.30–7.00 (8H, m), 4.48 (1H, m), 4.21 (2H, q, J 7.0 Hz), 3.52 (2H, m), 3.25 (1H, m), 2.95 (1H, m), 2.53 (1H, m), 2.30–2.05 (3H, m), 1.27 (3H, t, J 7.0 Hz). m/z (ESI, 70V) 507 (MH$^+$).

EXAMPLE 11

(2S)-Ethyl-3-[(2,6-naphthyridin-1-yl)amino)phenyl]-2-[(2-allyl-3-oxo-1-cyclopentenyl)amino]propionate Prepared from Intermediate 2. δ H (CD$_3$OD) 9.14 (1H, s), 8.58 (1H, d, J 6.0 Hz), 8.23 (1H, d, J 5.9 Hz), 8.09 (1H, d, J 5.8 Hz), 7.67 (2H, d, J 8.5 Hz), 7.25 (1H, d, J 5.9 Hz), 7.23 (2H, d, J 8.5 Hz), 5.74 (1H, m), 5.00 (2H, m), 4.52 (1H, m), 4.24 (2H, q, J 7.1 Hz), 3.30 (1H, m), 3.02 (1H, dd, J 13.8, 9.4 Hz), 2.89 (2H, d, J 5.9 Hz), 2.52 (1H, m), 2.30–2.05 (3H, m), 1.29 (3H, t, J 7.1 Hz). m/z (ESI, 70V) 457 (MH$^+$).

EXAMPLE 12

(2S)-Ethyl-3-[4-(2,6-naphthyridin-1-yl)amino) phenyl]-2-[(2-butyl-3-oxo-1-cyclopentenyl)amino] propionate Prepared from Intermediate 3 4 Å sieves replaced with $Na_2SO_4$ (~1 g) and acetic acid (1 drop). δ H ($CD_3OD$) 9.14 (1H, s), 8.57 (1H, d, J 6.0 Hz), 8.23 (1H, d, J 6.0 Hz), 8.09 (1H, d, J 5.8 Hz), 7.68 (2H, d, J 8.5 Hz), 7.26 (2H, d, J 8.5 Hz), 7.25 (1H, d), 4.50 (1H, dd), 4.25 (2H, q, J 7.1 Hz), 3.31 (1H, m), 3.05 (1H, dd), 2.45 (1H, m), 2.25–2.05 (5H, m), 1.30 (7H, m) 0.89 (3H, t). m/z (ESI, 70V) 473 (MH$^+$).

EXAMPLE 13

(2S)-Ethyl-3-[4-(2,6-naphthyridin-1-yl)amino) phenyl]-2-[(2-phenyl-3-oxo-1-cyclopentenyl)amino] propionate Prepared from Intermediate 4. δ H ($CD_3OD$) 9.14 (1H, d, J 0.9 Hz), 8.58 (1H, d, J 6.0 Hz), 8.24 (1H, d, 16.0 Hz), 8.11 (1H, d, 15.8 Hz), 7.68 (2H, m), 7.39 (2H, m), 7.26 (5H, m), 4.52 (1H, m), 4.24 (2H, q), 3.30 (1H, m), 3.07 (1H, m), 2.60 (1H, m), 2.45–2.20 (3H, m), 1.30 (3H, t). m/z (ESI, 70V) 493 (MH$^+$).

EXAMPLE 14

(2S)-Ethyl-3-[4-[2,6-naphthyridin-1-yl)amino) phenyl]-2-[(2-propyl-3-oxo-1-cyclopentenyl)amino] propionate Prepared from Intermediate 5. δ H ($CD_3OD$) 9.10 (1H, d, J 0.8 Hz), 8.55 (1H, d, J 6.0 Hz), 8.20 (1H, d, J 6.0 Hz), 8.07 (1H, d, J 5.8 Hz), 7.66 (2H, d, J 8.5 Hz), 7.24 (2H, d, J 8.5 Hz), 7.21 (1H, d), 4.47 (1H, dd, J 9.8, 4.6 Hz), 4.24 (2H, 1, J 7.1 Hz), 3.29 (1H, m), 3.04 (1H, dd, J 13.8, 9.8 Hz), 2.45 (1H, m), 2.25–2.07 (5H, m), 1.36 (2H, m, J 7.5 Hz), 1.29 (3H, t, J 7.1 Hz), 0.87 (3H, t, J 7.3 Hz). m/z (ESI, 70V), 459 (MH$^+$).

EXAMPLE 15

(2S)-Ethyl-3-[4-(2,6-naphthyridin-1-yl)amino) phenyl]-2-[(2-isopropyl-3-oxo-1-cyclopentenyl) amino]propionate Prepared from Intermediate 6 4 Å sieves replaced with $Na_2SO_4$ (~1 g) and acetic acid (1 drop) (240 mg, 41%). δ H ($CD_3OD$) 9.13 (1H, br), 8.55 (1H, br), 8.20 (1H, d), 8.09 (1H, d, J 5.8 Hz), 7.68 (2H, d, J 8.6 Hz), 7.24 (3H, d), 4.47 (1H, dd, J 9.3, 4.6 Hz), 4.25 (2H, q, J 7.1 Hz), 3.30 (1H, m), 3.07 (1H, dd, J 13.7, 9.3 Hz), 2.70 (1H, sept, J 7.1 Hz), 2.40 (1H, m), 2.25–2.05 (3H, m), 1.30 (3H, t, J 7.1 Hz), 1.16 (3H, d, J 7.1 Hz), 1.15 (3H, d, J 7.1 Hz). m/z (ESI, 70V) 459 (MH$^+$).

EXAMPLE 16

(2S)-Ethyl-3-[4-(2,6-naphthyridin-1-yl)amino) phenyl]-2-[(2-isobutyl-3-oxo-1-cyclopentenyl] amino]propionate Prepared from Intermediate 7, 4 Å sieves replaced with $Na_2SO_4$ sieves (~1 g) and acetic acid (1 drop) (50 mg, 20%). δ H ($CD_3OD$) 9.12 (1H, d, J 0.8 Hz), 8.57 (1H, d, J 6.0 Hz), 8.22 (1H, d, J 6.0 Hz), 8.08 (1H, d, J 5.8 Hz), 7.67 (2H, d, J 8.5 Hz), 7.24 (3H, d), 4.50 (1H, dd, J 9.6, 4.5 Hz), 4.24 (2H, q, J 7.1 Hz), 3.30 (1H, m), 3.05 (1H, dd, J 13.8, 9.7 Hz), 2.43 (1H, m), 2.25–2.05 (3H, m), 1.98 (2H, d, J 14.6 Hz), 1.74 (1H, sept), 1.29 (3H, t, J 7.1 Hz), 0.84 (3H, d, J 6.6 Hz), 0.83 (3H, d, J 6.6 Hz). m/z (ESI, 70V) 473 (MH$^+$).

EXAMPLE 17

(2S)-Ethyl-3-[4-(3-ethyl-isoquinolin-1-ylamino) phenyl]-2-[(2-ethyl-3-oxo-1-cyclopentenyl)amino] propionate A solution of (S)-ethyl-3-[4-(3-ethyl-isoquinol-1-yl amino)phenyl]-2-aminopropionate [prepared from 1-chloro, 3-ethyl-isoquinoline (from reaction of o-toluic acid with propionitrile and subsequent treatment with phosphorous oxychloride) and N-BOC-L-4-aminophenylalanine ethylester] (750 mg, 2.07 mmol) and 2-ethyl-1,3-cyclopentanedione (273 mg, 2.17 mmol) in 1,2-dichloroethane (10 ml) was treated with 4 Å sieves (~1 g) and heated at 90° for 3 days. The solution was filtered, concentrated in vacuo and the residue purified by chromatorgaphy ($SiO_2$, 100:1 DCM/MeOH) to give the title compound as a brown solid (511 mg, 52%). δ H ($d^6$-DMSO) 9.05 (1H, s), 8.46 (1H, d, J 7.0 Hz), 7.91 (2H, d, J 8.6 Hz), 7.72 (1H, d, J 7.0 Hz), 7.64 (1H, t, J 7.0 Hz), 7.51 (1H, t, J 7.0 Hz), 7.23 (2H, d, J 8.6 Hz), 6.99 (1H, s), 4.32 (1H, m), 4.15 (2H, q, J 7.1 Hz), 3.15 (1H, dd, J 13.5, 3.5 Hz), 3.01 (1H, dd, J 13.5, 9.6 Hz), 2.69 (2H, 1, J 7.5 Hz), 2.29 (1H, m), 2.18 (1H, m), 2.06 (4H, m), 1.28 (3H, t, J 7.5 Hz), 0.91 (3H, t, J 7.4 Hz). m/z (ESI, 70V) 472 (MH$^+$).

EXAMPLE 18

(2S)-3-[4-(3,5-Dichloropyrid-4-yl Carboxamido) phenyl]-2-[(3-oxo-1-cyclopentenyl)amino]propionic Acid A solution of Example 1 (170 mg, 0.37 mmol) in THF (2 ml) and water (2 ml) was treated with $LiOH.H_2O$ (23 mg, 0.55 mmol) and stirred for 30 mins. The mixture was concentrated in vacuo and purified by chromatography ($SiO_2$, DCM:MeOH:AcOH:$H_2O$ 200:20:3:2) to give the title compound as a white solid (134 mg, 84%). δ H ($d^6$-DMSO) 10.72 (1H, br, s), 8.65 (2H, s), 7.55 (1H, br, s), 7.42 (2H, d, J 8.4 Hz), 7.12 (2H, d, J 8.4 Hz), 4.64 (1H, s), 3.92 (1H, br, s), 2.94–2.81 (2H, m), 2.34 (2H, m), 1.97 (2H, t, J 5.5 Hz). m/z (ESI, 70V) 434 (MH$^+$).

In a similar manner to Example 18 were prepared Examples 19–34:

EXAMPLE 19

(2S)-3-[4-(3,5-Dichloropyrid-4-yl Carboxamido) phenyl]-2-[(3-oxo-1-cyclohexenyl)amino]propionic Acid Prepared from Example 2. δ H ($d^6$-DMSO) 10.95 (1H, br, s), 8.90 (2H, s), 7.64 (2H, d, J 8.3 Hz), 7.31 (2H, d, J 8.3 Hz), 7.0 (1H, br, s), 4.90 (1H, s), 3.97 (1H, br, s), 3.15 (1H, dd, J 13.6, 5.5 Hz), 3.06 (1H, dd, J 13.6, 6.8 Hz), 2.43–2.17 (4H, m), 1.89 (2H, m). m/z (ESI, 70V) 448 (MH$^+$).

EXAMPLE 20

(2S)-3-[(3,5-Dichloropyrid-4-yl Carboxamido) phenyl]-2-[(2-ethyl-3-oxo-1-cyclopentenyl)amino] propionic Acid Prepared from Example 3. δ H ($d^6$-DMSO) 10.86 (1H, s), 8.79 (2H, s), 7.55 (2H, d, J 8.3 Hz), 7.31 (2H, d, J 8.3 Hz), 7.08 (1H, d, J 9.1 Hz), 4.26 (1H, m), 3.17 (1H, dd, J 13.5, 4.2 Hz), 3.01 (1H, dd, J 13.5, 9.9 Hz), 2.31 (1H, dd, J 13.1, 5.0 Hz), 2.10–1.90 (5H, m), 0.81 (3H, t, J 7.4 Hz). m/z (ESI, 70V) 462 (MH$^+$).

EXAMPLE 21

(2S)-3-[4-(3,5-Dichloropyrid-4-ylcarboxamido) phenyl]-2-[(5,5-dimethyl-3-oxo-1-cyclohexenyl) amino]proponic Acid Prepared from Example 4. δ H (d$^6$-DMSO) 10.48 (1H, s), 8.70 (2H, s), 7.55 (2H, d, J 7.7 Hz), 7.26 (2H, d, J 7.7 Hz), 4.87 (1H, s), 4.12 (1H, s), 3.13 (1H, dd, J 13.9, 5.8 Hz), 3.01 (1H, dd, J 13.9, 7.6 Hz), 2.21 (2H, m), 1.97 (2H, s), 0.99 (3H, s), 0.96 (3H, s). m/z (ESI, 70V) 476 (MH$^+$).

EXAMPLE 22

(2S)-3-[4-[2,6-Naphthyridin-1yl)amino)phenyl]-2-[(2-methyl-3-oxo-1-cyclopentenyl)amino]propionic Acid Prepared from Example 5. δ H (d$^6$-DMSO) 9.28 (1H, s), 9.21 (1H, s), 8.66 (1H, d, J 5.9 Hz), 8.40 (1H, dd, J 6.0, 0.8 Hz), 8.13 (1H, d, J 5.7 Hz), 7.71 (2H, d, J 8.5 Hz), 7.25 (1H, d, J 5.7 Hz), 7.15 (2H, d, J 8.5 Hz), 6.56 (1H, d, J 8.1 Hz), 3.78 (1H, m), 3.11 (1H, d), 2.85 (1H, dd, J 13.3, 8.0 Hz), 2.31 (1H, m), 2.00–1.75 (3H, m), 1.44 (3H, s). m/z (ESI, 70V) 403 (MH$^+$).

EXAMPLE 23

(2S)-3-[4-(2,6-Naphthyridin-1-yl)amino)phenyl]-2-[(2-ethyl-3-oxo-1-cyclopentenyl)amino]propionic Acid Prepared from Example 6. δ H (d$^6$-DMSO) 9.30 (1H, s), 9.22 (1H, s), 8.67 (1H, d), 8.39 (1H, d), 8.14 (1H, d), 7.78 (2H, m), 7.28 (3H, m), 7.10 (1H, d), 4.28 (1H, m), 3.18 (1H, dd, J 13.6, 4.3 Hz), 3.01 (1H, dd, J 13.6, 10.0 Hz), 2.40–1.90 (6H, m), 0.83 (3H, t, J 7.4 Hz). m/z (ESI, 70V) 417 (MH$^+$).

EXAMPLE 24

(2S)3-[4-(2,6-Naphthyridin-1-yl)amino)phenyl]-2-[(2-allyl-3-oxo-1-cyclohexenyl)amino]propionic Acid Prepared from Example 7. δ H (d$^6$-DMSO) 9.31 (1H, s), 9.23 (1H, s), 8.68 (1H, d, J 5.9 Hz), 8.41 (1H, d, J 5.8 Hz), 8.14 (1H, d, J 5.7 Hz), 7.80 (2H, m), 7.28 (1H, d, J 5.7 Hz), 7.18 (2H, d, J 8.5 Hz), 5.77 (1H, d, J 8.7 Hz), 5.57 (1H, m), 4.93 (1H, dd, J 17.2, 1.8 Hz), 4.85 (1H, dd, J 10.0, 1.8 Hz), 4.42 (1H, br), 3.11 (1H, dd, J 13.7, 4.7 Hz), 3.07 (1H, dd, J 13.7, 8.0 Hz), 2.95 (2H, d, J 5.6 Hz), 2.31 (1H, m), 2.14 (1H, m), 2.06 (2H, m), 1.69 (2H, m). m/z (ESI, 70V) 443 (MH$^+$).

EXAMPLE 25

(2S)-3-[4-[2,6-Naphthyridin-1-yl)amino)phenyl]-2-[(5-phenyl-3-oxo-1-cyclohexenyl)amino]propionic Acid Prepared from Example 8. δ H (d$^6$-DMSO) 9.33 (1H, s), 9.23 (1H, s), 8.69 (1H, d, J 5.8 Hz), 8.41 (1H, d, J 5.8 Hz), 8.15 (1H, d, J 5.6 Hz), 7.32–7.20 (9H, m), 4.89 (1H, s), 4.10 (1H, m), 3.20 (2H, m), 3.09 (1H, dd, J 13.7, 5.2 Hz), 2.99 (1H, m), 2.72–2.23 (4H, m). m/z. (ESI, 70V) 479 (MH$^+$).

EXAMPLE 26

(2S)-3-[4-(2,6-Naphthyridin-1-yl)amino)phenyl]-2-[(5-propyl-3-oxo-1-cyclohexenyl]amino]propionic Acid Prepared from Example 9. δ H (d$^6$-DMSO) 9.40 (1H, d, J 0.7 Hz), 9.30 (1H, s), 8.86 (1H, d, J 5.9 Hz), 8.56 (1H, d, J 5.9 Hz), 8.35 (1H, d, J 5.7 Hz), 7.99 (2H, d, J 8.3 Hz), 7.43 (3H, m), 6.95 (1H, d, J 7.4 Hz), 4.31 (1H, m), 3.31 (1H, m), 3.16 (1H, m), 2.64 (1H, dt, J 15.5, 3.7 Hz), 2.37–2.00 (4H, m), 1.51 (4H, m), 1.08 (3H, dt, J 6.8, 1.9 Hz). m/z (ESI, 70V) 445 (MH$^+$).

EXAMPLE 27

(2S)-3-[4-[2,6-Naphthyridin-1-yl)amino)phenyl]-2-[(2-benzyl-3-oxo-1-cyclopentenyl)amino]propionic Acid Prepared from Example 10. δ H (d$^6$-DMSO) 9.30 (1H, s), 9.23 (1H, s), 8.68 (1H, d, J 5.9 Hz), 8.41 (1H, d, J 5.9 Hz), 8.16 (1H, d, J 5.7 Hz), 7.76 (2H, d), 7.29 (1H, d, J 5.8 Hz), 7.23–7.10 (6H, m), 7.09 (1H, m), 4.17 (1H, br), 3.39 (2H, m), 3.16 (1H, br, d), 2.94 (1H, br, d), 2.39 (1H, dd, J 16.3, 7.0 Hz), 2.15–1.92 (3H, m). m/z (ESI, 70V) 479 (MH$^+$).

EXAMPLE 28

(2S)-3-[4-(2,6-Naphthyridin-1-yl)amino)phenyl]-2-[(2-allyl-3-oxo-1-cyclopentenyl)amino]propionic Acid Prepared from Example 11. δ H (d$^6$-DMSO) 9.29 (1H, s), 9.22 (1H, s), 8.67 (1H, d, J 5.9 Hz), 8.39 (1H, d, J 5.9 Hz), 8.13 (1H, d, J 5.7 Hz), 7.76 (2H, m), 7.27 (1H, d, J 5.7 Hz), 7.22 (2H, d, J 8.5 Hz), 6.93 (1H, br), 5.69 (1H, m), 4.93 (1H, d, J 16.8 Hz), 4.86 (1H, dd, J 10.0, 2.0 Hz), 4.22 (1H, br), 3.14 (1H, dd, J 13.8, 4.3 Hz), 2.96 (1H, m), 2.78 (2H, d, J 4.3 Hz), 2.36 (1H, dd, J 16.8, 7.1 Hz), 2.10–1.90 (3H, m). m/z (ESI, 70V) 429 (MH$^+$).

EXAMPLE 29

(2S)-3-[4-(2,6-Naphthyridin-1-yl)amino)phenyl]-2-[(2-butyl-3-oxo-1-cyclopentenyl)amino]propionic Acid Prepared from Example 12. δ H (d$^6$-DMSO) 9.29 (1H, s), 9.22 (1H, s), 8.68 (1H, d, J 5.9 Hz), 8.40 (1H, dd, J 5.9, 1.0 Hz), 8.14 (1H, dd, J 5.7, 1.3 Hz), 7.79 (2H, d, J 8.5 Hz), 7.26 (3H, m), 6.97 (1H, br), 4.25 (1H, m), 3.17 (1H, dd, J 13.6, 3.9 Hz), 3.00 (1H, dd, J 13.0, 10.0 Hz), 2.32 (1H, m), 2.20–1.95 (5H, m), 1.21 (4H, m), 0.85 (3H, t, J 6.9 Hz). m/z (ESI, 70V) 445 (MH$^+$)

EXAMPLE 30

(2S)-3-[4-(2,6-Naphthyridin-1-yl)amino)phenyl]-2-[(2-phenyl-3-oxo-1-cyclopentenyl)amino]propionic Acid Prepared from Example 13. δ H (d$^6$-DMSO) 9.30 (1H, br), 9.23 (1H, d, J 0.6 Hz), 8.68 (1H, d, J 5.9 Hz), 8.39 (1H, d, J 5.9 Hz), 8.13 (1H, d, J 5.8 Hz), 7.80 (2H, d, J 8.5 Hz), 7.38–7.18 (8H, m), 6.70 (1H, d, J 8.9 Hz), 4.49 (1H, m), 3.17 (1H, m), 3.10 (1H, m), 2.59 (1H, m), 2.43 (1H, m), 2.25 (1H, m). m/z (ESI, 70V) 465 (MH$^+$).

EXAMPLE 31

(2S)-3-[4-(2,6-Naphthyridin-1-yl)amino)phenyl]-2-[(2-propyl-3-oxo-1-cyclopentenyl]amino]propionic Acid Prepared from Example 14. δ H (d$^6$-DMSO) 9.29 (1H, s), 9.22 (1H, s), 8.68 (1H, d, J 5.9 Hz), 8.39 (1H, dd, J 5.9, 0.9 Hz), 8.14 (1H, dd, J 5.6, 1.3 Hz), 7.78 (2H, m), 7.27 (3H, m), 7.05 (1H, d, J 9.4 Hz), 4.28 (1H, m), 3.18 (1H, dd, J 13.6, 4.3 Hz), 2.97 (1H, dd, J 13.6, 9.9 Hz), 2.33 (1H, m), 2.15–2.05 (5H, m), 1.26 (2H, hex, J 7.1 Hz), 0.82 (3H, t, J 7.3 Hz). m/z (ESI, 70V) 431 (MH$^+$).

EXAMPLE 32

(2S)-3-[4-(2,6-Naphthyridin-1-yl)amino)phenyl]-2-[(2-isopropyl-3-oxo-1-cyclopentenyl)amino] propionic Acid Prepared from Example 15. δ H (d$^6$-DMSO) 9.30 (1H, s), 9.23 (1H, s), 8.68 (1H, br), 8.40 (1H, d, J 5.7 Hz), 8.14 (1H, d, J 5.7 Hz), 7.79 (2H, m), 7.25 (3H, m), 6.79 (1H, d, J 9.4 Hz), 4.29 (1H, m), 3.17 (1H, dd, J 13.6, 4.4 Hz), 3.04 (1H, dd, J 13.5, 9.6 Hz), 2.69 (1H, sept, J 7.0 Hz), 2.27 (1H, m), 2.05–1.85 (3H, m), 1.09 (3H, d, J 7.1 Hz), 1.06 (3H, d, J 7.1 Hz). m/z (ESI, 70V) 431 (MH$^+$).

EXAMPLE 33

(2S)-3-[4-(2,6-Naphthyridin-1-yl)amino)phenyl]-2-[(2-isobutyl-3-oxo-1-cyclopentenyl)amino]propionic Acid Prepared from Example 16. δ H (d$^6$-DMSO) 9.29 (1H, s), 9.22 (1H, s), 8.67 (1H, d, J 5.9 Hz), 8.40 (1H, d, J 5.9 Hz), 8.13 (1H, d, J 5.7 Hz), 7.78 (2H, d, J 8.5 Hz), 7.24 (3H, m), 6.89 (1H, d, J 9.2 Hz), 4.22 (1H, m), 3.17 (1H, dd, J 13.6, 4.2 Hz), 2.99 (1H, dd, J 13.4, 9.6 Hz), 2.33 (1H, m), 2.07–1.88 (5H, m), 1.67 (1H, sept, J 6.6 Hz), 0.78 (3H, d, J 6.6 Hz), 0.77 (3H, d, J 6.6 Hz). m/z (ESI, 70V) 445 (MH$^+$).

EXAMPLE 34

(2S)-3-[4-(3-Ethylisoquinolin-1-ylamino)phenyl]-2-[(2-ethyl-3-oxo-1-cyclopentenyl)amino]propionic Acid Prepared from Example 17. δ H (d$^8$-DMSO) 9.04 (1H, s), 8.46 (1H, d, J 7.1 Hz), 7.87 (2H, d, J 8.5 Hz), 7.71 (1H, d, J 7.1 Hz), 7.64 (1H, t, J 7.1 Hz), 7.51 (1H, t, J 7.1 Hz), 7.23 (2H, d, J 8.6 Hz), 7.07 (1H, d, J 9.2 Hz), 6.98 (1H, s), 4.28 (1H, m), 3.16 (1H, dd, J 13.6, 4.3 Hz), 3.00 (1H, dd, J 13.6, 9.9 Hz), 2.69 (2H, q, J 7.5 Hz), 2.33 (1H, m), 2.06 (5H, m), 1.28 (3H, t, J 7.5 Hz), 0.84 (3H, t, J 7.3 Hz). m/z (ESI, 70V) 444 (MH$^+$).

EXAMPLE 35

(S)-Ethyl-3-[4-[(2,7-naphthyridin-1-yl)oxy]phenyl]-2-[(2-propyl-3-oxo-1-cyclopentenyl]amino] propionate A solution of Intermediate 21 (355 mg, 1.01 mmol) and Intermediate 5 (156 mg, 1.11 mmol) in nitromethane (5 ml) with Na$_2$SO$_4$ (~0.5 g) and acetic acid (2 drops) was heated for 2 days at 90°. The solution was filtered, filtrate concentrated in vacuo and residue purified by silica chromatography (SiO$_2$;0.4% MeOH in DCM) to give the title compound as an off white solid (222 mg 46%). δ H (DMSO) 9.43 (1H, s), 8.56 (1H, d, J 5.7 Hz), 7.59 (1H, d, J 5.8 Hz), 7.23 (1H, s), 7.20 (2H, d, J 8.3 Hz), 7.06 (2H, d, J 8.4 Hz), 7.05 (1H, d), 4.28 (1H, m), 3.99 (2H, q, J 7.1 Hz), 3.07 (1H, dd, J 13.6, 5.2 Hz), 2.94 (1H, dd, J 13.5, 9.8 Hz), 2.19 (3H, s), 2.20–1.84 (6H, m), 1.09 2H, m), 1.03 (3H, t, J 7.1 hz), 0.64 (3H, t, J 4.7 Hz). m/z (ESI, 70V) 474 (MH$^+$).

In a similar manner to Example 35 were prepared Examples 36 to 48.

EXAMPLE 36

(S)-Ethyl-3-[4-(2,6-naphthyridin-1-yl)amino] phenyl]-2-[(1-ethylpropyl)-3-oxo-1-cyclopentenyl) amino]propionate Prepared from (S)-ethyl-3-[4-[(2,6-naphthyrid-1-yl) amino]phenyl]-2-aminopropionate and Intermediate 8. δ H (DMSO-d$^6$) 9;30–9.20 (2H, m), 8.70 (1H, m), 8.40 (1H, br), 8.10 (1H, br m) 7.80 (2H, m), 7.20 (3H, m), 4.50 (1H, m), 4.10 (2H, m), 3.20–3.00 (2H, m), 2.30–2.00 (5H, m), 1.60 (2H, m), 1.40 (2H, m), 1.20 (3H, m), 0.80 (6H, t, J 7.5 Hz). m/z (ESI. 70V) 487 (MH$^+$).

EXAMPLE 37

(S)-Ethyl-3-[(4-(3-methyl-2,7-naphthyridin-1-yl) oxy]phenyl-2-[(2-isobutyl-3-oxo-1-cyclopentenyl) amino]propionate Prepared from Intermediates 21 and 7. δ H (DMSO-d$^6$) 9.60 (1H, s), 8.73 (1H, d, J 5.7 Hz), 7.76 (1H, d, J 5.8 Hz), 7.39 (2H, d), 7.37 (1H, s), 7.22 (2H, d), 7.13 (1H, d), 4.47 (1H, m), 4.15 (2H, q, J 7.1 Hz), 3.24 (1H, dd), 3.09 (1H, dd, J 13.7, 10.0 Hz), 2.35 (1H, m), 2.35 (3H, s), 2.20–2.00 (3H, m), 1.91 (1H, d), 1.68 (1H, seq, t), 1.20 (3H, t, J 7.1 Hz), 0.78 (3H, d, J 6.6 Hz), 0.78 (3H, d, J 6.6 Hz). m/z (ESI, 70V) 488 (MH$^+$).

EXAMPLE 38

(S)-Ethyl-3-[(4-(2,7-naphthyridin-1-yl)oxy]phenyl]-2-[(2-propyl-3-oxo-1-cyclopentenyl)amino] propionate Prepared from Intermediates 14 and 5. δ H (DMSO-d$^6$) 9.71 (1H, s), 8.83 (1H, d, J 5.7 Hz), 8.13 (1H, d, J 5.8 Hz), 7.91 (1H, d), 7.56 (1H, d, J 5.9 Hz), 7.41 (2H, d, J 8.5 Hz), 7.24 (3H, d), 4.46 (1H, m), 4.18 (2H, q, J 7.1 Hz), 3.25 (1H, dd, J 13.6, 5.0 Hz), 3.11 (1H, dd, J 13.5, 9.8 Hz), 2.34 (1H, m), 2.17–2.00 (5H, m), 1.27 (2H, m), 1.23 (3H, t, J 7.1 Hz), 0.82 (3H, t, J 7.3 Hz). m/z (ESI, 70V) 460 (MH$^+$).

EXAMPLE 39

(S)-Ethyl-3-[(4-(2,7-naphthyridin-1-yl)oxy]phenyl]-2-[(2-isobutyl-3-oxo-1-cyclopentenyl)amino] propionate Prepared from Intermediates 14 and 7. δ H (DMSO-d$^6$) 9.74 (1H, s), 8.87 (1H, d, J 5.7 Hz), 8.17 (1H, d, J 5.8 Hz), 7.95 (2H, d, J 5.8 Hz), 7.59 (1H, d, J 5.8 Hz), 7.44 (2H, d, J 8.5 Hz), 7.27 (2H, d, J 8.5 Hz), 7.19 (1H, d, J 9.6 Hz), 4.52 (1H, m), 4.21 (2H, q, J 7.1 Hz), 3.30 (1H, dd, J 13.6, 5.0 Hz), 3.15 (1H, dd, J 13.6, 9.9 Hz), 2.56 (1H, m), 2.39–2.04 (3H, m), 1.97 (2H, d), 1.73 (1H, sept, J 6.7 Hz), 1.26 (2H, t, J 7.1 Hz), 0.83 (3H, d, J 6.6 Hz), 0.82 (3H, d, J 6.6 Hz). m/z (ESI, 70V) 474 (MH$^+$).

EXAMPLE 40

(S)-Ethyl-3-[(4-(2,7-naphthyridin-1-yl)amino] phenyl]-2-[(2-isobutyl-3-oxo-1-cyclopentenyl) amino]propionate Prepared from Intermediates 13 and 7. δ H (DMSO-d$^6$) 9.84 (1H, s), 8.67 (1H, d, J 5.6 Hz), 8.17 (1H, d), 7.78 (2H, m), 7.70 (1H, d, J 5.6 Hz), 7.27 (2H, d, J 8.5 Hz), 7.14 (1H, d, J 5.7 Hz), 7.09 (1H, d, J 9.4 Hz), 4.42 (1H, m), 4.16 (2H, q, J 7.1 Hz), 3.18 (1H, m), 4.16 (2H, q, J 7.1 Hz), 3.18 (1H, dd, J 13.6, 4.9 Hz), 3.05 (1H, dd, J 13.6, 9.7 Hz), 2.36 (1H, m), 2.17–1.97 (5H, m), 1.69 (1H, m), 1.22 (3H, t, J 7.1 Hz), 0.80 (6H, d, J 6.6 Hz). m/z (ESI, 70V), 473 (MH$^+$).

EXAMPLE 41

(S)-Ethyl-3-[(4-(3-methyl-2,7-Naphthyridin-1-yl) amino]phenyl]-2-[(2-isobutyl-3-oxo-1-cyclopentenyl)amino]propionate Prepared from Intermediates 18 and 7 as an orange solid. δ H (DMSO-d$^6$) 8.57 (1H, d), 7.87 (2H, d, J 8.3 Hz), 7.57

(1H, d), 7.25 (2H, d, J 8.4 Hz), 7.14 (1H, d), 6.97 (1H, s), 4.45 (1H, m), 4.17 (2H, q, J 7.4 Hz), 3.17 (1H, dd, J 14.2, 4.9 Hz), 3.05 (1H, dd, J 14.2, 10.2 Hz), 2.44 (3H, s), 2.37 (1H, m), 2.16 (1H, m), 2.05 (2H, m), 1.92 (2H, d), 1.70 (1H, m), 1.21 (3H, t), 0.79 (6H, d); m/z (ESI, 70V) 487 (MH⁺).

EXAMPLE 42

(S)-Methyl-3-(4-[2',6'-dimethoxy]biphenylyl)-2-[(2-isobutyl-3-oxo-1-cyclopentenyl)amino]propionate Prepared from the free amino of Intermediate 24 and Intermediate 7. δ H (DMSO-d⁶) 7.26 (3H, m), 7.14 (2H, d, J 8.2 Hz), 6.75 (2H, d, J 8.4 Hz), 6.68 (1H, d, J 9.5 Hz), 4.48 (1H, m), 3.73 (1H, s), 3.65 (1H, s), 3.25 (1H, dd, J 13.7, 5.0 Hz), 3.10 (1H, dd, J 13.7, 9.3 Hz), 2.35 (1H, m), 2.13–1.99 (3H, m), 1.95 (2H, d, J 7.2 Hz), 1.77 (1H, seq, J 6.81 Hz), 0.82 (3H, d, J 6.7 Hz), 0.81 (3H, d, J 6.6 Hz). m/z (ESI, 70V) 452 (MH⁺).

EXAMPLE 43

Ethyl-3-[4-(3,5-dichloropyrid-4-ylcarboxamido)phenyl]-3-[(2-ethyl-3-oxo-1-cyclopentenyl)amino]propionate Prepared from Ethyl-3-[4-({3,5-dichloropyrid-4-yl}carboxamido)phenyl]-3-aminopropionate and 2-ethyl-cyclopentane-1,3-dione. δ H (DMSO-d⁶), 8.81 (2H, s), 7.64 (2H, d), 7.51 (1H, d), 7.45 (2H, d), 5.00 (1H, m), 4.10 (2H, q, J 7.1 Hz), 3.05 (1H, dd), 2.84 (1H, dd), 2.64 (1H, m), 2.31 (1H, m), 2.09 (4H, m), 1.17 (3H, t, J 7.09 Hz), 0.86 (3H, t, J 7.3 Hz). m/z (ESI, 70V) 491 (MH⁺).

EXAMPLE 44

Ethyl-3-[4-({3,5-dichloropyrid-4-yl}carboxamido)phenyl]-3-[(2-propyl-3-oxo-1-cyclopentenyl)amino]propionate Prepared from ethyl-3-[4-({3,5-dichloropyrid-4-yl}carboxamido)phenyl]-3-aminopropionate and Intermediate 5. δ H (DMSO-d⁶), 8.89 (2H, s), 7.66 (2H, d), 7.47 (2H, d), 5.03 (1H, m), 4.11 (2H, q, J 7.3 Hz), 3.08 (1H, dd), 2.88 (1H, dd), 2.73 (1H, m), 2.35 (1H, m), 2.09 (4H, m), 1.35 (2H, quin, J 7.13, 4.73 Hz), 1.16 (3H, t, J 7.1 Hz), 0.88 (3H, t, J 7.2 Hz). m/z (ES⁺, 70V) 505 (MH⁺).

EXAMPLE 45

Ethyl-3-[4-({3,5-dichloropyrid-4-yl}carboxamido)phenyl]-3-[(2-isobutyl-3-oxo-1-cyclopentenyl)amino]propionate Prepared from ethyl-3-[4-({3,5-dichloropyrid-4-yl}carboxamido)phenyl]-3-aminopropionate (prepared according to the methods of International Patent Application WO 00/32575) and Intermediate 7. δ H (DMSO-d⁶), 8.83 (2H, s), 7.65 (2H, d), 7.46 (2H, d), 7.40 (1H, d), 5.01 (1H, m), 4.12 (2H, q, J 7.14 Hz), 2.98 (1H, m), 2.81 (2H, m), 2.33 (1H, m), 2.17 (2H, m), 1.99 (2H, m), 1.78 (1H, m), 1.17 (3H, t, J 7.1 Hz), 0.85 (6H, d, J 6.55 Hz). m/z (ES⁺, 70V) 519 (MH⁺).

EXAMPLE 46

Methyl-3-[4-({3,5-dichloropyrid-4-yl}carboxamido)phenyl]-3-[(2-butyl-3-oxo-1-cyclopentenyl)amino]propionate Prepared from methyl-3-[4-({3,5-dichloropyrid-4-yl}carboxamido)phenyl]-3-amino propionate (prepared according to the methods in International Patent Application WO 00/18759) and Intermediate 3. δ H (DMSO-d⁶) 8.80 (2H, s), 7.60 (2H, d), 7.42 (2H, d), 7.38 (1H, d), 4.98 (1H, m), 3.62 (3H, s), 3.05 (1H, dd), 2.87 (1H, dd), 2.38–1.95 (6H, m), 1.21 (4H, m), 0.42 (3H, t). m/z (ESI, 70V) 504 (MH⁺).

EXAMPLE 47

Methyl-3-[4-(3,5-dichloropyrid-4-ylcarboxamido)phenyl]-3-[(2-phenyl-3-oxo-1-cyclopentenyl)amino]propionate Prepared from Methyl-3-[4-(3,5-dichloropyrid-4-yl carboxamido)phenyl]-3-aminopropionate and intermediate 4. δ H (CD₃OD) 8.66 (2H, s), 7.73–7.17 (9H, 3×m), 5.22 (1H, br), 3.77 (3H, s), 3.10–2.90 (2H, m), 2.57–2.45 (4H, m). m/z (ESI, 70V) 523 (MH⁺).

EXAMPLE 48

Ethyl-3-[4-(3{,5-Dichloropyrid-4-yl}carboxamido)phenyl]-3-[(5-propyl-3-oxo-1-cyclohexenyl)amino]propionate Prepared from ethyl-3-[4-({3,5-dichloropyrid-4-yl}carboxamido)phenyl]-3-amino-propionate and 5-propyl-1,3-cyclohexanedione. δ H (DMSO-d⁶), 8.80 (2H, s), 7.56 (2H, d), 7.46 (1H, d), 7.36 (2H, d), 4.71 (1H, m), 4.08 (2H, q, J 7.4 Hz), 2.86 (1H, m), 2.74 (1H, m), 2.38 (1H, m), 2.09 (2H, m), 1.81 (2H, m), 1.32 (4H, m), 1.18 (3H, t), 0.88 (3H, t). m/z (ES⁺, 70V) 519 (MH⁺).

In a similar manner to Example 18 were prepared Examples 49–62.

EXAMPLE 49

(S)-3-[4-[(3-Methyl-2,7-naphthyridinyl)oxy]phenyl]-2-[(2-propyl-3-oxo-1-cyclopentenyl)amino]propionic Acid Prepared from Example 35. δ H (DMSO-d⁶) 9.34 (1H, s), 9.27 (1H, s), 8.72 (1H, d, J 5.8 Hz), 8.45 (1H, d, J 5.9 Hz), 8.18 (1H, d, J 5.7 Hz), 7.80 (2H, d, J 8.4 Hz), 7.32 (1H, d, J 5.7 Hz), 7.24 (2H, d, J 8.4 Hz), 6.67 (1H, d, J 8.8 Hz), 4.15 (1H, br), 3.17 (1H, dd, J 13.5, 4.1 Hz), 3.01 (1H, dd, J 13.2, 8.5 Hz), 2.38 (1H, m), 2.21 (1H, m), 2.20–1.90 (3H, m), 1.75–1.60 (2H, m), 1.60–1.40 (2H, m), 0.78 (3H, t, J 7.1 Hz), 0.77 (3H, t, J 7.4 Hz); m/z (ESI, 70V) 459 (MH⁺).

EXAMPLE 50

(S)-3-[4-[(2,6-Naphthyridinyl)amino]phenyl]-2-[(2-(1-ethylpropyl)-3-oxo-1-cyclopentenyl)amino]propionic Acid Prepared from Example 36. δ H (DMSO-d⁶) 9.82 (1H, s), 8.75 (1H, d, J 5.7 Hz), 7.98 (1H, d, J 5.8 Hz), 7.43 (3H, d), 7.30 (1H, d), 4.56 (1H, m), 3.47 (1H, dd, J 13.6, 4.3 Hz), 3.29 (1H, dd, J 13.6, 10.2 Hz), 2.58 (3H, s), 2.55 (1H, m), 2.30–2.20 (5H, m), 1.47 (2H, m), 1.02 (3H, t, J 7.2 Hz). m/z (ESI, 70V) 446 (MH⁺).

EXAMPLE 51

(S)-3-[(4-[3-Methyl-2,7-naphthyridinyl]oxy)phenyl]-2-[(2-iosobutyl-3-oxo-1-cyclopentenyl)amino]propionic Acid Prepared from Example 37. δ H (DMSO-d⁶) 9.61 (1H, s), 8.74 (1H, d, J 5.7 Hz), 7.77 (1H, d, J 5.7 Hz), 7.39 (2H, d, J 8.3 Hz), 7.37 (1H, s), 7.22 (2H, d, J 8.3 Hz), 7.06 (1H, d, J 9.7 Hz), 4.38 (1H, m), 3.26 (1H, dd ???), 3.09 (1H, dd, J 13.4, 10.3 Hz), 2.33 (3H, s), 2.37 (1H, m), 2.10–1.85 (5H, m), 1.68 (1H, m), 0.78 (6H, m). m/z (ESI, 70V) 460 (MH$^+$).

EXAMPLE 52

(S)-3-[(4-(2,7-Naphthyridin-1-yl)oxy)phenyl]-2-[(2-propyl-3-oxo-1-cyclopentenyl)amino]propionic Acid Prepared from Example 38. δ H (DMSO-d$^6$) 9.71 (1H, s), 9.83 (1H, d, J 5.7 Hz), 8.14 (1H, d, J 5.8 Hz), 7.91 (1H, d, J 5.8 Hz), 7.55 (1H, d, J 5.8 Hz), 7.41 (2H, d, J 8 Hz), 7.23 (2H, d, J 8.5 Hz), 7.05 (1H, d), 4.36 (1H, m), 3.26 (1H, dd), 3.08 (1H, dd, J 13.5, 19.2 Hz), 2.33 (1H, m), 2.01 (5H, m), 1.27 (2H, m), 0.82 3H, t, J 7.3 Hz). m/z (ESI, 70V) 432 (MH$^+$).

EXAMPLE 53

(S)-3-[(4-(2,7-Naphthyridin-1-yl)oxy)phenyl]-2-[(2-isobutyl-3-oxo-1-cyclopentenyl)amino]propionic Acid Prepared from Example 39. δ H (DMSO-d$^6$) 9.70 (1H, s), 8.83 (1H, d, J 5.7 Hz), 8.13 (1H, d, J 5.8 Hz), 7.90 (1H, d, J 5.7 Hz), 7.55 (1H, d, J 5.8 Hz), 7.40 (2H, d, J 8.4 Hz), 7.22 (2H, d, J 5.8 Hz), 7.05 (1H, d), 4.38 (1H, m), 3.27 (1H, m) 3.08 (1H, dd, J 13.5, 10.1 Hz), 2.36 (1H, m), 2.06 (3H, m), 1.91 (2H, d), 1.69 (1H, m), 0.79 (3H, d, J 6.6 Hz), 0.78 (3H, d, J 6.6 Hz). m/z (ESI, 70V) 446 (MH$^+$).

EXAMPLE 54

(S)-3-[4-[(2,7-Naphthyridin-1yl)amino]phenyl]-2-[(2-isobutyl-3-oxo-1-cyclopentenyl)amino]propionic Acid Prepared from Example 40. δ H (DMSO-d$^6$) 9.83 (1H, s), 9.52 (1H, s), 8.66 (1H, d, J 5.6 Hz), 8.16 (1H, d, J 5.7 Hz), 7.73 (2H, d, J 8.4 Hz), 7.69 (1H, d, J 5.6 Hz), 7.22 (2H, d, J 8.4 Hz), 7.13 (1H, d, J 5 Hz), 4.13 (1H, br), 3.15 (1H, dd, J 13.6, 3.7 Hz), 2.97 (1H, dd, J 13.2, 9.2 Hz), 2.36 (1H, m), 2.10–1.88 (5H, m), 1.69 (1H, m), 0.80 (3H, d, J 6.3 Hz), 0.79 (3H, d, J 6.4 Hz). m/z (ESI, 70V) 445 (MH$^+$).

EXAMPLE 55

(S)-3-[4-[(3-Methyl-2,7-naphthyridin-1-yl)amino] phenyl]-2-[(2-isobutyl-3-oxo-1-cyclopentenyl) amino]propionic Acid Prepared from Example 41. δ H (DMSO-d$^6$) 8.55 (1H, d), 7.86 (2H, d, J 8.2 Hz), 7.56 (1H, d), 7.24 (2H, d, J 8.3 Hz), 7.15 (1H, d), 6.96 (1H, s), 4.43 (1H, m), 3.17 (1H, dd, J 14.1, 5.8 Hz), 3.04 (1H, dd, J 14.1, 10.1 Hz), 2.43 (3H, s), 2.36 (1H, m), 2.15 (1H, m), 1.91 (2H, d), 1.71 (1H, m), 1.22 (3H, t), 0.78 (6H, d). m/z (ESI, 70V) 459 (MH$^+$).

EXAMPLE 56

(S)-3-[4-(-2',6'-Dimethoxy)biphenyl]-2-[(2-isobutyl-3-oxo-1-cyclopentenyl)amino]propionic Acid Prepared from Example 42. δ H (DMSO-d$^6$) 7.27 (3H, m), 7.09 (3H, d), 6.72 (2H, d, J 8.4 Hz), 4.36 (1H, m), 3.64 (6H, s), 3.24 (1H, dd, J 13.6, 4.2 Hz), 3.03 (1H, dd, J 13.6, 10.2 Hz), 2.32 (1H, m), 2.06 (1H, m), 1.97–1.91 (4H, m), 1.72 (1H, m), 0.79 (6H, d, J 6.5 Hz). m/z (ESI, 70V) 438 (MH$^+$).

EXAMPLE 57

3-[4-[(3,5-Dichloropyrid-4-yl)carboxamido]phenyl]-3-[[(2-ethyl-3-oxo-1-cyclopentenyl)amino]propionic Acid Prepared from Example 43. δ H NMR (DMSO-d$^6$), 8.79 (2H, s), 7.62 (2H, d), 7.49 (1H, d), 7.42 (2H, d), 4.97 (1H, m), 3.03 (1H, dd), 2.82 (1H, dd), 2.62 (1H, m), 2.29 (1H, m), 2.07 (4H, m), 0.85 (3H, t, J 7.3 Hz). m/z (ES$^+$, 70V) 463 (MH$^+$).

EXAMPLE 58

3-[4-[3,5-Dichloropyrid-4-yl)carboxamido]phenyl]-3-[(2-propyl-3-oxo-1-cyclopentenyl)amino] propionic Acid Prepared from Example 44. δ H NMR (DMSO-d$^6$), 8.85 (2H, s), 7.63 (2H, d), 7.45 (2H, d), 4.98 (1H, m), 3.04 (1H, dd), 2.85 (1H, dd), 2.71 (1H, m), 2.31 (1H, m), 2.05 (4H, m), 1.33 (2H, quin, J 7.13, 4.73 Hz), 0.89 (3H, t, J 7.2 Hz). m/z (ES$^+$, 70V) 477 (MH$^+$).

EXAMPLE 59

3-[4-[(3,5-Dichloropyrid-4-yl)carboxamido]phenyl]-3-[(2-isobutyl-3-oxo-1-cyclopentenyl]amino] propionic Acid Prepared from Example 45. δ H NMR (DMSO-d$^6$), 8.81 (2H, s), 7.63 (2H, d), 7.44 (2H, d), 7.38 (1H, d), 4.97 (1H, m), 2.96 (1H, m), 2.79 (2H, m), 2.31 (1H, m), 2.15 (2H, m), 1.96 (2H, m), 1.75 (1H, m), 0.82 (6H, d, J 6.54 Hz). m/z (ES$^+$, 70V) 491 (MH$^+$).

EXAMPLE 60

3-[4-[(3,5-Dichloropyrid-4-yl)carboxamido]phenyl]-3-[(2-butyl-3-oxo-1-cyclopentenyl)amino]propionic Acid Prepared from Example 46. δ H (DMSO-d$^6$) 10.89 (1H, s), 8.76 (2H, s), 7.58 (2H, d, J 8.5 Hz), 7.38 (3H, d), 4.90 (1H, m), 2.88 (1H, m), 2.71 (1H, dd, J 15.9, 4.9 Hz), 2.63 (1H, m), 2.21 (1H, m), 2.10–2.00 (4H, m), 1.20 (4H, br), 0.82 (3H, t, J 6.9 Hz). m/z (ESI, 70V) 489 (MH$^+$).

EXAMPLE 61

3-[4-[(3,5-Dichloropyrid-4-yl)carboxamido]phenyl]-3-[(2-phenyl-3-oxo-1-cyclopentenyl)amino] propionic Acid Prepared from Example 47. δ H (DMSO-d$^6$) 11.00 (1H, s), 8.85 (1H, s), 7.98 (1H, br), 7.70 (2H, d, J 8.0 Hz), 7.52 (2H, d, J 8.0 Hz), 7.41 (4H, m), 7.27 (1H, m), 5.12 (1H, br), 3.08 (1H, m), 2.88 (1H, m), 2.73 (1H, m), 2.49 (1H, m), 2.32 (2H, m). m/z (ESI, 70V) 510 (MH$^+$).

EXAMPLE 62

3-[4-[(3,5-Dichloropyrid-4-yl)carboxamido]phenyl]-3-[(5-propyl-3-oxo-1-cyclohexenyl)amino]propionic Acid Prepared from Example 48. δ H NMR (DMSO-d$^6$), 8.80 (2H, s), 7.60 (2H, d), 7.53 (1H, d), 7.35 (2H, d), 4.71 (1H, m), 2.81 (1H, m), 2.68 (1H, m), 2.40 (1H, m), 2.10 (2H, m), 1.81 (2H, m), 1.29 (4H, m), 0.88 (3H, t). m/z (ES$^+$, 70V) 491 (MH$^+$).

In a similar manner to Example 35 were prepared Examples 63–66:

EXAMPLE 63

Ethyl-3-[5-[(3-methyl-2,7-naphthyridin-1-yl)oxy]-pyridin-2-yl]-2-[(2-propyl-3-oxo-1-cyclopentenyl)amino]propionate Prepared from intermediates 29 and 5 δ H (CDCl$_3$) 9.72 (1H, s), 8.73 (1H, d, J 5.8 Hz), 8.59 (1H, d, J 2.6 Hz), 7.65 (1H, dd, J 8.4, 2.7 Hz), 7.54 (1H, d, J 5.8 Hz), 7.26 (1H, d, J 8.4 Hz), 7.17 (1H, s), 6.51 (1H, d, J 9.3 Hz), 4.67–4.61 (1H, symm, m), 4.20 (2H, q, J 7.1 Hz), 3.45–3.37 (2H, m), 2.45 (3H, s), 2.52–2.31 (4H, m), 2.14 (2H, qd, J 14.6, 7.5 Hz), 1.46 (2h, hextet, J 7.4 Hz), 1.23 (3H, t, J 7.1 Hz) and 0.92 (3H, t, J 7.3 Hz); m/z (ES$^+$, 70V) 475 (MH$^+$).

EXAMPLE 64

Ethyl-3-[5-[(3-methyl-2,7-naphthyridin-1-yl)oxy]-pyridin-2-yl]-2-[(2-isobutyl-3-oxo-1-cyclopentenyl)amino]propionate Prepared from Intermediates 29 and 7. δ H (CDCl$_3$) 9.63 (1H, s), 8.64 (1H, d, J 5.8 Hz), 8.51 (1H, d, J 2.7 Hz), 7.56 (1H, dd, J 8.4, 2.7 Hz), 7.45 (1H, dd, J 5.8, 0.7 Hz), 7.17 (1H, d, J 8.4 Hz), 7.08 (1H, s), 6.49 (1H, d, J 9.2 Hz), 4.59–4.52 (1H, m), 4.11 (2H, q, J 7.1 Hz), 3.34–3:32 (2H, m), 2.45–2.27 (4H, m), 2.37 (3H, s), 1.95 (2H, qd, J 13.9, 7.2 Hz), 1.75 (1H, m), 1.14 (3H, t, J 7.1 Hz), 0.82 (3H, d, J 6.2 Hz) and 0.80 (3H, d, J 6.2 Hz), m/z (ES$^+$, 70V) 489 (MH$^+$).

EXAMPLE 65

Ethyl-3-[5-[(3-methyl-2,7-naphthyridin-1-yl)oxy]-pyridin-2-yl]-2-[(2-ethyl-3-oxo-1-cyclopentenyl)amino]propionate Prepared from Intermediate 29 and 2-ethyl-1,3-cyclopentanedione. δ H (CDCl$_3$) 9.63 (1H, s), 8.64 (1H, d, J 5.8 Hz), 8.51 (1H, d, J 2.6 Hz), 7.56 (1H, dd, J 8.4, 2.7 Hz), 7.46 (1H, dd, J 5.8, 0.8 Hz), 7.18 (1H, d, J 8.4 Hz), 7.08 (1H, s), 6.34 (1H, d, J 9.3 Hz), 4.59–4.52 (1H, m), 4.12 (2H, q, J 7.1 Hz), 3.39–3.29 (2H, m), 2.37 (3H, s), 2.38–2.25 (4H, m), 2.17–2.03 (2H, m), 1.16 (3H, t, J 7.1 Hz) and 0.93 (3H, t, J 7.5 Hz); m/z (ES$^+$, 70V) 461 (MH$^+$).

EXAMPLE 66

(S)-Ethyl-3-[4-[(3,5-dichloropyrid-4-yl)carboxamide]phenyl]-2-[(-2-isobutyl-3-oxo-1-cyclopentenyl)amino]propionate Prepared from (S)-ethyl-3-[4-[(3,5-dichloropyrid-4-yl)carboxamido]phenyl]-2-aminopropionate and Intermediate 7. δ H (MeOD) 8.55 (2H, s), 7.50 (2H, d, J 8.5 Hz), 7.19 (2H, d, J 8.5 hz), 4.41 (1H, dd, J 9.8, 4.7 Hz), 4.16 (1H, q, J 7.2 Hz), 4.13 (1H, q, J 7.2 Hz), 3.23 (1H, dd, J 13.9, 4.6 Hz), 2.97 (1H, dd, J 13.9, 9.9 Hz), 2.38 (1H, m), 2.18 (3H, m), 1.88 (2H, d, J 7.3 Hz), 1.58 (1H, septet, J 6.9 Hz), 1.19 (3H, J 7.2 Hz), 0.72 (6H, dd, J 6.9, 1.5 Hz); m/z (ES$^+$, 70V) 518 (MH$^+$).

To a similar manner to Example 18 were prepared Examples 67–70.

EXAMPLE 67

3-[5-[(3-Methyl-2,7-naphthyridin-1-yl)oxy]-pyridin-2-yl]-2-[(2-propyl-3-oxo-1-cyclopentenyl)amino]propionic Acid Prepared from Example 63. δ H (DMSO-d$^6$) 9.65 (1H, s), 8.76 (1H, d, J 5.8 Hz), 8.55 (1H, d, J 2.7 Hz), 7.79 (1H, d, J 5.8 Hz), 7.77 (1H, dd, J 8.4, 2.7 Hz), 7.43 (1H, d, J 8.4 Hz), 7.41 (1H, s), 7.22 (1H, d, J 9.6 Hz), 4.65 (1H, narrow, m), 3.40 (1H, dd, J 14.1, 4.5 Hz), 3.31 91H, dd, J 14.1, 9 Hz), 2.43–2.37 (1H, m), 2.38 (3H, s), 2.27–2.22 (1H, m), 2.09–2.05 (2H, m), 2.04–1.9 (2H, m), 1.24 (2H, hextet, J 7.4 Hz), and 0.79 (3H, t, J 7.3 Hz); m/z (ES$^+$, 70V) 447 (MH$^+$).

EXAMPLE 68

3-[5-[(3-Methyl-2,7-naphthyridin-1-yl)oxy]-pyridin-2-yl]-2-[(2-isobutyl-3-oxo-1-cyclopentenyl)amino]propionic Acid Prepared from Example 64. δ H (DMSO-d$^6$) 9.65 (1H, s), 8.76 (1H, d, J 5.7 Hz), 8.57 (1H, d, J 2.7 Hz), 7.79 (1H, d, J 5.8 hz), 7.74 (1H, dd, J 8.4, 2.7 Hz), 7.41 (1H, s), 7.41 (1H, d, J 8.4 Hz), 7.11 (1h, d, J 9.3 Hz), 4.60 (1H, m), 3.40 (1H, m), 3.30 91H, m), 2.45–2.40 (1H, m), 2.37 (3H, s), 2.27–2.22 (1H, m), 2.15–2.00 (2H, m), 1.95–1.82 (2H, m), 1.65 (1H, m), 0.77 (3H, d, J 6.6 Hz), and 0.72 (3H, d, J 6.6 Hz), m/z (ES$^+$, 70V) 461 (MH$^+$).

EXAMPLE 69

3-[5-[(3-Methyl-2,7-naphthyridin-1-yl)oxy]-pyridin-2-yl]-2-[(2-ethyl-3-oxo-1-cyclopentenyl)amino]propionic Acid Prepared from Example 65. δ H (DMSO-d$^6$) 9.65 (1H, s), 8.76 (1H, d, J 5.7 Hz), 8.58 (1H, d, J 2.7 Hz), 7.80–7.76 (2H, overlapping signals), 7.44 (1H, d, J 8.5 Hz), 7.41 (1H, s), 7.24 (1H, d, J 9.5 Hz), 4.65 (1H, m), 3.40 (1H, dd, J 14.1, 4.5 Hz), 3.31 (1H, dd, J 14.1, 9.5 Hz), 2.43–2.39 (1H, m) 2.38 (3H, s), 2.26–2.20 (1H, m), 2.08–2.00 (4H, m) and 0.82 (3H, t, J 7.4 Hz); m/z (ES$^+$, 70V) 433 (MH$^+$).

EXAMPLE 70

(S)-3-[4-[(3,5-Dichloropyrid-4-yl)carboxamido)phenyl]-2-[(2-isobutyl-3-oxo-1-cyclopentenyl)amino]propionic Acid Prepared from Example 66. δ H (MeOD) 8.67 (2H, s), 7.59 (2H, d, J 8.5 Hz), 7.31 (2H, d, J 8.5 Hz), 4.46 (1H, dd, J 9.8, 4.2 Hz), 3.37 (1H, dd, J 13.9, 10.0 Hz), 2.50 (1H, dd, J 14.2, 4.9 Hz), 2.22 (3H, m), 1.99 (2H, d, J 5.2 Hz), 1.69 (1H, septet, J 6.6 Hz), 0.82 (6H, d, J 6.6 Hz). m/z (ES$^+$, 70V) 491 (MH$^+$).

EXAMPLE 71

(S)-Ethyl-3-[4-{(3-methyl-2,7-naphthyridin-1-yl)amino}phenyl]-2-[(2-cyclohexyl-3-oxo-1-cyclopentenyl)amino]propionate Prepared from the Intermediate 9 and the Intermediate 19 in a similar manner to Example 35. δ H (DMSO-d$^6$) 9.77 (1H, s), 9.47 (1H, s), 8.59 (1H, d, J 6.0 Hz), 7.88 (2H, d, J 4.0 Hz), 7.85 (1H, d, J 5.0 Hz), 7.84 (2H, d, J 3.0 Hz), 7.57 (1H, s), 7.24 (1H, d, J 8.0 Hz), 4.40 (1H, m), 4.18 (2H, q, J 7.0 Hz), 3.19 (1H, dd, J 14.0, 5.0 Hz), 3.08 (1H, dd, J 14.0, 9.0 Hz), 2.44 (3H, s), 2.35 (1H, m), 2.33 (1H, m), 2.29 (1H, m), 1.83 (3H, s), 1.80 (2H, m), 1.70 (5H, m), 1.63 (5H, m), 1.30 (3H, m). m/z (ES$^+$, 70V) 512 (MH$^+$).

EXAMPLE 72

(S)-3-[4-{(3-Methyl-2,7-naphthyridin-1-yl)amino}phenyl]-2-[(2-cyclohexyl-3-oxo-1-cyclopentenyl)amino]propionic Acid Prepared from Example 71 in a similar manner to Example 18. δ H (DMSO-d$^6$) 9.75 (1H, s), 8.58 (1H, d, J 6.0

Hz), 7.87 (2H, d, J 8.0 Hz), 7.54 (1H, d, J 6.0 Hz), 7.25 (2H, d, J 8.0 Hz), 6.96 (1H, s), 6.31 (1H, br, s), (4.27 (1H, m), 3.21 (1H, dd, J 14.0, 4.0 Hz), 3.09 (1H, dd, J 14.0, 8.0 Hz), 2.47 (3H, s), 2.39 (2H, m), 2.35 (3H, s), 2.08 (2H, m), 1.75 (5H, m), 1.39 (5H, m). m/z (ES$^+$, 70V) 485 (MH$^+$).

EXAMPLE 73

(S)-Ethyl-3-[4-{(3,5-dichloropyrid-4-yl) carboxamido}phenyl]-2-[(4,5-dihydro-1,1-dioxothiophen-3-yl)amino]propionate (S)-Ethyl-3-[4-{(3,5-dichloropyrid-4-yl) carboxamido}phenyl]-2-aminopropionate (500 mg, 1.3 mmol) was added to Intermediate 30 (340 mg, 2.54 mmol) in 1,2-DCE (5 ml) and 3 drops of glacial acetic acid added. The mixture was heated at 90° for 16 h, cooled, concentrated and purified by column chromatography (SiO$_2$; CH$_2$Cl$_2$/MeOH 100:1) to give the title compound (320 mg, 0.64 mmol, 49%) as an off white solid. δ H (DMSO-d$^6$) 10.89 (1H, s), 8.81 (2H, s), 7.59 (2H, d, J 8.5 Hz), 7.26 (2H, d, J 8.5 Hz), 7.20 (1H, d, J 8.2 Hz), 5.31 (1H, s, z), 4.04 (1H, m), 3.22 (2H, t, J 6.9 Hz), 3.05 (1H, dd, J 13.8, 6.0 Hz), 2.96 (1H, dd, J 13.8, 7.9 Hz), 2.82 (1H, dd, J 16.6, 6.5 Hz), 2.73 (1H, dd, J 16.6, 6.8 Hz), 1.18 (3H, t, J 7.1 Hz). m/z (ES$^+$, 70V), 498 (MH$^+$).

EXAMPLE 74

(S)-3-[4-{(3,5-Dichloropyrid-4-yl) carboxamido}phenyl]-2-[(4,5-dihydro-1,1-dioxothiophen-3-yl)amino]propionic Acid Prepared from Example 73 in a similar manner to Example 18. δ H (DMSO-d$^6$) 10.90 (1H, s), 8.81 (2H, s), 7.56 (2H, d, J 8.2 Hz), 7.23 (2H, d, J 8.2 Hz), 5.25 (1H, s), 3.89 (1H, m), 3.20 (2H, t, J 6.9 Hz), 3.05 (1H, dd, J 13.8, 5.7 Hz), 2.92 (1H, dd, J 13.8, 7.3 Hz), 2.76 (2H, m). m/z (ES$^+$, 70V) 470 (MH$^+$).

The following assays can be used to demonstrate the potency and selectivity of the compounds according to the invention. In each of these assays an IC$_{50}$ value was determined for each test compound and represents the concentration of compound necessary to achieve 50% inhibition of cell adhesion where 100%=adhesion assessed in the absence of the test compound and 0%=absorbance in wells that did not receive cells.

$\alpha_4\beta_1$ Integrin-degendent Jurkat Cell Adhesion to VCAM-Ig 96 well NUNC plates were coated with F(ab)$_2$ fragment goat anti-human IgG Fcy-specific antibody [Jackson Immuno Research 109-006-098: 100 μl at 2 μg/ml in 0.1M NaHCO$_3$, pH$_{8.4}$], overnight at 4°. The plates were washed (3x) in phosphate-buffered saline (PBS) and then blocked for 1 h in PBS/1% BSA at room temperature on a rocking platform. After washing (3x in PBS) 9 ng/ml of purified 2d VCAM-Ig diluted in PBS/1% BSA was added and the plates left for 60 minutes at room temperature on a rocking platform. The plates were washed (3x in PBS) and the assay then performed at 37° for 30 min in a total volume of 200 μl containing 2.5x10$^5$ Jurkat cells in the presence or absence of titrated test compounds.

Each plate was washed (2x) with medium and the adherent cells were fixed with 100 μl methanol for 10 minutes followed by another wash. 100 μl 0.25% Rose Bengal (Sigma R4507) in PBS was added for 5 minutes at room temperature and the plates washed (3x) in PBS. 100 μl 50% (v/v) ethanol in PBS was added and the plates left for 60 min after which the absorbance (570 nm) was measured.

$\alpha_4\beta_7$ Inteprin-dependent JY Cell Adhesion to MAdCAM-Ig

This assay was performed in the same manner as the $\alpha_4\beta_1$ assay except that MAdCAM-Ig (150 ng/ml) was used in place of 2d VCAM-Ig and a sub-line of the β-lympho blastoid cell-line JY was used in place of Jurkat cells. The IC$_{50}$ value for each test compound was determined as described in the $\alpha_4\beta_1$ integrin assay.

$\alpha_5\beta_1$ Inteprin-dependent K562 Cell Adhesion to Fibronectin 96 well tissue culture plates were coated with human plasma fibronectin (Sigma F0895) at 5 μg/ml in phosphate-buffered saline (PBS) for 2 hr at 37° C. The plates were washed (3x in PBS) and then blocked for 1 h in 100 μl PBS/1% BSA at room temperature on a rocking platform. The blocked plates were washed (3x in PBS) and the assay then performed at 37° C. in a total volume of 200 μl containing 2.5x10$^5$ K562 cells, phorbol-12-myristate-1 3-acetate at 10 ng/ml, and in the presence or absence of titrated test compounds. Incubation time was 30 minutes. Each plate was fixed and stained as described in the $\alpha_4\beta_1$ assay above.

$\alpha_m\beta_2$-Dependent Human Polymorphonuclear Neutrophils Adhesion to Plastic 96 well tissue culture plates were coated with RPMI 1640/10% FCS for 2 h at 37° C. 2x10$^5$ freshly isolated human venous polymorphonuclear neutrophils (PMN) were added to the wells in a total volume of 200 μl in the presence of 10 ng/ml phorbol-12-myristate-13-acetate, and in the presence or absence of test compounds, and incubated for 20 min at 37° C. followed by 30 min at room temperature. The plates were washed in medium and 100 μl 0.1% (w/v) HMB (hexadecyl trimethyl ammonium bromide, Sigma H5882) in 0.05M potassium phosphate buffer, pH 6.0 added to each well. The plates were then left on a rocker at room temperature for 60 min. Endogenous peroxidase activity was then assessed using tetramethyl benzidine (TMB) as follows: PMN lysate samples mixed with 0.22% H$_2$O$_2$ (Sigma) and 50 μg/ml TMB (Boehringer Mannheim) in 0.1M sodium acetate/citrate buffer, pH 6.0 and absorbance measured at 630 nm.

$\alpha IIb/\beta_3$-Dependent Human Platelet Aggregation

Human platelet aggregation was assessed using impedance aggregation on the Chronolog Whole Blood Lumiaggregometer. Human platelet-rich plasma (PRP) was obtained by spinning fresh human venous blood anticoagulated with 0.38% (v/v) tri-sodium citrate at 220xg for 10 min and diluted to a cell density of 6x10$^8$/ml in autologous plasma. Cuvettes contained equal volumes of PRP and filtered Tyrode's buffer (g/liter: NaCl 8.0; MgCl$_2$.H$_2$O 0.427; CaCl$_2$ 0.2; KCl 0.2; D-glucose 1.0; NaHCO$_3$ 1.0; NaHPO$_4$.2H$_2$O 0.065). Aggregation was monitored following addition of 2.5 μM ADP (Sigma) in the presence or absence of inhibitors.

In the above assays the preferred compounds of the invention in which R$^1$ is an $\alpha_4$ integrin binding group, such as the compounds of the Examples generally have IC$_{50}$ values in the $\alpha_4\beta_1$ and $\alpha_4\beta_7$ assays of 1 μM and below. In the other assays featuring α integrins of other subgroups the same compounds had IC$_{50}$ values of 50 μM and above thus demonstrating the potency and selectivity of their action against α$_4$ integrins.

What is claimed is:

1. A compound according to formula (1):

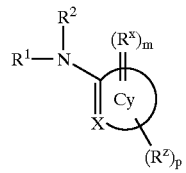

(1)

wherein

R$^1$ is a group Ar$^1$L$^2$Ar$^2$Alk- in which Ar$^1$ is an optionally substituted phenyl group, L$^2$ is a covalent bond or a linker atom or group, Ar$^2$ is an optionally substituted arylene or heteroarylene group and Alk is a chain —CH$_2$—CH(R)—, —CH═C(R)—,

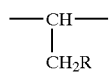

in which R is a carboxylic acid derivative or biostere;

R$^2$ is a hydrogen atom or a C$_{1-6}$alkyl group;

the ring Cy is an unsaturated cycloaliphatic or heterocycloaliphatic ring containing X, in which X is a N atom or a C(R$^w$) group;

R$^w$ is a group R$^z$;

R$^x$ which may be present or any available carbon atom of the ring Cy is a oxo (═O), thioxo (═S) or imino (═NR$^{30}$) group in which R$^{30}$ is an aliphatic, heteroaliphatic, cycloaliphatic, heterocycloaliphatic, aromatic or hetero-aromatic group;

m is zero or the integer 1, 2 or 3;

R$^z$ which may be present on any available carbon or nitrogen atom of the ring Cy is selected from a halogen atom or -(Alk$^4$)$_v$L$^1$(Alk$^1$)$_n$R$^3$ in which Alk$^4$ is a straight or branched C$_{1-3}$alkylene chain, v is zero or the integer 1, L$^1$ is a covalent bond or a linker atom or group, n is zero or the integer 1, Alk$^1$ is an optionally substituted aliphatic chain and R$^3$ is a hydrogen atom or a —CN, —NO$_2$ or an optionally substituted heteroaliphatic, cycloaliphatic, heterocycloaliphatic, polycycloaliphatic, heteropolycycloaliphatic, aromatic or heteroaromatic group;

p is zero or the integer 1, 2, 3 or 4;

provided that Cy is not a cyclobutenedione group;

and the salts, solvates, hydrates and N-oxides thereof.

2. A compound according to claim 1 in which Alk is a chain: —CH—CH(R)— or

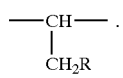

3. A compound according to claim 1 in which R is an esterified carboxyl group of formula —CO$_2$Alk$^7$.

4. A compound according to claim 1 in which R$^2$ is a hydrogen atom.

5. A compound according to claim 1 in which Ar$^2$ is an optionally substituted phenylene group.

6. A compound according to claim 1 in which Cy is optionally substituted unsaturated cycloaliphatic or heterocyclo-aliphatic ring in which m is the integer 1 and R$^x$ is an oxo (═O) substituent.

7. A compound according to claim 6 which Cy is a optionally substituted cyclopentenyl, cyclohexenyl, cycloheptenyl, dihydropyrimidinyl, dihydropyridinyl or imidazolinyl group.

8. A compound according to claim 1 in which X is a N atom.

9. A compound according to claim 8 in which Cy is a optionally substituted 2-aminopyridin-4-one [where amino refers to the group —N(R$^2$)—], 4-aminopyrimidin-2-one, 2-aminopyridin-4-one, 6-aminopyridin-2-one or 2-aminoimiadozolin-4-one ring.

10. A compound according to claim 1 in which X is a C(R$^w$) group.

11. A compound according to claim 10 in which Cy is a optionally substituted 3-amino-2-cyclopenten-1-one or 3-amino-2-cyclohexen-1-one ring.

12. A compound according to claim 11 in which p is zero or the integer 1 or 2.

13. A compound according to claim 1 in which v in the group R$^z$ is zero, Alk$^1$ is an aliphatic chain and R$^3$ is a hydrogen atom.

14. A compound according to claim 13 in which -Alk$^1$R$^3$ is an optionally substituted C$_{1-6}$alkyl, allyl, (—CH$_2$CH═CH$_2$) or propargyl (—CH$_2$CCH) group.

15. A compound according to claim 14 in which L$^1$ is a covalent bond.

16. A pharmaceutical composition comprising a compound according to claim 1 together with one or more pharmaceutically acceptable carriers, excipients or diluents.

17. A method for the prophylaxis or treatment of a disease or disorder in a mammal in which the extravasation of leukocytes plays a role, comprising administering to a mammal suffering from such a disease or disorder a therapeutically effective amount of a compound according to formula (1):

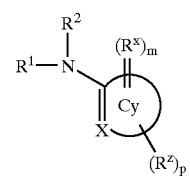

(1)

wherein

R$^1$ is a group Ar$^1$L$^2$Ar$^2$Alk- in which Ar$^1$ is an optionally substituted phenyl group, L$^2$ is a covalent bond or a linker atom or group, Ar$^2$ is an optionally substituted arylene or heteroarylene group and Alk is a chain —CH$_2$—CH(R)—, —CH═C(R)—,

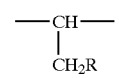

in which R is a carboxylic acid derivative or biostere;

R$^2$ is a hydrogen atom or a C$_{1-6}$alkyl group;

the ring Cy is an unsaturated cycloaliphatic or heterocycloaliphatic ring containing X, in which X is a N atom or a C(R$^w$) group;

R$^w$ is a group R$^z$;

R$^x$ which may be present or any available carbon atom of the ring Cy is a oxo (═O), thioxo (═S) or imino (═NR$^{30}$) group in which R$^{30}$ is an aliphatic, heteroaliphatic, cycloaliphatic, heterocycloaliphatic, aromatic or hetero-aromatic group;

m is zero or the integer 1, 2 or 3;

$R^z$ which may be present on any available carbon or nitrogen atom of the ring Cy is selected from a halogen atom or -$(Alk^4)_vL^1(Alk^1)_nR^3$ in which $Alk^4$ is a straight or branched $C_{1-3}$alkylene chain, v is zero or the integer 1, $L^1$ is a covalent bond or a linker atom or group, n is zero or the integer 1, $Alk^1$ is an optionally substituted aliphatic chain and $R^3$ is a hydrogen atom or a —CN, —NO$_2$ or an optionally substituted heteroaliphatic, cycloaliphatic, heterocycloaliphatic, polycycloaliphatic, heteropolycycloaliphatic, aromatic or heteroaromatic group;

p is zero or the integer 1, 2, 3 or 4;

provided that Cy is not a cyclobutenedione group;

and the salts, solvates, hydrates and N-oxides thereof.

18. A method according to claim 17 wherein said disease or disorder is selected from the group consisting of inflammatory arthritis, multiple sclerosis, allograft rejection, diabetes, inflammatory dermatoses, asthma, and inflammatory bowel disease.

19. A method according to claim 18 wherein the inflammatory arthritis is selected from the group consisting of rheumatoid arthritis vasculitis and polydermatomyositis.

20. A method according to claim 18 wherein the inflammatory dermatoses are selected from the group consisting of psoriasis and dermatitis.

* * * * *